US012655221B2

(12) United States Patent
Spriggs et al.

(10) Patent No.: US 12,655,221 B2
(45) Date of Patent: Jun. 16, 2026

(54) ANTIBODIES TO GALECTIN-3 AND METHODS OF USE THEREOF

(71) Applicants: MEMORIAL SLOAN KETTERING CANCER CENTER, New York, NY (US); TRI-INSTITUTIONAL THERAPEUTICS DISCOVERY INSTITUTE, INC., New York, NY (US)

(72) Inventors: David Spriggs, New York, NY (US); Dharmarao Thapi, New York, NY (US); Ivo C. Lorenz, New York, NY (US); Thomas E. White, New York, NY (US)

(73) Assignees: MEMORIAL SLOAN KETTERING CANCER CENTER, New York, NY (US); TRI-INSTITUTIONAL THERAPEUTICS DISCOVERY INSTITUTE, INC., New York, NY (US)

( * ) Notice: Subject to any disclaimer, the term of this patent is extended or adjusted under 35 U.S.C. 154(b) by 561 days.

(21) Appl. No.: 18/256,384

(22) PCT Filed: Dec. 7, 2021

(86) PCT No.: PCT/US2021/062099
§ 371 (c)(1),
(2) Date: Jun. 7, 2023

(87) PCT Pub. No.: WO2022/125482
PCT Pub. Date: Jun. 16, 2022

(65) Prior Publication Data
US 2024/0026009 A1     Jan. 25, 2024

Related U.S. Application Data

(60) Provisional application No. 63/122,714, filed on Dec. 8, 2020.

(51) Int. Cl.
| | |
|---|---|
| *C07K 16/28* | (2006.01) |
| *A61K 47/68* | (2017.01) |
| *A61K 49/00* | (2006.01) |
| *A61P 35/00* | (2006.01) |

(52) U.S. Cl.
CPC ...... *C07K 16/2851* (2013.01); *A61K 47/6849* (2017.08); *A61K 49/0002* (2013.01); *A61P 35/00* (2018.01); *C07K 16/2809* (2013.01); *C07K 2317/21* (2013.01); *C07K 2317/24* (2013.01); *C07K 2317/31* (2013.01); *C07K 2317/622* (2013.01)

(58) Field of Classification Search
None
See application file for complete search history.

(56) References Cited

U.S. PATENT DOCUMENTS

| | | | | |
|---|---|---|---|---|
| 11,427,638 | B2 * | 8/2022 | Sun | C07K 16/2851 |
| 12,180,285 | B2 * | 12/2024 | Spriggs | A61P 35/04 |
| 12,497,458 | B2 * | 12/2025 | Sun | C07K 16/2851 |

FOREIGN PATENT DOCUMENTS

| | | |
|---|---|---|
| AU | 2020201807 A1 | 4/2020 |
| WO | WO-2014/160499 A2 | 10/2014 |
| WO | WO-2016/073906 A2 | 5/2016 |
| WO | WO-2017/119434 A1 | 7/2017 |
| WO | WO-2019/023247 A1 | 1/2019 |
| WO | WO-2019/068863 A1 | 4/2019 |
| WO | WO-2019/152895 A1 | 8/2019 |

OTHER PUBLICATIONS

Cristina Caldas et al: "Humanization of the anti-CD18 antibody 6.7: an unexpected effect of a framework residue in binding to antigen.", Molecular Immunology, vol. 39, No. 15, May 1, 2003 (12, pages).
Du J et al: "Molecular basis of recognition of human osteopontin by 23C3, a potential therapeutic antibody for treatment of rheumatoid arthritis", Journal of Molecular Biology, United Kingdom, vol. 382, No. 4, Oct. 17, 2008, (8, pages).
Freitag Nancy et al: "Galectin-3 deficiency in pregnancy increases the risk of fetal growth restriction (FGR) via placental insufficiency", Cell Death and Disease, vol. 11, No. 7, 23 Jul. 23, 020, (9, pages).
Jianhua X et al: "Modification in framework region I results in a decreased affinity of chimeric anti-TAG72 antibody", Molecular Immunology, Pergamon, GB, vol. 28, No. 1-2, Jan. 1, 1991, (8, pages).
Panka DJ et al: "Variable Region Framework Differences Result in Decreased or Increased Affinity of Variant Anti-digoxin Antibodies," Proceedings of the National Academy of Science, vol. 85, No. 9, May 1, 1988 (5, pages).
International Search Report on PCT PCT/US2021/062099 dated May 17, 2022.
Fukaya et al: "Identification of galectin-3-binding protein as a factor secreted by tumor cells that stimulates interleukin-6 expression in the bone marrow stroma", Journal of Biological Chemistry, American Society for Biochemistry and Molecular Biology, US, vol. 283, No. 27, Jul. 4, 2008 (Jul. 4, 2008) , pp. 18573-18581.

* cited by examiner

*Primary Examiner* — Daniel C Gamett
(74) *Attorney, Agent, or Firm* — Foley & Lardner LLP

(57) ABSTRACT

Provided herein are compositions, methods, and uses involving antibodies that specifically bind the Galectin-3 (LGALS3) carbohydrate binding domain (CBD). Also provided herein are uses and methods for managing, treating, or preventing disorders, such as cancer.

20 Claims, 14 Drawing Sheets
Specification includes a Sequence Listing.

Role of LGALS3 linking cancer mucin to signaling molecules (EGFR and IntegrinB)

FIG. 2A

Known *In Vitro* / *In Vivo* Experimental Functions of Galectin 3

| GAL3 Function | Description of GAL3 effect | Potential Blocking Ab effect | References |
|---|---|---|---|
| Immune function | -CD8 T-cell Suppression via LAG3<br>-Decrease monocyte migration and enhance apoptosis<br>-Promotes T-cell Apoptosis<br>-Suppressed TCR activation infiltrating tumor | T cell activation<br>Monocyte activation<br>Decreased T cell apoptosis<br>Rescues T cell suppression | Kouo, T., *et al.*, Cancer Immunol Res, 2015. 3(4): 412-23<br>Paclik, D., *et al.*, Cell Immunol, 2011. 271(1): 97-103<br>Guha, P., *et al.*, *Proc Natl Acad Sci U S A*, 2013. 110(13): 5052-7<br>Chen, H.Y., *et al.*, *Proc Natl Acad Sci U S A*, 2009. 106(34): 14496-501 |
| Thrombosis | GAL3 promotes venous thrombosis | Decreased thrombosis | DeRoo, E.P., *et al.*, Blood, 2015. 125(11): 1813-21 |
| Metastasis promotion | GAL3 promotes bone metastasis<br><br>GAL3 promotes metastasis by microenvironment changes | Decrease metastasis<br><br>Decrease metastasis | Nakajima, K., *et al.*, Cancer Metastasis Rev, 2016. 35(2): 333-46<br>Ruvolo, P.P., *Biochim Biophys Acta*, 2016. 1863(3): p. 427-37 |
| Cardiac | Elevated in heart failure / fibrosis | Less CHF /fibrosis | Lala, R.I., *et al.*, *Acta Cardiol*, 2015. 70(3): 323-31 |
| Renal | GAL3 Increased in lupus GN, fibrosis and loss of GFR | Decreased inflammation in renal disease | Chen, S.C. and P.L. Kuo, *Int J Mol Sci*, 2016. 17(4): 565 |
| Pulmonary | GAL3 increased in pulmonary fibrosis syndromes | Decreased fibrosis | Nishi, Y., *et al.*, *Allergol Int*, 2007. 56(1): 57-65 |
| Infection control | Promotion of neutrophil activation | Decrease local neutrophil recruitment | Wright, R.D., *et al.*, *J Leukoc Biol*, 2017. 101(3): 717-726 |
| Endocrine | GAL3 loss exacerbates hyperglycemia in K/O mice on high fat diet | Hyperglycemia | Darrow, A.L. and R.V. Shohet, *Cardiovasc Diabetol*, 2015. 14: 73 |
| Angiogenesis | GAL3 promotes angiogenesis via stabilized VEGFR2<br>GAL3 promotes drug resistance and angiogenesis in ovarian cancer | Decreased angiogenesis<br>Decreased drug resistance | Jia, W., *et al.*, *Am J Pathol*, 2013. 182(5): 1821-31<br>Mirandola, L., *et al.*, *Gynecol Oncol*, 2014. 135(3): 573-9;<br>Ebrahim, A.H., *et al.*, *Ann Transl Med*, 2014. 2(9): 88; Mirandola, L., *et al.*, *Int Rev Immunol*, 2014. 33(5): p. 417-27; Pena, C., *et al.*, *Ann Transl Med*, 2014. 2(9): 87 |

Galectin-3 Carbohydrate Binding Domain

GNDVAFHF NPRFNENNRR VIVCNTKLDN NWGREERQSV FPFESG
160              170              180              190

FIG. 5A

| | 1 |
|---|---|
| 39F02 | 0.726 |
| 38E05 | 1.122 |
| 20F08 | 0.047 |
| 12H07 | 0.049 |
| 46H02 | 1.384 | moGal3

FIG. 5B

| 6 | 7 |
|---|---|
| 39F02 | 0.502 |
| 38E05 | 0.86 |
| 20F08 | 0.523 |
| 12H07 | 1.403 |
| 46H02 | 2.564 | huGal3

KD = 10nM

20F08

KD = 44nM (1) ▨ anti-mouse kappa
(2) ▨ anti-mouse lambda
(3) ▨ anti-human kappa
(4) ▨ anti-human lambda

SEQUENCE LISTING

```
<160> NUMBER OF SEQ ID NOS: 58

<210> SEQ ID NO 1
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Val Glu Ile Lys
            100                 105                 110

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ser Leu Val Tyr Ser Asp Gly Asn Thr Tyr
1               5                   10

<210> SEQ ID NO 3
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Val Ser
1

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

```
Met Gln Gly Thr His Trp Pro Leu Thr
1               5
```

<210> SEQ ID NO 5
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gatgtggtga tgactcagag tccgctcagc ctgcccgtca cccttggaca gccggcctcc      60
atctcctgca ggtctagtca aagcctcgta tacagtgatg gaaacaccta cttgaattgg     120
tttcagcaga ggccaggcca atctccaagg cgcctaattt ataaggtttc taaccgggac     180
tctggggtcc cagacagatt cagcggcagt gggtcaggca ctgatttcac actgaaaatc     240
agcagggtgg aggctgagga tgttgggggtt tattactgca tgcaaggtac acactggcct     300
ctcactttcg gcggagggac caaggtggag atcaaa                               336
```

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ser Met His Trp Val Arg Gln Ala Pro Gly Gln Gly Leu Glu Trp Met
            35                  40                  45

Gly Trp Ile Asn Pro His Ser Gly Gly Thr Asn Ser Ala Gln Lys Phe
        50                  55                  60

Gln Gly Arg Val Thr Met Thr Arg Asp Thr Ser Ile Gly Thr Ala Tyr
65                  70                  75                  80

Met Glu Leu Asn Arg Leu Arg Ser Asp Asp Thr Ala Val Tyr Tyr Cys
                85                  90                  95

Val Arg Asp Asn Pro Ile Thr Gly Phe Asp Tyr Trp Gly Gln Gly Thr
                100                 105                 110

Leu Val Thr Val Ser Ser
            115
```

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gly Tyr Thr Phe Thr Gly Tyr Ser
1               5
```

<210> SEQ ID NO 8
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Asn Pro His Ser Gly Gly Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Arg Asp Asn Pro Ile Thr Gly Phe Asp Tyr
1               5                   10

<210> SEQ ID NO 10
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
caggtgcagc tggtgcagtc tggggctgag gtgaagaagc ctggggcctc agtgaaggtc      60
tcctgcaagg cttctggata caccttcacc ggctattcta tgcactgggt gcgacaggcc     120
cctggacaag ggcttgagtg gatgggatgg atcaaccctc acagtggtgg cacaaattct     180
gcacagaagt ttcagggcag ggtcaccatg accagggaca cgtccatcgg cacagcctac     240
atggagctga caggctgag atctgacgac acggccgtgt attactgtgt gagagataac     300
cctataactg ggtttgacta ctggggccag ggaaccctgg tcaccgtctc ctcag          355

<210> SEQ ID NO 11
<211> LENGTH: 958
<212> TYPE: DNA
<213> ORGANISM: Homo sapiens

<400> SEQUENCE: 11
gcccgcagca cctcctcgcc agcagccgtc cggagccagc caacgagcgg aaaatggcag      60
acaatttttc gctccatgat gcgttatctg ggtctggaaa cccaaaccct caaggatggc     120
ctggcgcatg ggggaaccag cctgctgggg caggggcta cccaggggct tcctatcctg      180
gggcctaccc cgggcaggca cccccagggg cttatcctgg acaggcacct ccaggcgcct     240
accctggagc acctggagct tatcccggag cacctgcacc tggagtctac ccagggccac     300
ccagcggccc tggggcctac ccatcttctg gacagccaag tgccaccgga gcctaccctg     360
ccactggccc ctatggcgcc cctgctgggc cactgattgt gccttataac ctgcctttgc     420
ctgggggagt ggtgcctcgc atgctgataa caattctggg cacggtgaag cccaatgcaa     480
acagaattgc tttagatttc caaagaggga atgatgttgc cttccacttt aacccacgct     540
tcaatgagaa caacaggaga gtcattgttt gcaatacaaa gctggataat aactggggaa     600
gggaagaaag acagtcggtt ttcccatttg aaagtgggaa accattcaaa atacaagtac     660
tggttgaacc tgaccacttc aaggttgcag tgaatgatgc tcacttgttg cagtacaatc     720
```

-continued

```
atcgggttaa aaaactcaat gaaatcagca aactgggaat ttctggtgac atagacctca       780
ccagtgcttc atataccatg atataatctg aaaggggcag attaaaaaaa aaaaaagaat       840
ctaaacctta catgtgtaaa ggtttcatgt tcactgtgag tgaaaatttt tacattcatc       900
aatatccctc ttgtaagtca tctacttaat aaatattaca gtgaattacc tgtctcaa        958
```

<210> SEQ ID NO 12
<211> LENGTH: 250
<212> TYPE: PRT
<213> ORGANISM: Homo sapiens

<400> SEQUENCE: 12

```
Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
            115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
            195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250
```

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Glu Thr Thr Val Thr Gln Ser Pro Ala Ser Leu Ser Met Ala Ile Gly
1               5                   10                  15
```

```
Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Ile Leu Arg Pro Gly Val Pro Ser Arg Phe Ser Ser
    50                  55                  60

Ser Gly Tyr Gly Thr Asp Phe Val Phe Ala Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Leu Lys
            100                 105
```

```
<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Asp Ile Asp Asp Asp
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Gly Asn
1

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gln Ser Asp Asn Leu Pro Tyr Thr
1               5

<210> SEQ ID NO 17
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gaaacaactg tgacccagtc tccagcatcc ctgtccatgg ctataggaga aaaagtcacc      60
atcagatgca taaccagcac tgatattgat gatgatatga actggtacca gcagaagcca     120
ggggaacctc ctaagctcct tatttcagaa ggcaatattc ttcgtcctgg agtcccatcc     180
cgattctcca gcagtggcta cggtacagat tttgtttttg caattgaaaa catgctctca     240
```
gaagatgttg cagattacta ctgtttgcaa agtgataact tgccgtacac gttcggaggg    300
gggaccaagc tggaactaaa a    321

<210> SEQ ID NO 18
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Tyr
            20                  25                  30

Asn Ile Asn Trp Val Arg Gln Ala Pro Gly Lys Gly Leu Glu Trp Val
            35                  40                  45

Ser Cys Val Ser Arg Ser Asn Tyr Thr Tyr Tyr Thr Asp Ser Val Lys
        50                  55                  60

Gly Arg Phe Thr Ile Ser Arg Asp Asn Ala Lys Lys Ser Leu Tyr Leu
65                  70                  75                  80

Gln Met Asn Ser Leu Arg Ala Glu Asp Thr Ala Val Tyr Tyr Cys Ala
                85                  90                  95

Arg Asp Cys Gly Thr Tyr Gly Val Phe Asp Tyr Trp Gly Gln Gly Thr
            100                 105                 110

Leu Val Thr Val Ser Ser
        115

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Ile Phe Ser Asn Tyr Asn
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Val Ser Arg Ser Asn Tyr Thr
1               5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Arg Asp Cys Gly Thr Tyr Gly Val Phe Asp Tyr 1                       5                        10

<210> SEQ ID NO 22
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gaggtgcagc tggtggagtc tggggggaggc ctggtcaagc cggggggggtc cctgagactc      60 tcctgtgcag cctctggatt tatattcagt aattataata taaactgggt ccgccaggct      120
ccagggaagg ggctggagtg ggtctcatgt gttagtagga gtaattacac atactacaca      180
gactcagtga agggccgatt caccatctcc agagacaacg ccaagaagtc actgtatctg      240
caaatgaaca gcctgagagc cgaggacacg gctgtgtatt actgtgcgag agactgtggg      300
acctatgggg tctttgacta ttggggccag ggaaccctgg tcaccgtctc ctcag        355

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Thr Thr Val Thr Gln Ser Pro Ala Ser Leu Ser Met Ala Ile Gly
1                       5                        10                          15

Glu Lys Val Thr Ile Arg Cys Ile Thr Ser Thr Asp Ile Asp Asp Asp
                    20                          25                          30

Met Asn Trp Tyr Gln Gln Lys Pro Gly Glu Pro Pro Lys Leu Leu Ile
                35                          40                          45

Ser Glu Gly Asn Ile Leu Arg Pro Gly Val Pro Ser Arg Phe Ser Ser
            50                          55                          60

Ser Gly Tyr Gly Thr Asp Phe Val Phe Ala Ile Glu Asn Met Leu Ser
65                          70                          75                          80

Glu Asp Val Ala Asp Tyr Tyr Cys Leu Gln Ser Asp Asn Leu Pro Tyr
                        85                          90                          95

Thr Phe Gly Gly Gly Thr Lys Leu Glu Leu Lys
                100                         105

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Asp Ile Asp Asp Asp
1                       5

<210> SEQ ID NO 25
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Gly Asn
1

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Gln Ser Asp Asn Leu Pro Tyr Thr
1               5

<210> SEQ ID NO 27
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gaaacaactg tgacccagtc tccagcatcc ctgtccatgg ctataggaga aaaagtcacc        60
atcagatgca taaccagcac tgatattgat gatgatatga actggtacca gcagaagcca       120
ggggaacctc ctaagctcct tatttcagaa ggcaatattc ttcgtcctgg agtcccatcc       180
cgattctcca gcagtggcta cggtacagat tttgttttg caattgaaaa catgctctca       240
gaagatgttg cagattacta ctgtttgcaa agtgataact gccgtacac gttcggaggg       300 gggaccaagc tggaactaaa a                                                 321

<210> SEQ ID NO 28
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Tyr
                20                  25                  30

Asn Ile Asn Trp Val Arg Gln Ala Pro Gly Lys Gly Leu Glu Trp Val
            35                  40                  45

Ser Cys Val Ser Arg Ser Asn Tyr Thr Tyr Tyr Thr Asp Ser Val Lys
        50                  55                  60

Gly Arg Phe Thr Ile Ser Arg Asp Asn Ala Lys Lys Ser Leu Tyr Leu
65                  70                  75                  80

Gln Met Asn Ser Leu Arg Ala Glu Asp Thr Ala Val Tyr Tyr Cys Ala
                85                  90                  95

Arg Asp Cys Gly Thr Tyr Gly Val Phe Asp Tyr Trp Gly Gln Gly Thr
                100                 105                 110

Leu Val Thr Val Ser Ser
        115

```
<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Ile Phe Ser Asn Tyr Asn
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Val Ser Arg Ser Asn Tyr Thr
1               5

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Arg Asp Cys Gly Thr Tyr Gly Val Phe Asp Tyr
1               5                   10

<210> SEQ ID NO 32
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gaggtgcagc tggtggagtc tgggggaggc ctggtcaagc cggggggggtc cctgagactc      60 tcctgtgcag cctctggatt tatattcagt aattataata taaactgggt ccgccaggct     120
ccagggaagg ggctggagtg ggtctcatgt gttagtagga gtaattacac atactacaca     180
gactcagtga agggccgatt caccatctcc agagacaacg ccaagaagtc actgtatctg     240
caaatgaaca gcctgagagc cgaggacacg gctgtgtatt actgtgcgag agactgtggg     300
acctatgggg tctttgacta ttggggccag ggaaccctgg tcaccgtctc ctcag         355

<210> SEQ ID NO 33
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Val Met Ser Gln Ser Pro Ser Ser Leu Ala Val Ser Val Gly
1               5                   10                  15

Glu Lys Val Thr Leu Ser Cys Lys Ser Ser Gln Ser Leu Leu Tyr Gly
```

-continued

```
                 20                    25                    30

Asp Asp Gln Lys Asn Tyr Leu Ala Trp Tyr Gln Gln Lys Pro Gly Gln
         35                    40                    45

Ser Pro Lys Leu Leu Leu Tyr Trp Ala Ser Thr Trp Glu Ser Gly Val
         50                    55                    60

Pro Asp Arg Phe Thr Gly Ser Gly Ser Gly Thr Asp Phe Thr Leu Thr
65                    70                    75                    80

Ile Ser Ser Val Lys Ala Ala Asp Leu Ala Val Tyr Tyr Cys Gln Gln
                 85                    90                    95

Tyr Tyr Ser Tyr Pro Trp Thr Phe Gly Gly Gly Thr Lys Leu Glu Ile
                 100                   105                   110

Lys
```

```
<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Leu Leu Tyr Gly Asp Asp Gln Lys Asn Tyr
1               5                   10
```

```
<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ala Ser
1
```

```
<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Tyr Tyr Ser Tyr Pro Trp Thr
1               5
```

```
<210> SEQ ID NO 37
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gacattgtga tgtcacagtc tccatcctcc ctagctgtgt cagttggaga gaaggttact      60
ctgagctgca agtccagtca gagccttta tatggtgacg atcaaaagaa ctacttggcc      120
tggtaccaac agaaaccagg acagtctcct aaactgcttc tttactgggc atccacttgg      180
gaatctgggg tccctgatcg cttcacaggc agtggatctg ggacagattt cactctcacc      240
```
atcagcagtg tgaaggctgc agacctggca gtttattact gtcagcaata ttatagctat          300
ccgtggacgt tcggtggagg caccaagctg gaaatcaaa                                  339

<210> SEQ ID NO 38
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Gly Thr Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ala Trp Ile Ser Tyr Phe Asp Tyr Trp Gly Gln Gly Thr
            100                 105                 110

Leu Val Thr Val Ser Ser
        115

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Phe Thr Leu Ser Asn Tyr Ala
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Ser Gly Ser Gly Gly Gly Thr
1               5

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Lys Glu Ala Trp Ile Ser Tyr Phe Asp Tyr
1               5                   10

<210> SEQ ID NO 42
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gaagtacagc tgttggagtc tggggggaggc ttggtacagc ctggggggtc cctgagactc      60
tcctgtgcag cctctggatt caccccttagt aactatgcca tgagctgggt ccgccaggcg     120
ccagggaagg ggctggagtg ggtctcagct atcagtggta gtggtggtgg cacatacaac     180
gcagactccg tgaagggccg gttcaccatc tccagagaca attccaagaa cacgctgtat     240
ctgcaaatga acagcctgag agccgaggac acggccgtgt attactgtgc gaaagaggcg     300
tggatctcgt actttgacta ctggggccag gggaccctgg tcaccgtctc ctcag          355

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Val Met Ser Gln Ser Pro Ser Ser Leu Ala Val Ser Val Gly
1               5                   10                  15

Glu Lys Val Thr Leu Ser Cys Lys Ser Ser Gln Ser Leu Leu Tyr Gly
            20                  25                  30

Asp Asp Gln Lys Asn Tyr Leu Ala Trp Tyr Gln Gln Lys Pro Gly Gln
        35                  40                  45

Ser Pro Lys Leu Leu Leu Tyr Trp Ala Ser Thr Trp Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Ala Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ser Leu Leu Tyr Gly Asp Asp Gln Lys Asn Tyr
1               5                   10

<210> SEQ ID NO 45
<211> LENGTH: 3
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 45

Trp Ala Ser
1

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Tyr Tyr Ser Tyr Pro Trp Thr
1               5

<210> SEQ ID NO 47
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gacattgtga tgtcacagtc tccatcctcc ctagctgtgt cagttggaga gaaggttact      60
ctgagctgca agtccagtca gagcctttta tatggtgacg atcaaaagaa ctacttggcc     120
tggtaccaac agaaaccagg acagtctcct aaactgcttc tttactgggc atccacttgg     180
gaatctgggg tccctgatcg cttcacaggc agtggatctg ggacagattt cactctcacc     240
atcagcagtg tgaaggctgc agacctggca gtttattact gtcagcaata ttatagctat     300
ccgtggacgt tcggtggagg caccaagctg gaaatcaaa                            339

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ala Trp Ile Ser Tyr Phe Asp Tyr Trp Gly Gln Gly Thr
            100                 105                 110

Leu Val Thr Val Ser Ser
```

115

```
<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Leu Ser Asn Tyr Ala
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Ser Gly Ser Gly Gly Gly Thr
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Lys Glu Ala Trp Ile Ser Tyr Phe Asp Tyr
1               5                   10

<210> SEQ ID NO 52
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gaagtacagc tgttggagtc tggggggaggc ttggtacagc ctggggggtc cctgagactc      60
tcctgtgcag cctctggatt cacccttagt aactatgcca tgagctgggt ccgccaggcg     120
ccagggaagg ggctggagtg ggtctcagct atcagtggta gtggtggtgg cacatacaac     180
gcagactccg tgaagggccg gttcaccatc tccagagaca attccaagaa cacgctgtat     240
ctgcaaatga acagcctgag agccgaggac acggccgtgt attactgtgc gaaagaggcg     300
tggatctcgt actttgacta ctggggccag gggaccctgg tcaccgtctc ctcag          355

<210> SEQ ID NO 53
<211> LENGTH: 249
<212> TYPE: PRT
<213> ORGANISM: Unknown
<220> FEATURE:
<223> OTHER INFORMATION: Description of Unknown:
      GAL-3 immunogen sequnce

<400> SEQUENCE: 53

Ala Asp Asn Phe Ser Leu His Asp Ala Leu Ser Gly Ser Gly Asn Pro
```

```
1                   5                   10                  15

Asn Pro Gln Gly Trp Pro Gly Ala Trp Gly Asn Gln Pro Ala Gly Ala
            20                  25                  30

Gly Gly Tyr Pro Gly Ala Ser Tyr Pro Gly Ala Tyr Pro Gly Gln Ala
            35                  40                  45

Pro Pro Gly Ala Tyr Pro Gly Gln Ala Pro Pro Gly Ala Tyr Pro Gly
    50                  55                  60

Ala Pro Gly Ala Tyr Pro Gly Ala Pro Ala Pro Gly Val Tyr Pro Gly
65                  70                  75                  80

Pro Pro Ser Gly Pro Gly Ala Tyr Pro Ser Ser Gly Gln Pro Ser Ala
                85                  90                  95

Thr Gly Ala Tyr Pro Ala Thr Gly Pro Tyr Gly Ala Pro Ala Gly Pro
                100                 105                 110

Leu Ile Val Pro Tyr Asn Leu Pro Leu Pro Gly Gly Val Val Pro Arg
            115                 120                 125

Met Leu Ile Thr Ile Leu Gly Thr Val Lys Pro Asn Ala Asn Arg Ile
    130                 135                 140

Ala Leu Asp Phe Gln Arg Gly Asn Asp Val Ala Phe His Phe Asn Pro
145                 150                 155                 160

Arg Phe Asn Glu Asn Asn Arg Arg Val Ile Val Cys Asn Thr Lys Leu
                165                 170                 175

Asp Asn Asn Trp Gly Arg Glu Glu Arg Gln Ser Val Phe Pro Phe Glu
                180                 185                 190

Ser Gly Lys Pro Phe Lys Ile Gln Val Leu Val Glu Pro Asp His Phe
            195                 200                 205

Lys Val Ala Val Asn Asp Ala His Leu Leu Gln Tyr Asn His Arg Val
    210                 215                 220

Lys Lys Leu Asn Glu Ile Ser Lys Leu Gly Ile Ser Gly Asp Ile Asp
225                 230                 235                 240

Leu Thr Ser Ala Ser Tyr Thr Met Ile
                245

<210> SEQ ID NO 54
<211> LENGTH: 128
<212> TYPE: PRT
<213> ORGANISM: Unknown
<220> FEATURE:
<223> OTHER INFORMATION: Description of Unknown:
      LGALS3 sequence

<400> SEQUENCE: 54

Pro Tyr Asn Leu Pro Leu Pro Gly Gly Val Val Pro Arg Met Leu Ile
1                   5                   10                  15

Thr Ile Leu Gly Thr Val Lys Pro Asn Ala Asn Arg Ile Ala Leu Asp
            20                  25                  30

Phe Gln Arg Gly Asn Asp Val Ala Phe His Phe Asn Pro Arg Phe Asn
            35                  40                  45

Glu Asn Asn Arg Arg Val Ile Val Cys Asn Thr Lys Leu Asp Asn Asn
    50                  55                  60

Trp Gly Arg Glu Glu Arg Gln Ser Val Phe Pro Phe Glu Ser Gly Lys
65                  70                  75                  80

Pro Phe Lys Ile Gln Val Leu Val Glu Pro Asp His Phe Lys Val Ala
                85                  90                  95

Val Asn Asp Ala His Leu Leu Gln Tyr Asn His Arg Val Lys Lys Leu
            100                 105                 110
```

Asn Glu Ile Ser Lys Leu Gly Ile Ser Gly Asp Ile Asp Leu Thr Ser
        115                 120                 125

<210> SEQ ID NO 55
<211> LENGTH: 384
<212> TYPE: DNA
<213> ORGANISM: Unknown
<220> FEATURE:
<223> OTHER INFORMATION: Description of Unknown:
      LGALS3 sequence

<400> SEQUENCE: 55
ccttataacc tgcctttgcc tgggggagtg gtgcctcgca tgctgataac aattctgggc        60
acggtgaagc ccaatgcaaa cagaattgct ttagatttcc aaagagggaa tgatgttgcc       120
ttccacttta acccacgctt caatgagaac aacaggagag tcattgtttg caatacaaag       180
ctggataata actggggaag ggaagaaaga cagtcggttt tcccatttga aagtgggaaa       240
ccattcaaaa tacaagtact ggttgaacct gaccacttca aggttgcagt gaatgatgct       300
cacttgttgc agtacaatca tcgggttaaa aaactcaatg aaatcagcaa actgggaatt       360
tctggtgaca tagacctcac cagt                                              384

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 57

His His His His His His
1               5

<210> SEQ ID NO 58
<211> LENGTH: 44
<212> TYPE: PRT
<213> ORGANISM: Unknown
<220> FEATURE:
<223> OTHER INFORMATION: Description of Unknown:
      LGALS3 sequence

<400> SEQUENCE: 58

Gly Asn Asp Val Ala Phe His Phe Asn Pro Arg Phe Asn Glu Asn Asn
1               5                   10                  15

Arg Arg Val Ile Val Cys Asn Thr Lys Leu Asp Asn Asn Trp Gly Arg
            20                  25                  30

Glu Glu Arg Gln Ser Val Phe Pro Phe Glu Ser Gly
        35                  40

ANTIBODIES TO GALECTIN-3 AND METHODS OF USE THEREOF

CROSS-REFERENCE TO RELATED APPLICATIONS

This application is a U.S. National Stage Application under 35 U.S.C. § 371 of International Patent Application No. PCT/US2021/062099, filed Dec. 7, 2021, which claims the benefit of and priority to U.S. Provisional Patent Application No. 63/122,714, filed Dec. 8, 2020, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jan. 12, 2021, is named 115872-2370_SL.txt and is 33,075 bytes in size.

TECHNICAL FIELD

The present technology relates generally to the preparation of immunoglobulin-related compositions (e.g., antibodies or antigen binding fragments thereof) that specifically bind Galectin-3 protein and uses of the same. In particular, the present technology relates to the preparation of Galectin-3 binding antibodies and their use in detecting and treating Galectin-3-associated cancers, cardiovascular disease, fibrosis, and inflammation.

BACKGROUND

Galectins are a family of small, highly conserved eukaryotic proteins which recognize specific complex sugars on glycosylated cell surface proteins. They are essential for linking cancer cells with the stromal microenvironment to modulate development, adhesion, signaling, invasions and immune system interactions. Galectins can be found in the nucleus, the cytoplasm and the pericellular space. Extracellular galectins are primarily released in exosomes and do not appear to have classic secretion from the ER or Golgi. Humans have at least 12 different galectins which are variably expressed in various tissues and stages on development. In the last decade, it has become apparent that human Galectins, particularly Galectin-3 (LGALS3), represent an important link between the microenvironment and the tumor cell. In particular, biologic functions of glycoproteins and other surface glycans are primarily dependent on the specific sugar chains attached in the Golgi leading to unique Galectin selectivity. Outside the cell, LGALS3 participates in regulation of cell membrane residence time, adhesion, migration, invasion and angiogenesis functions. Although LGALS3 binds to other natural ligands, its highest affinity ligand is the most proximal lactosamine disaccharide in poly-lactosamine chains that decorate many O- and N-Glycan species. Through binding and polymerization, LGALS3 forms a lattice and regulates the position and residence time of growth factor receptors including EGFR, PDGFR, Integrins and CTLA4, among many others (FIGS. 1A-1B). Activation of downstream signaling molecules, such as SRC, ERK, AKT, and FAK drives the production of key molecules involved in metastasis and invasion. On the surface of T-cells, CTLA4 surface concentrations are stabilized by LGALS3, leading to immunosuppression. Loss of the LGALS3 lattice inhibits multiple cancer cell and immune cell behaviors. In addition to cancer, excess LGALS3 has also been linked to renal disease, hepatic fibrosis, pulmonary fibrosis, cardiac failure and parasitic diseases (see FIG. 2A).

SUMMARY OF THE PRESENT TECHNOLOGY

Provided herein are compositions, methods, and uses involving antibodies that specifically bind to Galectin-3 (LGALS3), and modulate expression and/or activity of LGALS3 for managing or treating LGALS-mediated disorders, such as cancer. The present disclosure provides antibodies or antigen-binding fragments thereof that specifically bind to a Galectin-3 (LGALS3) polypeptide. In some embodiments, the LGALS3 polypeptide comprises SEQ ID NO: 12.

In one aspect, the present disclosure provides an antibody or an antigen binding fragment thereof, comprising a heavy chain immunoglobulin variable domain ($V_H$) and a light chain immunoglobulin variable domain ($V_L$), wherein (a) the $V_H$ comprises a $V_H$-CDR1 sequence selected from the group consisting of SEQ ID NOs: 7, 19, 29, 39, and 49, a $V_H$-CDR2 sequence selected from the group consisting of SEQ ID NOs: 8, 20, 30, 40, and 50, and a $V_H$-CDR3 sequence selected from the group consisting of SEQ ID NOs: 9, 21, 31, 41, and 51, and/or (b) the $V_L$ comprises a $V_L$-CDR1 sequence selected from the group consisting of SEQ ID NOs: 2, 14, 24 34, and 44, a $V_L$-CDR2 sequence selected from the group consisting of SEQ ID NOs: 3, 15, 25, 35, and 45, and a $V_L$-CDR3 sequence selected from the group consisting of SEQ ID NOs: 4, 16, 26, 36, and 46.

In one aspect, the present disclosure provides an antibody or an antigen-binding fragment thereof that specifically binds to a Galectin-3 (LGALS3), wherein the antibody or antigen-binding fragment thereof comprises a heavy chain variable region ($V_H$) and a light chain variable region ($V_L$), wherein: (a) the $V_H$ comprises a $V_H$ complementarity determining region (CDR)1 sequence comprising SEQ ID NO: 7, a $V_H$ CDR2 sequence comprising SEQ ID NO: 8, and a $V_H$ CDR3 sequence comprising SEQ ID NO: 9, and/or the $V_L$ comprises a $V_L$ CDR1 sequence comprising SEQ ID NO: 2, a $V_L$ CDR2 sequence comprising SEQ ID NO: 3, and a $V_L$ CDR3 sequence comprising SEQ ID NO: 4; (b) the $V_H$ comprises a $V_H$ complementarity determining region (CDR)1 sequence comprising SEQ ID NO: 19, a $V_H$ CDR2 sequence comprising SEQ ID NO: 20, and a $V_H$ CDR3 sequence comprising SEQ ID NO: 21, and/or the $V_L$ comprises a $V_L$ CDR1 sequence comprising SEQ ID NO: 14, a $V_L$ CDR2 sequence comprising SEQ ID NO: 15, and a $V_L$ CDR3 sequence comprising SEQ ID NO: 16; (c) the $V_H$ comprises a $V_H$ complementarity determining region (CDR)1 sequence comprising SEQ ID NO: 29, a $V_H$ CDR2 sequence comprising SEQ ID NO: 30, and a $V_H$ CDR3 sequence comprising SEQ ID NO: 31, and/or the $V_L$ comprises a $V_L$ CDR1 sequence comprising SEQ ID NO: 24, a $V_L$ CDR2 sequence comprising SEQ ID NO: 25, and a $V_L$ CDR3 sequence comprising SEQ ID NO: 26; (d) the $V_H$ comprises a $V_H$ complementarity determining region (CDR)1 sequence comprising SEQ ID NO: 39, a $V_H$ CDR2 sequence comprising SEQ ID NO: 40, and a $V_H$ CDR3 sequence comprising SEQ ID NO: 41, and/or the $V_L$ comprises a $V_L$ CDR1 sequence comprising SEQ ID NO: 34, a $V_L$ CDR2 sequence comprising SEQ ID NO: 35, and a $V_L$ CDR3 sequence comprising SEQ ID NO: 36; or (e) the $V_H$ comprises a $V_H$ complementarity determining region (CDR)1 sequence comprising SEQ ID NO: 49, a $V_H$ CDR2 sequence comprising SEQ ID NO: 50, and a $V_H$ CDR3 sequence comprising SEQ ID NO: 51, and/or the $V_L$ comprises a $V_L$ CDR1 sequence comprising SEQ ID NO: 44, a $V_L$ CDR2 sequence comprising SEQ ID NO: 45, and a $V_L$ CDR3 sequence comprising SEQ ID NO: 46. The antibody or antigen-binding fragment may comprise a human or humanized heavy chain variable domain ($V_H$) and/or a human or humanized a light chain variable domain ($V_L$). In some embodiments, the $V_H$ comprises an amino acid sequence selected from the group consisting of SEQ ID NO: 6, SEQ ID NO: 18, SEQ ID NO: 28, SEQ ID NO: 38, and SEQ ID NO: 48, and/or the $V_L$ comprises an amino acid sequence selected from the group consisting of SEQ ID NO: 1, SEQ ID NO: 13, SEQ ID NO: 23, SEQ ID NO: 33, and SEQ ID NO: 43. Additionally or alternatively, in some embodiments, wherein the antigen-binding fragment is a Fab, F(ab')$_2$, Fab', Fv or scFv.

Additionally or alternatively, in certain embodiments, the antibody or antigen-binding fragment comprises a $V_H$ amino acid sequence and a $V_L$ amino acid sequence selected from the group consisting of SEQ ID NO: 6 and SEQ ID NO: 1, SEQ ID NO: 18 and SEQ ID NO: 13, SEQ ID NO: 28 and SEQ ID NO: 23, SEQ ID NO: 38 and SEQ ID NO: 33, and SEQ ID NO: 48 and SEQ ID NO: 43, respectively. In some embodiments, the antibody or antigen-binding fragment is a humanized or fully human antibody or antigen-binding fragment thereof.

In any of the preceding embodiments, the antibody comprises human-derived heavy and light chain constant regions. In certain embodiments of the antibodies of the present technology, the heavy chain constant region has an isotype selected from the group consisting of gamma 1, gamma 2, gamma 3, and gamma 4, and/or the light chain constant region has an isotype selected from the group consisting of kappa and lambda. Additionally or alternatively, in some embodiments, the antibody is an immunoglobulin comprising two identical heavy chains and two identical light chains. In certain embodiments, the immunoglobulin is an IgG. In some embodiments, the antibody is a monoclonal antibody, a single chain antibody, or any composition comprising an antigen-binding fragment thereof. Additionally or alternatively, in some embodiments, the antibody or antigen-binding fragment thereof is generated by immunizing a transgenic mouse.

In some embodiments, the antibody or antigen-binding fragment of the present technology inhibits Gal-3-PE binding to tumors cells. In certain embodiments, the tumor cells are ovarian tumor cells (e.g., OVCAR3 cells). Additionally or alternatively, in some embodiments, the antibody or antigen-binding fragment thereof inhibits binding of LGALS3 to a glycosylated cell surface protein (e.g., a glycosylated cell surface receptor). In certain embodiments, the antibody or antigen-binding fragment inhibits binding of LGALS3 to one or more of glycosylated mucin-1 (MUC1), mucin-4 (MUC4), mucin-16 (MUC16), a disialoganglioside, GD2, epidermal growth factor receptor (EGFR), platelet-derived growth factor receptor (PDGFR), insulin-like growth factor receptor (IGFR), cMET/hepatocyte growth factor receptor (HGFR), an integrin or CTLA4. In some embodiments, the glycosylated MUC16 is N-glycosylated at Asn1800 or Asn1806. In any and all embodiments of the antibody or antigen-binding fragment disclosed herein, the antibody or antigen-binding fragment inhibits growth of a tumor that expresses a glycosylated form of MUC16.

In one aspect, the present disclosure provides an antibody conjugate comprising an agent conjugated to any of the antibodies or antigen-binding fragments described herein. The agent may be an imaging agent or a cytotoxic agent. In some embodiments, the antibody or antigen-binding fragment is a bispecific antibody. In certain embodiments, the bispecific antibody specifically binds CD3. Additionally or alternatively, in some embodiments, the bispecific antibody comprises an immunoglobulin that specifically binds LGALS3, wherein the light chain of the immunoglobulin is conjugated via a peptide linker to a single chain variable fragment (scFv) that specifically binds to CD3.

In another aspect, the present disclosure provides a bispecific antibody conjugate comprising an agent conjugated to any of the bispecific antibodies or antigen binding fragments described herein. The agent may be an imaging agent or a cytotoxic agent.

Also disclosed herein are scFv conjugates comprising an agent conjugated to any of the scFvs described herein. The agent may be an imaging agent or a cytotoxic agent. Also provided herein are chimeric antigen receptors (CAR) comprising any of the antibodies or antigen-binding fragments (e.g., scFvs) described herein, as well as T-cells that recombinantly expresses said CARs.

In one aspect, the present disclosure provides a recombinant nucleic acid sequence encoding any of the antibodies or antigen binding fragments or CARs described herein. In some embodiments, the recombinant nucleic acid sequence comprises the polynucleotide of any one of SEQ ID NO: 5, SEQ ID NO: 17, SEQ ID NO: 27, SEQ ID NO: 37, SEQ ID NO: 47, SEQ ID NO: 10, SEQ ID NO: 22, SEQ ID NO: 32, SEQ ID NO: 42, or SEQ ID NO: 52, or a portion thereof encoding at least one CDR sequence.

In another aspect, the present disclosure provides a vector comprising any of the recombinant nucleic acid sequences disclosed herein. In some embodiments, the recombinant nucleic acid sequence is operably linked to a promoter. In yet another aspect, the present disclosure provides an isolated cell comprising any of the recombinant nucleic acid sequences or vectors disclosed herein.

In one aspect, the present disclosure provides a pharmaceutical composition comprising a therapeutically effective amount of any of the antibodies, antigen-binding fragments, antibody conjugates, bispecific antibodies or antibody conjugates, scFvs, scFv conjugates, CARs, T cells, recombinant nucleic acid sequences, vectors, or isolated cells described herein, and a pharmaceutically acceptable carrier.

In another aspect, the present disclosure provides a method of treating cancer in a patient in need thereof, comprising administering to said patient an effective amount of any pharmaceutical composition disclosed herein. The cancer may be a cancer of the ovary, lung, pancreas, breast, uterine, fallopian tube, or primary peritoneum, and/or a metastatic cancer. In some embodiments, the pharmaceutical composition inhibits metastasis in the patient. Additionally or alternatively, in some embodiments, the method further comprises administering a therapeutically effective amount of an additional therapeutic agent to the patient. In certain embodiments, the patient is a human patient.

In yet another aspect, the present disclosure provides a method for detecting LGALS3 protein expression levels in a biological sample comprising contacting the biological sample with any of the antibodies or antigen binding fragments disclosed herein, and detecting binding to LGALS3 protein in the biological sample.

Also disclosed herein are kits for the detection and/or treatment of a Galectin-3-associated disease or condition (e.g., Galectin-3-associated cancers, cardiovascular disease, fibrosis, and inflammation) comprising at least one immunoglobulin-related composition of the present technology (e.g., any of the antibodies, antigen-binding fragments, antibody conjugates, bispecific antibodies or antibody conjugates, scFvs, scFv conjugates, CARs, T cells, recombinant nucleic acid sequences, vectors, or isolated cells described herein described herein), and instructions for use. In certain embodiments, the immunoglobulin-related composition is coupled to one or more detectable labels. In one embodiment, the one or more detectable labels comprise a radioactive label, a fluorescent label, or a chromogenic label. Additionally or alternatively, in some embodiments, the kit further comprises a secondary antibody that specifically binds to an immunoglobulin-related composition described herein. In some embodiments, the secondary antibody is coupled to at least one detectable label selected from the group consisting of a radioactive label, a fluorescent label, or a chromogenic label.

BRIEF DESCRIPTION OF THE DRAWINGS

FIG. 2A illustrates the in vitro and in vivo experimental functions of Galectin 3 and potential blocking antibody effects for treatment with the antibodies provided. FIG. 2B discloses SEQ ID NO: 58.

FIG. 3A shows the binding of the indicated concentrations of PE labeled Gal-3 (Gal-3-PE) to the indicated number of OVCAR3 cells. The numbers of OVCAR3 cells bound to Gal-3-PE as detected by a Mirrorball® flow cytometer are plotted. FIG. 3B shows the binding of the indicated concentrations of PE labeled Gal-3protein (Gal-3-PE) to the indicated number of MOLT-4 cells. The numbers of MOLT-4 cells bound to Gal-3-PE as detected by a Mirrorball® flow cytometer are plotted.

FIGS. 5A-5B demonstrate the species cross-reactivity of the indicated antibodies. Binding to mouse Gal-3 (FIG. 5A) or human Gal-3 (FIG. 5B) was detected using ELISA. $OD_{450}$ values for each clone are shown. As shown, clones 39F02, 38E05 and 46H02, but not clones 20F08 and 12H07, bound mouse Gal-3.

FIG. 9A shows the premix epitope binning assay strategy used herein. In this strategy, the test antibody (analyte) is immobilized on the surface and a ligand is flowed over the analyte and binding is detected by SPR. The ligand was the antigen alone or a premixed solution of the antigen complexed with a second antibody. A premixed solution of the antigen complexed with the test antibody (analyte) was used as a positive control indicating a blocking reaction. As shown, the antigen alone produces a characteristic SPR profile (left panel) indicating binding of the analyte to the antigen. When the ligand is a premixed solution of the antigen complexed with a second antibody, if the second antibody binds to a distinct epitope on the antigen, a SPR profile indicating binding of the analyte to the antigen is obtained (middle panel). The SPR profile of the positive control shows no binding indicating that the antigen complexed with the test antibody (analyte) blocks binding of the analyte (right panel). FIG. 9B shows the premix epitope binning assay using mAb 2D3 as analyte and Gal-3, Gal-3+2D3 complex or Gal-3+46H02 complex as ligands. FIG. 9C shows the premix epitope binning assay using mAb 46H02 as analyte and Gal-3, Gal-3+2D3 complex or Gal-3+46H02 complex as ligands. These data show that mAbs 46H02 and 14D11 do not compete with each other and therefore, bind to separate epitopes.

DETAILED DESCRIPTION

Figure 1A:
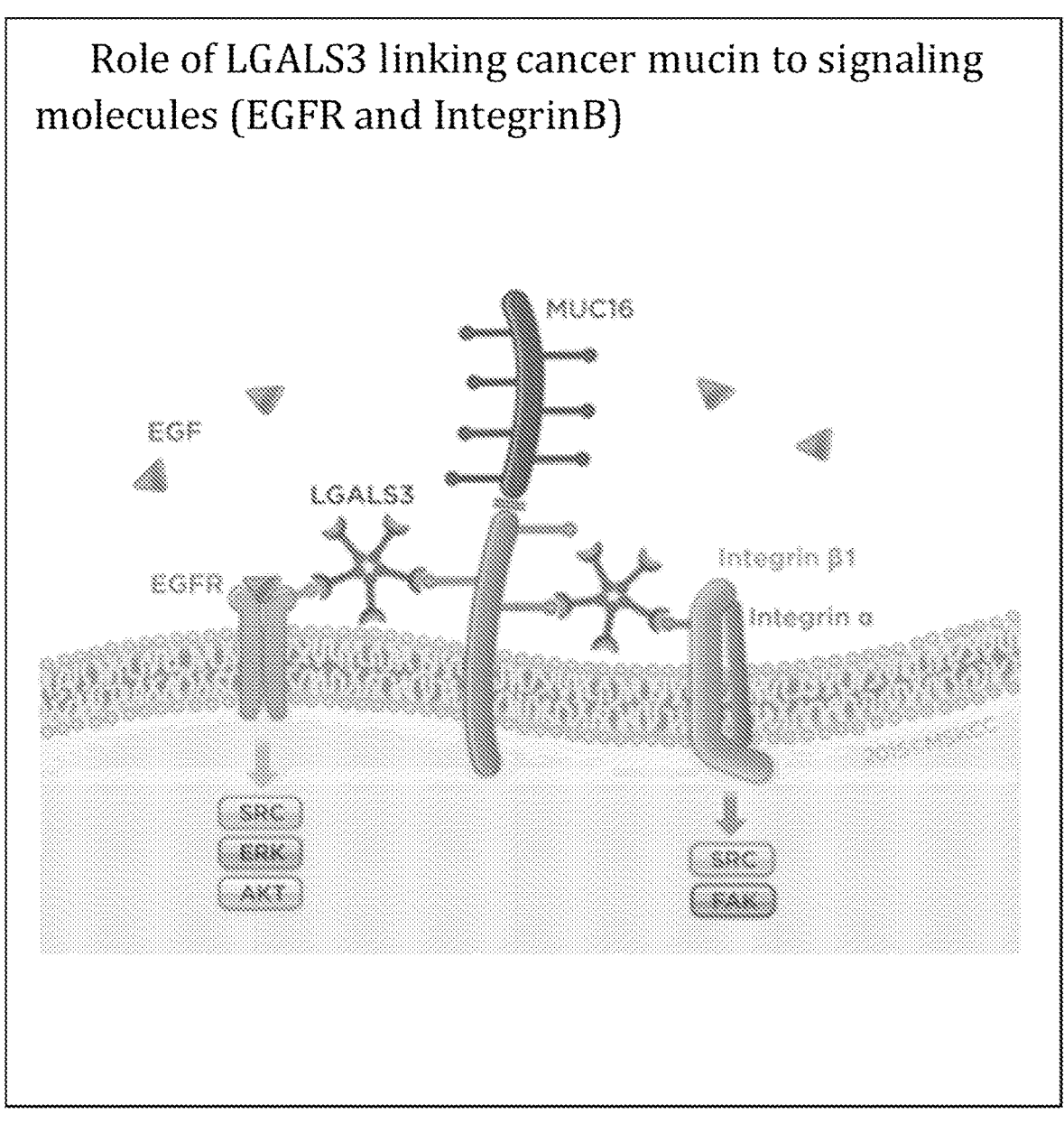
FIG. 1A illustrates the structure and activity of extracellular Galectin-3 (LGALS3) which forms a pentamer to link cell surface cancer molecules, such as MUC16 in ovarian cancer, to signaling molecules via contact with signaling receptor, such as EGFR and Integrins. Activation of downstream signaling molecules, such as SRC, ERK, AKT, and FAK in turn drives the production of key molecules for metastasis and invasion.
Figure 1B:
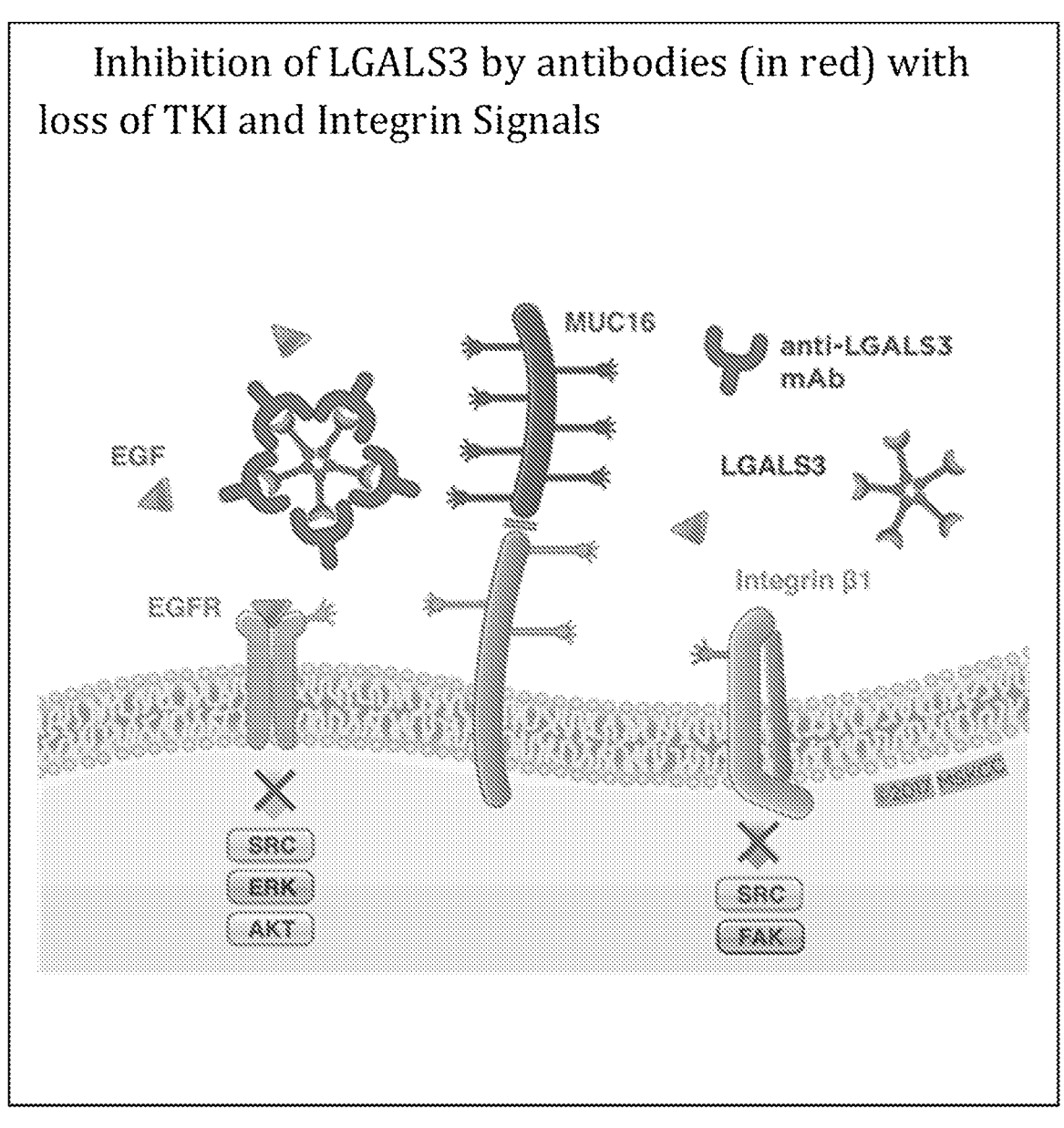
FIG. 1B illustrates how antibody inhibitors that bind to the LGALS3 carbohydrate binding domain will block activation of "outside-in" signal transduction by disrupting the LGALS3 surface complexes and destabilizing the cell surface receptors.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Definitions

Unless defined otherwise, all technical and scientific terms used herein have the meaning commonly understood by a person skilled in the art to which this disclosure belongs. The following references provide one of skill with a general definition of many of the terms used in the present technology: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the singular forms "a", "an" and "the" are intended to include the plural forms as well, unless the context clearly indicates otherwise.

As used herein, the terms "about" when used to modify a numeric value or numeric range, indicate that deviations of 5% to 10% above and 5% to 10% below the value or range remain within the intended meaning of the recited value or range.

As used herein, the term "administration" of an agent to a subject includes any route of introducing or delivering the agent to a subject to perform its intended function. Administration can be carried out by any suitable route, including, but not limited to, intravenously, intramuscularly, intraperitoneally, subcutaneously, and other suitable routes as described herein. Administration includes self-administration and the administration by another.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "effective amount" or "therapeutically effective amount" refers to a quantity of an agent sufficient to achieve a desired therapeutic effect. In the context of therapeutic applications, the amount of a therapeutic peptide administered to the subject can depend on the type and severity of the infection and on the characteristics of the individual, such as general health, age, sex, body weight and tolerance to drugs. It can also depend on the degree, severity and type of disease. The skilled artisan will be able to determine appropriate dosages depending on these and other factors.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983)). The antibodies of the present technology comprise whole native antibodies, monoclonal antibodies, human antibodies, humanized antibodies, camelised antibodies, multispecific antibodies, bispecific antibodies, chimeric antibodies, Fab, Fab', single chain V region fragments (scFv), single domain antibodies (e.g., nanobodies and single domain camelid antibodies), VNAR fragments, Bi-specific T-cell engager (BiTE) antibodies, minibodies, disulfide-linked Fvs (dsFv), and anti-idiotypic (anti-Id) antibodies, intrabodies, fusion polypeptides, unconventional antibodies and antigen-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system. As used herein interchangeably, the terms "antigen-binding portion", "antigen-binding fragment", or "antigen-binding region" of an antibody, refer to the region or portion of an antibody that binds to the antigen and which confers antigen specificity to the antibody; fragments of antigen-binding proteins, for example, antibodies include one or more fragments of an antibody that retain the ability to specifically bind to an antigen (e.g., a peptide/HLA complex). It has been shown that the antigen-binding function of an antibody can be performed by fragments of a full-length antibody. Examples of antigen-binding portions encompassed within the term "antibody fragments" of an antibody include a Fab fragment, a monovalent fragment consisting of the $V_L$, $V_H$, $C_L$ and CHI domains; a F(ab)$_2$ fragment, a bivalent fragment comprising two Fab fragments linked by a disulfide bridge at the hinge region; a Fd fragment consisting of the $V_H$ and CHI domains; a Fv fragment consisting of the $V_L$ and $V_H$ domains of a single arm of an antibody; a dAb fragment (Ward et al., *Nature* 341: 544-546 (1989)), which consists of a $V_H$ domain; and an isolated complementarity determining region (CDR).

Antibodies and antibody fragments can be wholly or partially derived from mammals (e.g., humans, non-human primates, goats, guinea pigs, hamsters, horses, mice, rats, rabbits and sheep) or non-mammalian antibody producing animals (e.g., chickens, ducks, geese, snakes, urodele amphibians). The antibodies and antibody fragments can be produced in animals or produced outside of animals, such as from yeast or phage (e.g., as a single antibody or antibody fragment or as part of an antibody library).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., *Science* 242:423-426 (1988); and Huston et al., *Proc. Natl. Acad. Sci.* 85: 5879-5883 (1988). These antibody fragments are obtained using conventional techniques known to those of ordinary skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$:$V_L$ heterodimer. The heavy ($V_H$) and light chains ($V_L$) are either joined directly or joined by a peptide-encoding linker (e.g., about 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain.

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (*Proc. Nat. Acad. Sci. USA*, 85:5879-5883 (1988)). See, also, U.S. Pat. Nos. 5,132,405 and 4,956,778; and U.S. Patent Publication Nos. 20050196754 and 20050196754. Antagonistic scFvs having inhibitory activity have been described (see, e.g., Zhao et al., *Hybridoma* (Larchmt) 27(6):455-51 (2008); Peter et al., *J Cachexia Sarcopenia Muscle* (2012); Shieh et al., *J Imunol* 183(4):2277-85 (2009); Giomarelli et al., *Thromb Haemost* 97(6):955-63 (2007); Fife eta., *J Clin Invst* 116(8):2252-61 (2006); Brocks et al., *Immunotechnology* 3(3): 173-84 (1997); Moosmayer et al., *Ther Immunol* 2(10):31-40 (1995) Agonistic scFvs having stimulatory activity have been described (see, e.g., Peter et al., *J Biol Chem* 25278(38):36740-7 (2003); Xie et al., *Nat Biotech* 15(8):768-71 (1997); Ledbetter et al., *Crit Rev Immunol* 17 (5-6):427-55 (1997); Ho et al., *Bio Chim Biophys Acta* 1638(3):257-66 (2003)).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')₂" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')₂" fragment can be split into two individual Fab' fragments.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. Sequences of Proteins of Immunological Interest, Fifth Edition, U.S. Department of Health and Human Services, NIH Publication No. 91-3242(1991)).

As used herein, the term "constant region" or "constant domain" is interchangeable and has its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, an "epitope" is a term in the art and can refer to a localized region of an antigen to which an antibody can specifically bind. An epitope can be, e.g., contiguous amino acids of a polypeptide (linear or contiguous epitope) or an epitope can, e.g., come together from two or more noncontiguous regions of a polypeptide or polypeptides (conformational, non-linear, discontinuous, or non-contiguous epitope).

As used herein, the term "ligand" refers to a molecule that binds to a receptor. In some embodiments, the ligand binds a receptor on another cell, allowing for cell-to-cell recognition and/or interaction.

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes (e.g., either monovalent or multivalent). Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay). Nucleic acid molecules useful in the presently disclosed subject matter include any nucleic acid molecule that encodes a polypeptide or a fragment thereof. In certain embodiments, nucleic acid molecules useful in the presently disclosed subject matter include nucleic acid molecules that encode an antibody or an antigen-binding portion thereof. Such nucleic acid molecules need not be 100% identical with an endogenous nucleic acid sequence, but will typically exhibit substantial identity. Polynucleotides having "substantial homology" or "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger, *Methods Enzymol.* 152:399 (1987); Kimmel, A. R. *Methods Enzymol.* 152:507 (1987)).

As used herein, the terms "specifically binds," and "specifically recognizes" are analogous terms in the context of antibodies and refer to antibodies and antigen-binding fragments thereof that bind to an antigen (e.g., epitope or immune complex) via the antigen-binding sites as understood by one skilled in the art, and does not exclude cross-reactivity of the antibody or antigen-binding fragment with other antigens.

The terms "substantially homologous" or "substantially identical" mean a polypeptide or nucleic acid molecule that exhibits at least 50% or greater homology or identity to a reference amino acid sequence (for example, any one of the amino acid sequences described herein) or nucleic acid sequence (for example, any one of the nucleic acid sequences described herein). For example, such a sequence is at least about 60%, about 65%, about 70%, about 75%, about 80%, about 85%, about 90%, about 95% or about 99% homologous or identical at the amino acid level or nucleic acid to the sequence used for comparison (e.g., a wild-type, or native, sequence). In some embodiments, a substantially homologous or substantially identical polypeptide contains one or more amino acid amino acid substitutions, insertions, or deletions relative to the sequence used for comparison. In some embodiments, a substantially homologous or substantially identical polypeptide contains one or more non-natural amino acids or amino acid analogs, including, D-amino acids and retroinverso amino, to replace homologous sequences.

Sequence homology or sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $e^{-100}$ indicating a closely related sequence.

As used herein, the term "analog" refers to a structurally related polypeptide or nucleic acid molecule having the function of a reference polypeptide or nucleic acid molecule.

As used herein, the term "a conservative sequence modification" refers to an amino acid modification that does not significantly affect or alter the binding characteristics of the presently disclosed anti-LGALS3 antibody or an antigen-binding fragment thereof comprising the amino acid sequence. Conservative modifications can include amino acid substitutions, additions and deletions. Modifications can be introduced into the human scFv of the presently disclosed anti-LGALS3 antibody or an antigen-binding fragment thereof by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (l) above) using the functional assays described herein. In certain embodiments, no more than one, no more than two, no more than three, no more than four, no more than five residues within a specified sequence or a CDR region are altered.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%), 1%), 0.5%), or 0.1%) of other material, e.g., cellular material, culture medium, other nucleic acid molecules, chemical precursors and/or other chemicals.

As used herein, the term "isolated cell" refers to a cell that is separated from the molecular and/or cellular components that naturally accompany the cell.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease (e.g., a neoplasia), or otherwise reduce the pathological consequences of the disease (e.g., a neoplasia). The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the engineered immune cells administered.

As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasia can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasia include cancers, such as sarcomas, carcinomas, or plasmacytomas (malignant tumor of the plasma cells).

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

Overview

Galectin-3 (LGALS3) is a β-galactoside-binding protein that is secreted from many cells although the protein lacks a signal sequence for transfer into the endoplasmic reticulum and Golgi compartments and entry into classical secretory pathways. LGALS3 is found in cellular and extracellular locations of the cell and has pleiotropic biological functions such as cell growth, cell adhesion and cell-cell interaction. It may exhibit anti or pro-apoptotic activity depending on its localization and post-translational modifications, such as cleavage and phosphorylation. Cleavage of galectin-3 was reported to be involved with angiogenic potential and apoptotic resistance. Phosphorylation of galectin-3 regulates its sugar-binding ability.

Preliminary studies by the inventors in ovarian cancer using an artificially synthesized chimeric LGALS3 have established that LGALS3 plays an essential role of the growth, spread and invasive properties of ovarian cancer (Rao, et al. (2017) *ACS Chem. Biol.* 12 (8): 2085-2096, which is incorporated by reference in its entirety). This work utilized both knockdown shRNA suppression of LGALS3 and chimeric antibodies in which the native, low affinity LGALS3 carbohydrate binding domain replaced the antibody variable region. In knockdown experiments, it was shown that tumor expression of LGALS3 is required for the oncogene activating effects of the ovarian cancer mucin MUC16/CA125. When LGALS3 knockdown cells were transplanted in nude mice, they had very limited growth, confirming the essential role of LGALS3 for in vivo tumor growth. It was further demonstrated that growth/invasion enhancement by LGALS3 is extracellular. In invasion studies, it was shown that Matrigel invasion of ovarian cancer cells is dependent on LGALS3. Low affinity chimeric antibodies comprising a fusion protein of the unmodified carbohydrate binding domain of LGALS3 linked to an Fc backbone, can block LGALS3 function and prevent Matrigel gel invasion while chimeric blocking antibodies for Galectin-1 were ineffective. In addition, introduction of the low affinity, chimeric anti-LGALS3 blocking antibodies reduce in vivo growth of xenografts in mice. These chimeric antibodies had no notable adverse effects on the host mice, consistent with the reported minimal effect of LGALS3 knockouts (Wright et al., (2017) *J Leukoc Biol* 101(3): 717-726.

Figure 2B:
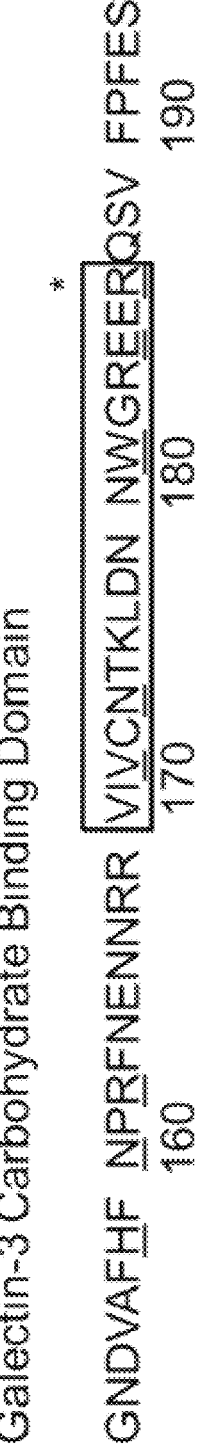
FIG. 2B illustrates the primary structure of the LGALS3 carbohydrate binding domain (CBD). The LGALS3 CBD is divided into 5 sub-domains, each binding to a single sugar residue and, conventionally labeled as A B C D and E. In the figure, the highly conserved amino acids are underlined while domains C, D and E are shown in the boxed area. R186(*) in particular is important to the functions of LGALS3. The LGALS3 CBD sequence is highly homologous to the murine Galectin 3 but differs from GAL1, GALT and GALS. While each of these family members have similar sugar binding domains, LGALS3 is the only lectin with the polymerization domain.

Described herein is an immunization strategy to isolate inhibitory, high affinity antibodies to LGALS3. The primary sequence of the LGALS3 carbohydrate binding domain (CBD) is illustrated in FIG. 2B. The box depicts C, D and E domains of the CBD, which are important for lactosamine binding. The highly conserved amino acids are underlined. R186(*) is important to the functions of GAL3. The GAL3 CBD sequence is highly homologous to the murine Galectin-3 but differs from GAL1, GALT and GALS. While each of these family members have similar sugar binding domains, LGALS3 is the only lectin with the polymerization domain. As described in the examples herein, in order to generate antibodies to the LGALS3 CBD, mice were immunized with peptides and/or fusion constructs containing the LGALS3, or portions thereof comprising the amino acid sequence of SEQ ID NO: 53. Anti-LGALS3 antibodies were screened using peptides and/or fusion constructs containing the LGALS3, or portions thereof. The isolated antibodies bind to native human LGALS3 and the mouse homolog Lgal3.

Figure 4:
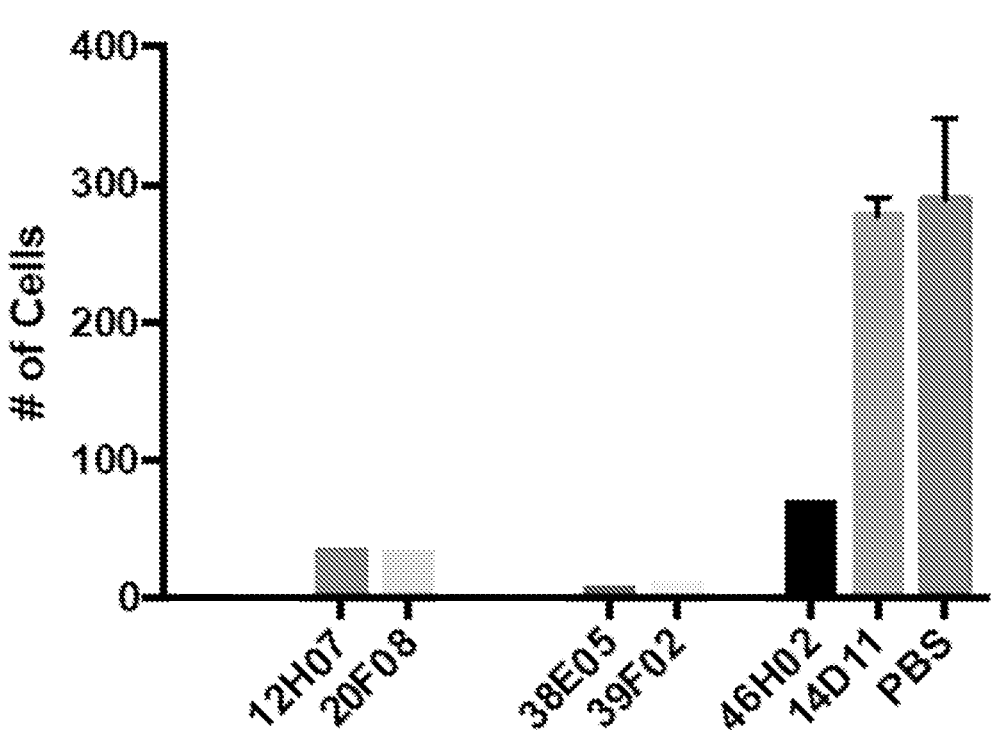
FIG. 4 shows the exemplary results of a secondary functional screen to select the antibodies that inhibit the binding of Gal-3-PE binding to OVCAR3 cells. Reactions to measure binding of Gal-3-PE to OVCAR3 cells were set up in the presence of PBS (negative control), or the indicated antibody, obtained by enrichment (crude purification of antibodies) from the supernatants of the hybridoma clones selected in a primary binding screen. The extent of binding, as measured by a Mirrorball® laser scanning flow cytometer, was plotted. The secondary screen showed that five antibodies blocked binding of Gal-3-PE to OVCAR3 cells after. Clone 14D11 did not block Gal-3-PE binding to OVCAR3 cells in this assay.
Figure 8:
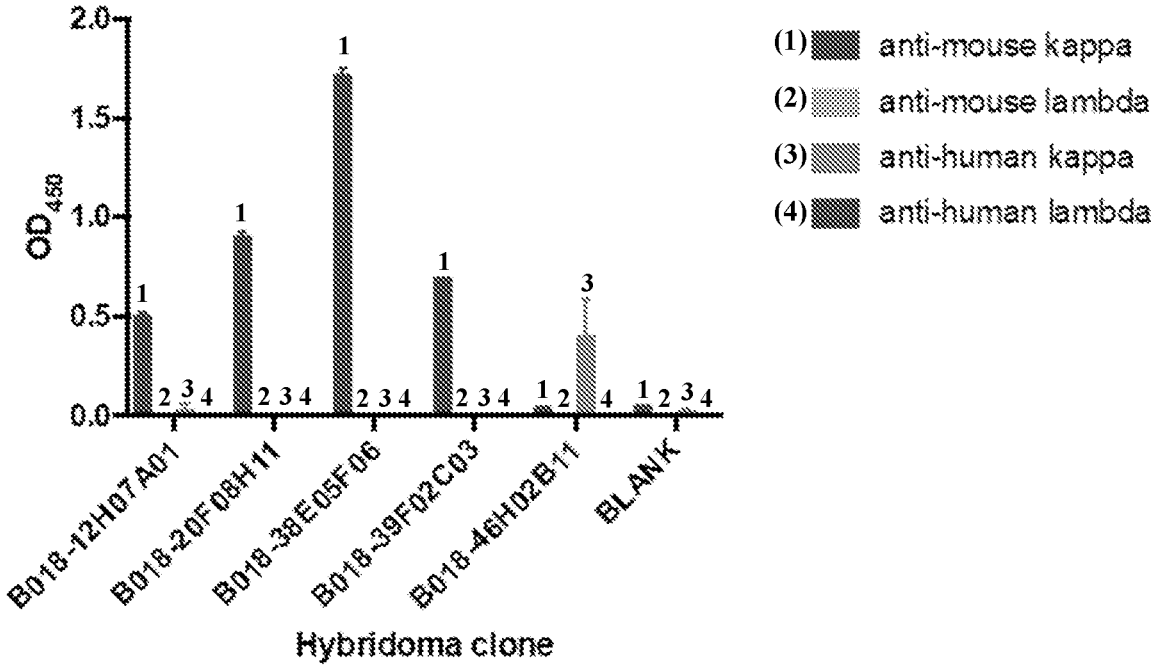
FIG. 8 shows the light chain species determination of the indicated antibodies. The species of the light chains of the indicated mAbs was determined by ELISA using anti-mouse kappa, anti-mouse lambda, anti-human kappa, and anti-human lambda antibodies. The data showed that 46H02 has fully human $F(ab)_2$, whereas the other hits have human HC and murine LC.

In an exemplary embodiment, the anti-Gal3 antibodies are generated using genetically modified animals that express chimeric antibody genes. For example, in an exemplary embodiment, the anti-Gal3 antibodies provided herein are generated using AlivaMab® Mouse Kappa mice and/or AlivaMab® Mouse Lambda mice (also referred to herein interchangeably as AlivaMab® Kappa Mice and AlivaMab® Lambda Mice, respectively). Antibodies produced by AlivaMab® Kappa Mice comprise a chimeric immunoglobulin heavy (IgH) chain and a human immunoglobulin kappa (κ) light chain. Antibodies produced by AlivaMab® Lambda Mice comprise a chimeric IgH chain and a human immunoglobulin lambda PO light chain. The chimeric IgH chain of the AlivaMab® Mouse antibodies comprises a human variable region comprising a human variable heavy ($V_H$) domain, a human diversity heavy (DH) domain, and a human joining heavy (JH) domain, a human constant heavy 1 (CH1) domain, a human upper hinge region (except for Cμ, which is naturally missing an upper hinge region), a mouse middle hinge region, a mouse CH2 domain, and a mouse CH3 domain. In an exemplary embodiment, as shown in FIG. 8, the AlivaMab® Mouse produces a mixture of (1) antibodies comprising fully human variable heavy domain ($V_H$) and human light chain domain ($V_L$), and (2) antibodies comprising a mixture of human variable heavy chain domain ($V_H$) and mouse light chain domain ($V_L$). In an exemplary embodiment, identification of hits, e.g., an anti-Gal3 antibody is carried out using ELISA. In an exemplary embodiment, identification of enriched clones is carried out using an assay to measure inhibition of Gal-3-PE binding to OVCAR3 (FIG. 4). In an exemplary embodiment, identification of antibodies comprising fully human variable heavy domain ($V_H$) and human light chain domain ($V_L$) is carried out using ELISA. In further exemplary embodiments, the $V_H$ and/or $V_L$ regions of the antibodies identified from the AlivaMab® Mouse are used to create additional constructs as described herein. In further exemplary embodiments, the CDRs of the $V_H$ and/or $V_L$ regions identified from the AlivaMab® Mouse are used to create additional constructs as described herein.

A variety of studies have demonstrated a role for LGALS3 in tumor biology and inflammation. A partial list of effects and the anticipated result of LGALS3 targeting are shown in FIG. 2A. Many of the anticipated effects are expected to be beneficial in a cancer treatment. Although the effects of LGALS3 are protean, even complete loss of LGALS3 in a knockout mouse model is consistent with nearly normal development, and some immunosuppressive effects are not substantially different than TNF inhibitors. Based on these studies, the antibodies provided herein are expected to be useful therapeutics for the treatment of a LGALS3-mediated diseases and conditions, including but not limited to cancer and inflammation.

Provided are antibodies and antigen-binding fragments thereof, and polypeptides including such antibodies or fragments, such as fusion proteins, conjugates, and/or chimeric antigen receptors, as well as cells expressing the same. Among the antibodies and fragments are those that specifically bind to epitopes of a LGALS3 protein. Such antibodies are referred to herein as "anti-LGALS3 antibodies."

In some embodiments, the anti-LGALS3 antibodies and antigen-binding fragments thereof described herein inhibit or treat cancer. In some embodiments, the anti-LGALS3 antibodies and antigen-binding fragments thereof described herein inhibit invasion and growth of tumor cells. In some embodiments, the anti-LGALS3 antibodies and antigen-binding fragments thereof described herein inhibit tumor angiogenesis. In some embodiments, the anti-LGALS3 antibodies and antigen-binding fragments thereof described herein inhibit metastasis. In some embodiments, the anti-LGALS3 antibodies and antigen-binding fragments thereof described herein inhibit growth of a metastatic tumor. In some embodiments, the anti-LGALS3 antibodies and antigen-binding fragments thereof described herein inhibit activation of cancer-related signaling molecules, such as AKT or ERK.

In some embodiments, the anti-LGALS3 antibodies and antigen-binding fragments thereof described herein inhibit induction of T-cell apoptosis by LGALS3.

In some embodiments, the anti-LGALS3 antibodies and antigen-binding fragments thereof described herein inhibit immunosuppression of T-cells.

In some embodiments, the anti-LGALS3 antibodies and antigen-binding fragments thereof described herein inhibit or treat cardiovascular disease. In some embodiments, the anti-LGALS3 antibodies and antigen-binding fragments thereof described herein inhibit or treat heart failure, coronary heart disease or myocardial infarction.

In some embodiments, the anti-LGALS3 antibodies and antigen-binding fragments thereof described herein inhibit or treat pulmonary fibrosis.

In some embodiments, the anti-LGALS3 antibodies and antigen-binding fragments thereof described herein inhibit or treat renal disease. In some embodiments, the anti-LGALS3 antibodies and antigen-binding fragments thereof described herein inhibit or treat glomerulonephritis. In some embodiments, the anti-LGALS3 antibodies and antigen-binding fragments thereof described herein inhibit or treat renal cell carcinoma.

Also provided herein are polynucleotides (e.g., isolated polynucleotides) comprising nucleic acid sequences (e.g., complementary DNA (cDNA)), encoding such antibodies, and antigen-binding fragments thereof, heavy chains, or light chains. Further provided are vectors (e.g., expression vectors) and cells (e.g., isolated cells or ex vivo cells) comprising polynucleotides (e.g., isolated polynucleotides) comprising nucleic acid sequences (e.g., complementary DNA (cDNA)), encoding such antibodies, and antigen-binding fragments thereof, heavy chains, or light chains.

Also provided are methods of making such antibodies, antigen-binding fragments thereof, heavy chains, light chains, vectors, and cells. In other aspects, provided herein are methods and uses for anti-LGALS3 antibodies for treating or managing certain conditions or disorders described herein, such as treating or managing cancer. Related compositions (e.g., pharmaceutical compositions), kits, and diagnostic methods are also provided.

As used herein, the term "LGALS3," "LGALS3 polypeptide," "LGALS3 peptide" "Gal-3," "Gal-3 polypeptide," or "Gal-3 peptide" are used interchangeable herein to refer to Galectin-3 and functional homologs and fragments thereof that bind to β-galactosides. GenBank™ accession number NM_002306.4 (SEQ ID NO: 11) provides an exemplary human LGALS3 nucleic acid sequence. GenBank™ accession number NP 002297.2 (SEQ ID NO: 12) provides an exemplary human LGALS3 amino acid sequence.

Anti-LGALS3 Antibodies

Anti-LGALS3 antibodies or antigen-binding fragments thereof can include, e.g., monoclonal antibodies, polyclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, single domain antibodies, monovalent antibodies, single chain antibodies or single-chain variable fragments (scFv), camelid antibodies, affibodies, and disulfide-linked Fvs (dsFv), or fragments thereof. Such antibodies can be made by methods known in the art.

A multispecific antibody or fragment thereof refers to an antibody or fragment thereof that can bind simultaneously to at least two targets that are of different structure, e.g., two different antigens, two different epitopes on the same antigen, or a hapten and an antigen or epitope. One specificity could be for, for example, a B-cell, T-cell, myeloid-, plasma-, or mast-cell antigen or epitope, such as, for example CD3. Another specificity could be to a different antigen on the same or different cell type, such as for example, LGALS3. Multispecific, multivalent antibodies are constructs that have more than one binding site, and the binding sites are of different specificity, for example, a bispecific diabody, where one binding site reacts with one antigen and the other with another antigen.

A bispecific antibody is an antibody that can bind simultaneously to two targets which are of different structure. Bispecific antibodies (bsAb) and bispecific antibody fragments (bsFab) have at least one arm that specifically binds to a first target, for example, LGALS3, and at least one other arm that specifically binds to a second target, such as, for example, CD3. A variety of bispecific fusion proteins can be produced using molecular engineering. In one form, the bispecific fusion protein is divalent, consisting of, for example, (i) a scFv with a single binding site for one antigen and (ii) an antibody or a Fab fragment with a single binding site for a second antigen. In another form, the bispecific fusion protein is tetravalent, consisting of, for example, an IgG with two binding sites for one antigen and two identical scFv for a second antigen. See, for example, International Publication No. WO 2011/1160119, which is incorporated by reference in its entirety herein.

Recent methods for producing bispecific monoclonal antibodies include the use of engineered recombinant monoclonal antibodies which have additional cysteine residues so that they crosslink more strongly than the more common immunoglobulin isotypes. See, e.g., FitzGerald et al., Protein Eng. 10(10): 1221-1225, 1997. Another approach is to engineer recombinant fusion proteins linking two or more different single-chain antibody or antibody fragment segments with the needed dual specificities. See, e.g., Coloma et al., Nature Biotech. 15: 159-163, 1997. A variety of bispecific fusion proteins can be produced using molecular engineering.

Bispecific fusion proteins linking two or more different single-chain antibodies or antibody fragments can be produced in similar manner. Recombinant methods can be used to produce a variety of fusion proteins. In certain aspects, a flexible linker connects an scFv (e.g., an scFv targeting CD3) to the constant region of the light chain of a monoclonal antibody (e.g., an anti-LGALS3 antibody described herein). Appropriate linker sequences necessary for the in-frame connection of the heavy chain Fc to the scFv are introduced into the $V_L$ and Vkappa domains through PCR reactions. The DNA fragment encoding the scFv is then ligated into a staging vector containing a DNA sequence encoding the CHI domain. The resulting construct is excised and ligated into a vector containing a DNA sequence encoding the $V_H$ region of the antibody (e.g., the anti-LGALS3 antibody). The resulting vector can be used to transfect an appropriate host cell, such as a mammalian cell for the expression of the bispecific fusion protein.

The anti-LGALS3 antibodies described herein and fragments thereof in certain embodiments can also be used to prepare functional bispecific single-chain antibodies (bscAb), also called diabodies, and can be produced in mammalian cells using recombinant methods. See, e.g., Mack et al., *Proc. Natl. Acad. Sci. U.S.A.*, 92: 7021-7025, 1995, incorporated herein by reference. For example, bscAb can be produced by joining two single-chain Fv fragments via a glycine-serine linker using recombinant methods. The $V_L$ and $V_H$ domains of two antibodies of interest are isolated using standard PCR methods known in the art. Bispecific single-chain antibodies and bispecific fusion proteins are included within the scope of the present technology.

In certain embodiments, anti-LGALS3 antibodies or antigen-binding fragments thereof described herein refer to scFvs. A scFv is an art-recognized term. An scFv comprises a fusion protein of the variable regions of the heavy (VH) and light (VL) chains of an immunoglobulin, wherein the fusion protein retains the same antigen specificity as the whole immunoglobulin. The $V_H$ is fused to the $V_L$ via a peptide linker. In certain embodiments, the peptide linker is between 5 and 25, 5 and 15, 10 and 20, 10 and 15, or 15 and 25 amino acid residues in length. In certain embodiments, the scFv peptide linker displays one or more characteristics suitable for a peptide linker known to one of ordinary skill in the art. In certain embodiments, the scFv peptide linker comprises amino acids that allow for scFv peptide linker solubility, such as, for example, serine and threonine. In certain embodiments, the scFv peptide linker comprises amino acids that allow for scFv peptide linker flexibility, such as, for example, glycine. In certain embodiments, the scFv peptide linker connects the N-terminus of the $V_H$ to the C-terminus of the $V_L$. In certain embodiments, the scFv peptide linker can connect the C-terminus of the $V_H$ to the N-terminus of the $V_L$.

In certain embodiments, anti-LGALS3 antibodies or antigen-binding fragments thereof described herein refer to chimeric antigen receptors (CARs). A CAR is an art-recognized term. A CAR can be targeted to a tumor associated antigen (e.g., LGALS3). CARs as provided herein typically are composed of a scFv derived from a LGALS3 Glycosylation Antibody, a transmembrane domain, which in some embodiments is a T cell costimulatory molecule-derived transmembrane domain (for example, a transmembrane domain derived from CD28, CD8, CD38, OX-40, or 4-1BB), and a primary signaling domain, such as the T cell receptor (TCR) zeta (ζ) chain cytoplasmic signaling domain. In some embodiments, the CAR further includes one or more additional regions or domains such as one or more spacer or linker, including an extracellular spacer, such as one derived from an antibody or other cell-surface molecule, such as a spacer containing gone or more of antibody CH2, CH3, and/or hinge regions, or a spacer derived from a CD28 molecule or a CD8 molecule, or other spacer. Also provided herein are cells, such as T cells engineered to express such CARs, such as those recombinantly expressing such a CAR. A CAR-expressing T cell, upon recognition of a LGALS3 expressing tumor, preferably induces T cell activation, proliferation, and/or lysis of a cell of such a tumor.

Anti-LGALS3 antibodies can be of any type (e.g., IgG, IgE, IgM, IgD, IgA or IgY), any class (e.g., IgG1, IgG2, IgG3, IgG4, IgA1 or IgA2), or any subclass (e.g., IgG2a or IgG2b) of immunoglobulin molecule. In certain embodiments, antibodies described herein are IgG antibodies, or a class or subclass thereof. In certain embodiments, antibodies described herein are IgG1 antibodies. In certain embodiments, antibodies described herein are IgG2 antibodies. In certain embodiments, antibodies described herein are IgG2a antibodies. In certain embodiments, antibodies described herein are IgG2b antibodies. In certain embodiments, antibodies described herein are IgG3 antibodies. In certain embodiments, antibodies described herein are IgG4 antibodies. In certain embodiments, antibodies described herein are a mixture of antibody types or a mixture of subclasses. In certain embodiments, antibodies described herein are a mixture of IgG2a and IgG2b antibodies. In a specific embodiment, the antibody is a humanized form of a rodent monoclonal antibody.

Antigen binding fragments of anti-LGALS3 antibodies can be Fab fragments, F(ab')2 fragments, or a portion of anti-LGALS3 antibody which comprises the amino acid residues that confer on the anti-LGALS3 antibody its specificity for the antigen (e.g., the complementarity determining regions (CDR)). The anti-LGALS3 antibody can be derived from any animal species, such as rodents (e.g., mouse, rat or hamster) and humans.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in a mature heavy chain and about the amino-terminal 90 to 100 amino acids in a mature light chain, which differs extensively in sequence among antibodies and is used in the binding and specificity of a particular antibody for its particular antigen. The variability in sequence is concentrated in those regions called complementarity determining regions (CDRs) while the more highly conserved regions in the variable domain are called framework regions (FR). CDRs are flanked by FRs. Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction and specificity of the antibody with antigen. In certain embodiments, the variable region is a rodent (e.g., mouse or rat) variable region. In certain embodiments, the variable region is a human variable region. In certain embodiments, the variable region comprises rodent (e.g., mouse or rat) CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

CDRs are defined in various ways in the art, including the Kabat, Chothia, and IMGT, and Exemplary definitions. The Kabat definition is based on sequence variability (Kabat, Elvin A. et al., Sequences of Proteins of Immunological Interest. Bethesda: National Institutes of Health, 1983). With respect to the Kabat numbering system, (i) the $V_H$ CDR1 is typically present at amino acid positions 31 to 35 of the heavy chain, which can optionally include one or two additional amino acids following amino acid position 35 (referred to in the Kabat numbering scheme as 35 A and 35B); (ii) the $V_H$ CDR2 is typically present at amino acid positions 50 to 65 of the heavy chain; and (iii) the $V_H$ CDR2 is typically present at amino acid positions 95 to 102 of the heavy chain (Kabat, Elvin A. et al., Sequences of Proteins of Immunological Interest. Bethesda: National Institutes of Health, 1983). With respect to the Kabat numbering system, (i) the $V_L$ CDR1 is typically present at amino acid positions 24 to 34 of the light chain; (ii) the $V_L$ CDR2 is typically present at amino acid positions 50 to 56 of the light chain; and (iii) the $V_L$ CDR3 is typically present at amino acid positions 89 to 97 of the light chain (Kabat, Elvin A. et al., Sequences of Proteins of Immunological Interest. Bethesda: National Institutes of Health, 1983). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

The Chothia definition is based on the location of the structural loop regions (Chothia et al. (1987) *J Mol Biol* 196: 901-917; and U.S. Pat. No. 7,709,226). The term "Chothia CDRs," and like terms are recognized in the art and refer to antibody CDR sequences as determined according to the method of Chothia and Lesk (1987) *J. Mol. Biol.* 196:901-917, which will be referred to herein as the "Chothia CDRs" (see also, e.g., U.S. Pat. No. 7,709,226 and Martin, A., "Protein Sequence and Structure Analysis of Antibody Variable Domains," in Antibody Engineering, Kontermann and Dübel, eds., Chapter 31, pp. 422-439, Springer-Verlag, Berlin (2001)). With respect to the Chothia numbering system, using the Kabat numbering system of numbering amino acid residues in the $V_H$ region, (i) the $V_H$ CDR1 is typically present at amino acid positions 26 to 32 of the heavy chain; (ii) the $V_H$ CDR2 is typically present at amino acid positions 53 to 55 of the heavy chain; and (iii) the $V_H$ CDR3 is typically present at amino acid positions 96 to 101 of the heavy chain. In a specific embodiment, with respect to the Chothia numbering system, using the Kabat number-ing system of numbering amino acid residues in the $V_H$ region, (i) the $V_H$ CDR1 is typically present at amino acid positions 26 to 32 or 34 of the heavy chain; (ii) the $V_H$ CDR2 is typically present at amino acid positions 52 to 56 (in one embodiment, CDR2 is at positions 52A-56, wherein 52A follows position 52) of the heavy chain; and (iii) the $V_H$ CDR3 is typically present at amino acid positions 95 to 102 of the heavy chain (in one embodiment, there is no amino acid at positions numbered 96-100). With respect to the Chothia numbering system, using the Kabat numbering system of numbering amino acid residues in the $V_L$ region, (i) the $V_L$ CDR1 is typically present at amino acid positions 26 to 33 of the light chain; (ii) the $V_L$ CDR2 is typically present at amino acid positions 50 to 52 of the light chain; and (iii) the $V_L$ CDR3 is typically present at amino acid positions 91 to 96 of the light chain. In a specific embodi-ment, with respect to the Chothia numbering system, using the Kabat numbering system of numbering amino acid residues in the $V_L$ region, (i) the $V_L$ CDR1 is typically present at amino acid positions 24 to 34 of the light chain; (ii) the $V_L$ CDR2 is typically present at amino acid positions 50 to 56 of the light chain; and (iii) the $V_L$ CDR3 is typically present at amino acid positions 89 to 97 of the light chain (in one embodiment, there is no amino acid at positions num-bered 96-100). These Chothia CDR positions may vary depending on the antibody, and can be determined according to methods known in the art.

The IMGT definition is from the EVIGT ("IMGT®, the international ImMunoGeneTics information System® web-site imgt.org, founder and director: Marie-Paule Lefranc, Montpellier, France; see, e.g., Lefranc, M.-P., 1999, The Immunologist, 7: 132-136 and Lefranc, M.-P. et al., 1999, Nucleic Acids Res., 27:209-212, both of which are incor-porated herein by reference in their entirety). With respect to the IMGT numbering system, (i) the $V_H$ CDR1 is typically present at amino acid positions 25 to 35 of the heavy chain; (ii) the $V_H$ CDR2 is typically present at amino acid positions 51 to 57 of the heavy chain; and (iii) the $V_H$ CDR2 is typically present at amino acid positions 93 to 102 of the heavy chain. With respect to the IMGT numbering system, (i) the $V_L$ CDR1 is typically present at amino acid positions 27 to 32 of the light chain; (ii) the $V_L$ CDR2 is typically present at amino acid positions 50 to 52 of the light chain; and (iii) the $V_L$ CDR3 is typically present at amino acid positions 89 to 97 of the light chain.

Sequences and Structures of LGALS3 Antibodies

In certain embodiments, provided herein is an anti-LGALS3 antibody or antigen-binding fragment thereof which comprises $V_H$ CDRs of any of the anti-LGALS3 antibodies provided herein, e.g., as set forth in Table 6. In certain embodiments, an anti-LGALS3 antibody or antigen-binding fragment thereof provided herein comprises a $V_H$ CDR1 of an anti-LGALS3 antibody as set forth in Table 6. In certain embodiments, an anti-LGALS3 antibody or anti-gen-binding fragment thereof provided herein comprises a $V_H$ CDR2 of an anti-LGALS3 antibody as set forth in Table 6. In certain embodiments, an anti-LGALS3 antibody or antigen-binding fragment thereof provided herein comprises a $V_H$ CDR3 of an anti-LGALS3 antibody as set forth in Table 6. In certain embodiments, an anti-LGALS3 antibody or antigen-binding fragment thereof provided herein com-prises one, two or all three of $V_H$ CDRs of an anti-LGALS3 antibody as set forth in Table 6.

In certain embodiments, provided herein is an anti-LGALS3 antibody or antigen-binding fragment thereof which comprises $V_L$ CDRs of any of the anti-LGALS3 antibodies provided herein, e.g., as set forth in Table 6. In certain embodiments, an anti-LGALS3 antibody or antigen-binding fragment thereof provided herein comprises a $V_L$ CDR1 of an anti-LGALS3 antibody as set forth in Table 6. In certain embodiments, an anti-LGALS3 antibody or anti-gen-binding fragment thereof provided herein comprises a $V_L$ CDR2 of an anti-LGALS3 antibody as set forth in Table 6. In certain embodiments, an anti-LGALS3 antibody or antigen-binding fragment thereof provided herein comprises a $V_L$ CDR3 of an anti-LGALS3 antibody as set forth in Table 6. In certain embodiments, an anti-LGALS3 antibody or antigen-binding fragment thereof provided herein comprises one, two or all three of $V_L$ CDRs of an anti-LGALS3 antibody in Table 6.

In one aspect, the present disclosure provides an antibody or an antigen binding fragment thereof, comprising a heavy chain immunoglobulin variable domain ($V_H$) and a light chain immunoglobulin variable domain ($V_L$), wherein (a) the $V_H$ comprises a $V_H$-CDR1 sequence selected from the group consisting of SEQ ID NOs: 7, 19, 29, 39, and 49, a $V_H$-CDR2 sequence selected from the group consisting of SEQ ID NOs: 8, 20, 30, 40, and 50, and a $V_H$-CDR3 sequence selected from the group consisting of SEQ ID NOs: 9, 21, 31, 41, and 51, and/or (b) the $V_L$ comprises a $V_L$-CDR1 sequence selected from the group consisting of SEQ ID NOs: 2, 14, 24 34, and 44, a $V_L$-CDR2 sequence selected from the group consisting of SEQ ID NOs: 3, 15, 25, 35, and 45, and a $V_L$-CDR3 sequence selected from the group consisting of SEQ ID NOs: 4, 16, 26, 36, and 46.

In one aspect, the present disclosure provides an antibody or an antigen-binding fragment thereof that specifically binds to a Galectin-3 (LGALS3), wherein the antibody or antigen-binding fragment thereof comprises a heavy chain variable region ($V_H$) and a light chain variable region ($V_L$), wherein: (a) the $V_H$ comprises a $V_H$ complementarity determining region (CDR)1 sequence comprising SEQ ID NO: 7, a $V_H$ CDR2 sequence comprising SEQ ID NO: 8, and a $V_H$ CDR3 sequence comprising SEQ ID NO: 9, and/or the $V_L$ comprises a $V_L$ CDR1 sequence comprising SEQ ID NO: 2, a $V_L$ CDR2 sequence comprising SEQ ID NO: 3, and a $V_L$ CDR3 sequence comprising SEQ ID NO: 4; (b) the $V_H$ comprises a $V_H$ complementarity determining region (CDR)1 sequence comprising SEQ ID NO: 19, a $V_H$ CDR2 sequence comprising SEQ ID NO: 20, and a $V_H$ CDR3 sequence comprising SEQ ID NO: 21, and/or the $V_L$ comprises a $V_L$ CDR1 sequence comprising SEQ ID NO: 14, a $V_L$ CDR2 sequence comprising SEQ ID NO: 15, and a $V_L$ CDR3 sequence comprising SEQ ID NO: 16; (c) the $V_H$ comprises a $V_H$ complementarity determining region (CDR)1 sequence comprising SEQ ID NO: 29, a $V_H$ CDR2 sequence comprising SEQ ID NO: 30, and a $V_H$ CDR3 sequence comprising SEQ ID NO: 31, and/or the $V_L$ comprises a $V_L$ CDR1 sequence comprising SEQ ID NO: 24, a $V_L$ CDR2 sequence comprising SEQ ID NO: 25, and a $V_L$ CDR3 sequence comprising SEQ ID NO: 26; (d) the $V_H$ comprises a $V_H$ complementarity determining region (CDR)1 sequence comprising SEQ ID NO: 39, a $V_H$ CDR2 sequence comprising SEQ ID NO: 40, and a $V_H$ CDR3 sequence comprising SEQ ID NO: 41, and/or the $V_L$ comprises a $V_L$ CDR1 sequence comprising SEQ ID NO: 34, a $V_L$ CDR2 sequence comprising SEQ ID NO: 35, and a $V_L$ CDR3 sequence comprising SEQ ID NO: 36; or (e) the $V_H$ comprises a $V_H$ complementarity determining region (CDR)1 sequence comprising SEQ ID NO: 49, a $V_H$ CDR2 sequence comprising SEQ ID NO: 50, and a $V_H$ CDR3 sequence comprising SEQ ID NO: 51, and/or the $V_L$ comprises a $V_L$ CDR1 sequence comprising SEQ ID NO: 44, a $V_L$ CDR2 sequence comprising SEQ ID NO: 45, and a $V_L$ CDR3 sequence comprising SEQ ID NO: 46.

In a particular embodiment, an anti-LGALS3 antibody or antigen-binding fragment thereof described herein comprises a $V_H$ region selected from the group consisting of SEQ ID NO: 6, SEQ ID NO: 18, SEQ ID NO: 28, SEQ ID NO: 38, and SEQ ID NO: 48.

In a particular embodiment, an anti-LGALS3 antibody or antigen-binding fragment thereof described herein comprises a $V_L$ region selected from the group consisting of SEQ ID NO: 1, SEQ ID NO: 13, SEQ ID NO: 23, SEQ ID NO: 33, and SEQ ID NO: 43.

In some embodiments, the $V_H$ comprises an amino acid sequence selected from the group consisting of SEQ ID NO: 6, SEQ ID NO: 18, SEQ ID NO: 28, SEQ ID NO: 38, and SEQ ID NO: 48, and/or the $V_L$ comprises an amino acid sequence selected from the group consisting of SEQ ID NO: 1, SEQ ID NO: 13, SEQ ID NO: 23, SEQ ID NO: 33, and SEQ ID NO: 43. Additionally or alternatively, in some embodiments, wherein the antigen-binding fragment is a Fab, F(ab')$_2$, Fab', Fv or scFv.

Additionally or alternatively, in certain embodiments, the antibody or antigen-binding fragment comprises a $V_H$ amino acid sequence and a $V_L$ amino acid sequence selected from the group consisting of SEQ ID NO: 6 and SEQ ID NO: 1, SEQ ID NO: 18 and SEQ ID NO: 13, SEQ ID NO: 28 and SEQ ID NO: 23, SEQ ID NO: 38 and SEQ ID NO: 33, and SEQ ID NO: 48 and SEQ ID NO: 43, respectively.

In a particular embodiment, an anti-LGALS3 antibody or antigen-binding fragment thereof described herein comprises a $V_H$ region of an anti-LGALS3 antibody as set forth in Table 6. In a particular embodiment, an anti-LGALS3 antibody or antigen-binding fragment thereof described herein comprises a $V_L$ region of an anti-LGALS3 antibody set forth in Table 6.

In certain embodiments, an anti-LGALS3 antibody or antigen binding fragment thereof described herein can be described by its $V_H$ domain alone, or its $V_L$ domain alone, or by its three $V_H$ CDRs alone, or by its three $V_L$ CDRs alone. See, e.g., Rader C et al. (1998) PNAS 95: 8910-8915, which is incorporated herein by reference in its entirety, which describes the humanization of the mouse anti-avP3 antibody by identifying a complementing light chain or heavy chain, respectively, from a human light chain or heavy chain library, resulting in humanized antibody variants having affinities as high or higher than the affinity of the original antibody. See also, Clackson T et al., (1991) Nature 352: 624-628, which is incorporated herein by reference in its entirety, describing methods of producing antibodies that bind a specific antigen by using a specific $V_H$ domain (or $V_L$ domain) and screening a library for the complementary variable domains. See also, Kim and Hong (2007) J Microbiol 45: 572-577, which is incorporated herein by reference in its entirety, describing methods of producing antibodies that bind a specific antigen by using a specific $V_H$ domain and screening a library (e.g., human $V_L$ library) for complementary $V_L$ domains; the selected $V_L$ domains in turn could be used to guide selection of additional complementary (e.g., human) $V_H$ domains.

In certain embodiments, an anti-LGALS3 antibody or antigen binding fragment thereof described herein can be a humanized antibody, for example, a humanized form of a rodent antibody. Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and chain shuffling (U.S. Pat. No. 5,565,332), veneering or resurfacing (European Patent Nos. EP 592,106 and EP 519,596; Padlan (1991) Molecular Immunology 28(4/5):489-498; Studnicka et al. (1994) Protein Engineering 7(6):805-814; and Roguska et al. (1994) PNAS 91:969-973), and techniques disclosed in, e.g., U.S. Pat. Nos. 6,407,213, 5,766,886, WO 9317105, Sandhu (1994) Gene 150(2):409-10, Pedersen et al. (1994)

*J. Mol. Biol.* 235(3):959-73, Couto et al. (1995) *Cancer Res.* 55(8): 1717-22, Roguska et al. (1996) *Protein Eng.* 9(10): 895 904, Baca et al. (1997) *J. Biol. Chem.* 272(16): 10678-84, Couto et al. (1995) *Cancer Res.* 55 (23 Supp):5973s-5977s, Caldas et al. (2000) *Protein Eng.* 13(5):353-Morea et al. (2000) *Methods* 20(3):267-79, and Tan et al. (2002) *J. Immunol.* 169: 1119-See also U.S. Patent Pub. No. US 2005/0042664 A1 (Feb. 24, 2005), each of which is incorporated by reference herein in its entirety.

In certain embodiments, an anti-LGALS3 antibody or antigen binding fragment thereof described herein is a composite human antibody. A composite human antibody can be generated by, e.g., designing variable region sequences from fragments of multiple human antibody variable region sequences in a manner that avoids T cell epitopes, thereby minimizing the immunogenicity of the resulting antibody (see, e.g., Baker et al. (2010) *Self Nonself* 1 (4):314-322; Bryson et al. (2010) *BioDrugs* 24(1): 1-8; and Jones et al. (2009) *Methods Mol Biol.* 525:405-23). Such antibodies can comprise human constant region sequences, e.g., human light chain and/or heavy chain constant regions.

In certain embodiments, an anti-LGALS3 antibody or antigen binding fragment thereof described herein can be a deimmunized antibody. A deimmunized antibody is an antibody in which T-cell epitopes have been removed. Methods for making deimmunized antibodies have been described. See, e.g., Jones et al. Methods Mol Biol. 2009; 525:405-23, xiv, and De Groot et al. (2006) *Cell. Immunol.* 244: 148-153).

In specific embodiments, an anti-LGALS3 antibody or antigen-binding fragment thereof described herein is a humanized immunoglobulin that comprises the 3 $V_H$ CDRs and the 3 $V_L$ CDRs (i.e., $V_H$ CDR1, $V_H$ CDR2, $V_H$ CDR3, $V_L$ CDR1, $V_L$ CDR2, and $V_L$ CDR3) of any of the antibodies disclosed in Table 6, human-derived framework regions, and human derived constant regions. Non-limiting examples of human framework regions are described in the art, e.g., see Kabat et al. (1991) Sequences of Proteins of Immunological Interest Fifth Edition, U.S. Department of Health and Human Services, NIH Publication No. 91-3242). In certain embodiment, an anti-LGALS3 antibody or antigen binding fragment thereof described herein comprises framework regions (e.g., framework regions of the $V_L$ domain and/or $V_H$ domain) that are human framework regions or derived from human framework regions. In certain embodiments, an anti-LGALS3 antibody or antigen binding fragment thereof described herein comprises framework regions (e.g., framework regions of the $V_L$ domain and/or $V_H$ domain) that are primate (e.g., non-human primate) framework regions or derived from primate (e.g., non-human primate) framework regions. For example, CDRs from antigen-specific non-human antibodies, typically of rodent origin (e.g., mouse or rat), are grafted onto homologous human or non-human primate (e.g., Old World apes, e.g., *Pan troglodytes, Pan paniscus* or *Gorilla, Pan troglodytes*, Old World monkeys, e.g., from the genus *Macaca*, or the cynomolgus monkey *Macaca cynomolgus*). Non-human primate framework sequences are described in U.S. Patent Application Publication No. US 2005/0208625.

In a specific embodiment, the position of $V_H$ CDR1, $V_H$ CDR2, and/or $V_H$ CDR3 in the $V_H$ region and/or the position of $V_L$ CDR1, $V_L$ CDR2, and/or $V_L$ CDR3 in the $V_L$ region of an anti-LGALS3 antibody or antigen binding fragment thereof described herein may vary by 1, 2, 3, 4, 5, 6, or more amino acid positions so long as specific binding to LGALS3 or a portion thereof containing the carbohydrate binding domain is maintained (e.g., by at least 50%, at least 60%, at least 70%, at least 80%, at least 90%, at least 95%).

In another embodiment, the length of $V_H$ CDR1, $V_H$ CDR2, and/or $V_H$ CDR3 in the $V_H$ region and/or the length of $V_L$ CDR1, $V_L$ CDR2, and/or $V_L$ CDR3 in the $V_L$ region of an anti-LGALS3 antibody or antigen binding fragment thereof described herein may vary (e.g., be shorter or longer) by 1, 2, 3, 4, 5, 6, or more amino acids, so long as specific binding to LGALS3 or a portion thereof containing the carbohydrate binding domain is maintained (e.g., by at least 50%, at least 60%, at least 70%, at least 80%, at least 90%, at least 95%).

In another embodiment, the amino terminus and/or the carboxy terminus of a $V_H$ CDR1, $V_H$ CDR2, $V_H$ CDR3, $V_L$ CDR1, $V_L$ CDR2, and/or $V_L$ CDR3 described herein can be extended or shortened by 1, 2, 3, 4, 5, 6, or more amino acids compared to one or more of the CDRs described herein so long as specific binding to LGALS3 or a portion thereof containing the carbohydrate binding domain is maintained (e.g., by at least 50%, at least 60%, at least 70%, at least 80%, at least 90%, at least 95%).

Any method known in the art can be used to ascertain whether specific binding to LGALS3 is maintained, e.g., ELISA binding assays, SPR analysis, or FACS analysis.

In specific aspects, provided herein is an anti-LGALS3 antibody or antigen-binding fragment thereof comprising an antibody heavy chain and/or light chain, e.g., a heavy chain alone, a light chain alone, or both a heavy chain and a light chain.

In some embodiments, an anti-LGALS3 antibody or an antigen-binding fragment thereof described herein comprises a heavy chain wherein the amino acid sequence of the variable region of the heavy chain comprises a $V_H$ CDR1, $V_H$ CDR2, and $V_H$ CDR3 of any one of antibodies listed in Table 6, and wherein the constant region of the heavy chain is a human heavy chain constant region. In a particular embodiment, an anti-LGALS3 antibody or an antigen-binding fragment thereof described herein comprises a heavy chain wherein the amino acid sequence of the variable region of the heavy chain comprises a $V_H$ CDR1, $V_H$ CDR2, and $V_H$ CDR3 having the amino acid sequences of SEQ ID NO: 7, SEQ ID NO: 8, and SEQ ID NO: 9, respectively; SEQ ID NO: 19, SEQ ID NO: 20, and SEQ ID NO: 21, respectively; SEQ ID NO: 29, SEQ ID NO: 30, and SEQ ID NO: 31, respectively; SEQ ID NO: 39, SEQ ID NO: 40, and SEQ ID NO: 41, respectively; or SEQ ID NO: 49, SEQ ID NO: 50, and SEQ ID NO: 51, respectively, wherein the constant region of the heavy chain is a human heavy chain constant region.

In a specific embodiment, an anti-LGALS3 antibody or an antigen-binding fragment thereof described herein comprises a heavy chain wherein the amino acid sequence of the variable region of the heavy chain comprises the amino acid sequence of SEQ ID NO: 6, SEQ ID NO: 18, SEQ ID NO: 28, SEQ ID NO: 38, or SEQ ID NO: 48, and wherein the constant region of the heavy chain is a human heavy chain constant region. Non-limiting examples of human constant region sequences have been described in the art, e.g., see Kabat E A et al. (1991) supra.

In some embodiments, the heavy chain of an anti-LGALS3 antibody or an antigen-binding fragment thereof described herein can be an alpha (α), delta (δ), epsilon (ε), gamma (γ) or mu (μ) heavy chain. In another specific embodiment, the heavy chain of an anti-LGALS3 antibody or antigen binding fragment thereof described can comprise a human alpha (α), delta (δ), epsilon (ε), gamma (γ) or mu (μ) heavy chain. In some embodiments, an anti-LGALS3 antibody or an antigen-binding fragment thereof described herein comprises a heavy chain wherein the amino acid sequence of the variable region of the heavy chain comprises a $V_H$ CDR1, $V_H$ CDR2, and $V_H$ CDR3 of any one of antibodies listed in Table 6, and wherein the constant region of the heavy chain is an alpha ($\alpha$), delta ($\delta$), epsilon ($\varepsilon$), gamma ($\gamma$) or mu ($\mu$) heavy chain.

In a particular embodiment, an anti-LGALS3 antibody or an antigen-binding fragment thereof described herein comprises a heavy chain wherein the amino acid sequence of the variable region of the heavy chain comprises a $V_H$ CDR1, $V_H$ CDR2, and $V_H$ CDR3 having the amino acid sequences of SEQ ID NO: 7, SEQ ID NO: 8, and SEQ ID NO: 9, respectively; SEQ ID NO: 19, SEQ ID NO: 20, and SEQ ID NO: 21, respectively; SEQ ID NO: 29, SEQ ID NO: 30, and SEQ ID NO: 31, respectively; SEQ ID NO: 39, SEQ ID NO: 40, and SEQ ID NO: 41, respectively; or SEQ ID NO: 49, SEQ ID NO: 50, and SEQ ID NO: 51, respectively, wherein the constant region of the heavy chain is a human alpha ($\alpha$), delta ($\delta$), epsilon ($\varepsilon$), gamma ($\gamma$) or mu ($\mu$) heavy chain. In a specific embodiment, an anti-LGALS3 antibody or an antigen-binding fragment thereof described herein comprises a heavy chain wherein the amino acid sequence of the variable region of the heavy chain comprises the amino acid sequence of SEQ ID NO: 6, SEQ ID NO: 18, SEQ ID NO: 28, SEQ ID NO: 38, or SEQ ID NO: 48, and wherein the constant region of the heavy chain is a human alpha ($\alpha$), delta ($\delta$), epsilon ($\varepsilon$), gamma ($\gamma$) or mu ($\mu$) heavy chain.

In a particular embodiment, an anti-LGALS3 antibody or an antigen-binding fragment thereof described herein comprises a light chain wherein the amino acid sequence of the variable region of the light chain comprises a $V_L$ CDR1, $V_L$ CDR2, and $V_L$ CDR3 of any one of antibodies listed in Table 6 and wherein the constant region of the light chain is a human light chain constant region. In a particular embodiment, an anti-LGALS3 antibody or an antigen-binding fragment thereof described herein comprises a light chain wherein the amino acid sequence of the variable region of the light chain comprises a $V_L$ CDR1, $V_L$ CDR2, and $V_L$ CDR3 having the amino acid sequences of SEQ ID NO: 2, SEQ ID NO: 3, and SEQ ID NO: 4, respectively; SEQ ID NO: 14, SEQ ID NO: 15, and SEQ ID NO: 16, respectively; SEQ ID NO: 24, SEQ ID NO: 25, and SEQ ID NO: 26, respectively; SEQ ID NO: 34, SEQ ID NO: 35, and SEQ ID NO: 36, respectively; or SEQ ID NO: 44, SEQ ID NO: 45, and SEQ ID NO: 46, respectively, and wherein the constant region of the light chain is a human light chain constant region. In a specific embodiment, an anti-LGALS3 antibody or an antigen-binding fragment thereof described herein comprises a light chain wherein the amino acid sequence of the variable region of the light chain comprises the amino acid sequence of SEQ ID NO: 1, SEQ ID NO: 13, SEQ ID NO: 23, SEQ ID NO: 33, or SEQ ID NO: 43, and wherein the constant region of the light chain is a human light chain constant region.

In some embodiments, the light chain of an anti-LGALS3 antibody or an antigen-binding fragment thereof described herein is a kappa light chain. In another specific embodiment, the light chain of an anti-LGALS3 antibody or an antigen-binding fragment thereof described herein is a lambda light chain. In yet another specific embodiment, the light chain of an anti-LGALS3 antibody or an antigen-binding fragment thereof described herein is a human kappa light chain or a human lambda light chain. In a particular embodiment, an anti-LGALS3 antibody or an antigen-binding fragment thereof described herein comprises a light chain wherein the amino acid sequence of the variable region of the light chain comprises a $V_L$ CDR1, $V_L$ CDR2, and $V_L$ CDR3 of any one of antibodies listed in Table 6 and wherein the constant region of the light chain is a kappa ($\kappa$) or a lambda ($\lambda$) light chain constant region. In a particular embodiment, an anti-LGALS3 antibody or an antigen-binding fragment thereof described herein comprises a light chain wherein the amino acid sequence of the variable region of the light chain comprises a $V_L$ CDR1, $V_L$ CDR2, and $V_L$ CDR3 having the amino acid sequences of SEQ ID NO: 2, SEQ ID NO: 3, and SEQ ID NO: 4, respectively; SEQ ID NO: 14, SEQ ID NO: 15, and SEQ ID NO: 16, respectively; SEQ ID NO: 24, SEQ ID NO: 25, and SEQ ID NO: 26, respectively; SEQ ID NO: 34, SEQ ID NO: 35, and SEQ ID NO: 36, respectively; or SEQ ID NO: 44, SEQ ID NO: 45, and SEQ ID NO: 46, respectively, and wherein the constant region of the light chain is a kappa or lambda light chain constant region. In a specific embodiment, an anti-LGALS3 antibody or an antigen-binding fragment thereof described herein comprises a light chain wherein the amino acid sequence of the variable region of the light chain comprises the amino acid sequence of SEQ ID NO: 1, SEQ ID NO: 13, SEQ ID NO: 23, SEQ ID NO: 33, or SEQ ID NO: 43, and wherein the constant region of the light chain is a kappa or lambda light chain constant region.

In a specific embodiment, an anti-LGALS3 antibody or antigen-binding fragment thereof described herein comprises a heavy chain variable region ($V_H$) and a light chain variable region ($V_L$) as described herein, and wherein the constant regions are of the type found in an IgG, IgE, IgM, IgD, IgA or IgY immunoglobulin molecule, or a human IgG, IgE, IgM, IgD, IgA or IgY immunoglobulin molecule. In another specific embodiment, an anti-LGALS3 antibody or antigen-binding fragment thereof described herein comprises a $V_H$ and a $V_L$ comprising any amino acid sequences described herein, and wherein the constant regions are of the type found in an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. In a particular embodiment, the constant regions are of the type found in a human IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2) of human immunoglobulin molecule.

In certain embodiments, the epitope of an antibody can be determined by, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al. (1994) *Acta Crystallogr D Biol Crystallogr* 50(Pt 4): 339-350; McPherson A (1990) *Eur J Biochem* 189: 1-23; Chayen N E (1997) *Structure* 5: 1269-1274; McPherson A (1976) *J Biol Chem* 251: 6300-6303). Antibody: antigen crystals can be studied using well known X-ray diffraction techniques and can be refined using computer software such as X-PLOR (Yale University, 1992, distributed by Molecular Simulations, Inc.; see e.g., Meth Enzymol (1985) volumes 114 & 115, eds Wyckoff H W et al.; U.S. Patent Application No. 2004/0014194), and BUSTER (Bricogne G (1993) *Acta Crystallogr D Biol Crystallogr* 49(Pt 1): 37-60; Bricogne G (1997) *Meth Enzymol* 276A: 361-423, ed Carter C W; Roversi P et al. (2000) *Acta Crystallogr D Biol Crystallogr* 56(Pt 10): 1316-1323). Mutagenesis mapping studies can be accomplished using any method known to one of skill in the art. See, e.g., Champe M et al. (1995) and Cunningham B C & Wells J A (1989) for a description of mutagenesis techniques, including alanine scanning mutagenesis techniques. In addition, antibodies that recognize and bind to the same or overlapping epitopes can be identified using routine techniques such as an immunoassay, e.g., by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen. Numerous types of competitive binding assays are known, e.g.: solid phase direct or indirect radioimmunoassay (MA), solid phase direct or indirect enzyme immunoassay (EIA), sandwich competition assay (see Stahli C et al. (1983) *Methods Enzymol* 9: 242-253); solid phase direct biotin-avidin EIA (see Kirkland T N et al. (1986) *J Immunol* 137: 3614-9); solid phase direct labeled assay, solid phase direct labeled sandwich assay (see Harlow E & Lane D, (1988) Antibodies: A Laboratory Manual, Cold Spring Harbor Press); solid phase direct label MA using 1-125 label (see Morel G A et al. (1988) *Mol Immunol* 25(1): 7-15); solid phase direct biotin-avidin EIA (Cheung R C et al. (1990) *Virology* 176: 546-52); and direct labeled MA. (Moldenhauer G et al. (1990) *Scand J Immunol* 32: 77-82). Typically, such an assay involves the use of purified antigen bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 55-60%, 60-65%, 65-70%) 70-75%) or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details, see, e.g., Wagener C et al. (1983) *J Immunol* 130: 2308-2315; Wagener C et al. (1984) *J Immunol Methods* 68: 269-274; Kuroki M et al. (1990) *Cancer Res* 50: 4872-4879; Kuroki M et al. (1992) *Immunol Invest* 21: 523-538; Kuroki M et al. (1992) *Hybridoma* 11: 391-407 and Antibodies: A Laboratory Manual, Ed Harlow E & Lane D editors supra, 386-389.

In certain aspects, competition binding assays can be used to determine whether an antibody is competitively blocked, e.g., in a dose dependent manner, by another antibody e.g., an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an anti-LGALS3 antibody or antigen binding fragment thereof described herein.

In another aspect, provided herein are antibodies that do not compete (e.g., in a dose dependent manner) for binding to LGALS3 with an anti-LGALS3 antibody or antigen binding fragment thereof described herein, as determined using assays known to one of skill in the art or described herein (e.g., ELISA). In another aspect, provided herein are antibodies that do not competitively inhibit (e.g., in a dose dependent manner) an anti-LGALS3 antibody or antigen binding fragment thereof described herein from binding to LGALS3, as determined using assays known to one of skill in the art or described herein (e.g., ELISA).

In certain embodiments, provided herein is an antibody that competes with an antibody described herein for binding to the same extent that an anti-LGALS3 antibody or antigen binding fragment thereof described herein self-competes for binding to LGALS3. In certain embodiments, provided herein is a first antibody that competes with an anti-LGALS3 antibody or antigen binding fragment thereof described herein for binding to LGALS3, wherein the competition is exhibited as reduced binding of the first antibody to the epitope by more than 80% (e.g., 85%, 90%, 95%, or 98%, or between 80% to 85%, 80% to 90%, 85% to 90%, or 85% to 95%). In specific aspects, provided herein is an anti-LGALS3 antibody or antigen binding fragment thereof which competes (e.g., in a dose dependent manner) for specific binding to LGALS3, with an anti-LGALS3 antibody or antigen binding fragment thereof comprising a $V_H$ comprising a $V_H$ CDR1, a $V_H$ CDR2, and/or a $V_H$ CDR3 comprising amino acid sequences as described in Table 6 and/or a $V_L$ comprising a $V_L$ CDR1, a $V_L$ CDR2, and/or a $V_L$ CDR3 comprising amino acid sequences as described in Table 6. In specific aspects, provided herein is an anti-LGALS3 antibody or antigen binding fragment thereof which competes (e.g., in a dose dependent manner) for specific binding to LGALS3, with an anti-LGALS3 antibody or antigen binding fragment thereof comprising a $V_H$ domain having an amino acid sequence as described in Table 6, and/or a $V_L$ as described in Table 6.

In specific aspects, provided herein is an anti-LGALS3 antibody or antigen binding fragment thereof which binds to the same or an overlapping epitope of an antibody comprising a $V_H$ comprising a $V_H$ CDR1, a $V_H$ CDR2, and/or a $V_H$ CDR3 comprising amino acid sequences as described in Table 6 and/or a $V_L$ comprising a $V_L$ CDR1, a $V_L$ CDR2, and/or a $V_L$ CDR3 comprising amino acid sequences as described in Table 6. In specific aspects, provided herein is an anti-LGALS3 antibody or antigen binding fragment thereof that binds to the same or an overlapping epitope of an antibody comprising a $V_H$ domain having an amino acid sequence as described in Table 6 and/or a $V_L$ as described in Table 6.

Assays known to one of skill in the art or described herein (e.g., X-ray crystallography, ELISA assays, surface plasmon resonance (SPR) assays) can be used to determine if two antibodies bind to the same epitope. Affinity can be measured and/or expressed in a number of ways known in the art, including, but not limited to, equilibrium dissociation constant ($K_D$), and equilibrium association constant (KA). The $K_D$ can be determined by techniques known to one of ordinary skill in the art, such as biolayer interferometry.

In certain embodiments, the epitope to which the an anti-LGALS3 antibody or antigen binding fragment thereof described herein binds is used as an immunogen to produce antibodies. In some embodiments, comprises all or a portion of the carbohydrate binding domain of LGALS3.

Functional Characteristics of Anti-LGALS3 Antibodies

In certain embodiments, an anti-LGALS3 antibody or an antigen-binding fragment thereof described herein binds to LGALS3 with a $k_d$ of less than or about $0.5 \times 10^{-3}$/s, $1 \times 10^{-3}$/s, $1.5 \times 10^{-3}$/s, $2 \times 10^{-3}$/s, $2.5 \times 10^{-3}$/s, $3 \times 10^{-3}$/s, $4 \times 10^{-3}$/s, $5 \times 10^{-3}$/s, $6 \times 10^{-3}$/s, $7 \times 10^{-3}$/s, $8 \times 10^{-3}$/s, $9 \times 10^{-3}$/s, $1 \times 10^{-4}$/s, $2\times10^{-4}/s$, $3\times10^{-4}/s$, $4\times10^{-4}/s$, $5\times10^{-4}/s$, $6\times10^{-4}/s$, $7\times10^{-4}/s$, or $8\times10^{-4}/s$. In some embodiments, an anti-LGALS3 antibody or an antigen-binding fragment thereof described herein binds to LGALS3 with a kd of about $0.5\times10^{-3}/s$ to $8\times10^{-4}/s$.

In certain embodiments, an anti-LGALS3 antibody or an antigen-binding fragment thereof described herein binds to LGALS3 with a ka of at least or about $2.5\times10^4/s$, $3\times10^4/s$, $3.5\times10^4/s$, $4\times10^4/s$, $4.5\times10^4/s$, $5\times10^4/s$, $5.5\times10^4/s$, $6\times10^4/s$, $6.5\times10^4/s$, $7\times10^4/s$, $7.5\times10^4/s$, $8\times10^4/s$, $9\times10^4/s$, or $9\times10^5/s$. In certain embodiments, an anti-LGALS3 antibody or an antigen-binding fragment thereof described herein binds to LGALS3 with a ka of at least or about $2.5\times10^4/s$ to $9\times10^5/s$.

In certain embodiments, an anti-LGALS3 antibody or an antigen-binding fragment thereof described herein binds to LGALS3 with a $K_D$ of less than or about 1000 nM, 500 nM, 100 nM, 50 nM, 25 nM, 20 nM, 15 nM, 10 nM, 5 nM, 4 nM, 3 nM, 2 nM, 1 nM, 0.5 nM, 0.1 nM, or 0.05 nM. In some embodiments, an anti-LGALS3 antibody or an antigen-binding fragment thereof described herein binds to LGALS3 with a $K_D$ of about 1 nM to about 1000 nM. In some embodiments, an anti-LGALS3 antibody or an antigen-binding fragment thereof described herein binds LGALS3 with a $K_D$ of about 1 nM to about 100 nM. In some embodiments, an anti-LGALS3 antibody or an antigen-binding fragment thereof described herein binds LGALS3 with a $K_D$ of about 5 nM to about 50 nM. In some embodiments, an anti-LGALS3 antibody or an antigen-binding fragment thereof described herein binds LGALS3 with a $K_D$ of about 5 nM to about 20 nM.

In certain embodiments, the anti-LGALS3 antibody or antigen-binding fragment thereof provided herein binds to LGALS3 at least 10, 20, 30, 40, 50, 60, 70, 80, 90, 100, 250, 500, or 1000 fold more than an isotype control antibody binds to LGALS3. An isotype control antibody is an art-recognized term that refers to an antibody that lacks specificity to the target, but match the class and type of the primary antibody (e.g., an anti-LGALS3 antibody or antigen-binding fragment thereof provided herein). Isotype controls are used as negative controls to help differentiate non-specific background signal from specific antibody signal.

In certain embodiments, an anti-LGALS3 antibody or an antigen-binding fragment thereof described herein binds to LGALS3 with a 100-1,000 fold increased affinity over the natural ligand binding.

Assays to determine the anti-LGALS3 antibody- or antigen-binding fragment-mediated inhibition of Gal-3-PE binding to cancer cells are known to a person skilled in the art. For example, OVCAR3 cells can be purchased from ATCC, Manassas, VA. PE labeled Gal-3 (Gal-3-PE) can be purchased from Abcam, Cambridge, MA. Assay for inhibition of Gal-3-PE binding to OVCAR3 cells can be performed as follows: Briefly, cultured SKOV3 cells were trypsinized and washed with culture medium. 500, 1000 or 2000 cells were plated in 24 well plates and grown at 37° C. 5% $CO_2$ humidified incubator. After incubation, the cells were incubated with various concentrations of Gal-3-PE and test antibody. Binding of Gal-3-PE to OVCAR3 cells was detected. A standard curve such as the one in FIG. 3A was used to calculate the extent of inhibition.

In specific embodiments, anti-LGALS3 antibodies or antigen-binding fragments thereof described herein inhibit Gal-3-PE binding to cancer cells by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, as compared to mock treated mice. In specific embodiments, anti-LGALS3 antibodies or antigen-binding fragments thereof described herein inhibit Gal-3-PE binding to cancer cells by at least about 25% or 35%), optionally to about 75%, as assessed by methods described herein or known to one of skill in the art, as compared to mock-treated mice. In specific embodiments, anti-LGALS3 antibodies or antigen-binding fragments thereof described herein inhibit Gal-3-PE binding to cancer cells by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, as compared to mock-treated cancer cells. Mock-treated cancer cells can, for example, be treated with phosphate buffered saline or a control (e.g., anti-IgG antibody).

Antibody Conjugates

In some embodiments, an anti-LGALS3 antibody or antigen-binding fragment thereof provided herein is conjugated to another molecule, such as an organic moiety, a detectable label, and/or an isotope.

In certain embodiments, provided herein are anti-LGALS3 antibodies or antigen-binding fragment thereof conjugates, wherein said anti-LGALS3 antibody or antigen-binding fragment thereof is conjugated to one or more agents, e.g., an imaging agent or a cytotoxic agent. Also provided herein are bispecific antibody conjugates, wherein said bispecific antibody is conjugated to one or more agent, e.g., an imaging agent or a cytotoxic agent. Also provided herein are antibody heavy chain conjugates, wherein said antibody heavy chain is conjugated to one or more agent, e.g., an imaging agent or a cytotoxic agent. Also provided herein are antibody light chain conjugates, wherein said antibody light chain is conjugated to one or more agent, e.g., an imaging agent or a cytotoxic agent. Also provided herein are fusion protein conjugates, wherein said fusion protein is conjugated to an agent, e.g., an imaging agent or a cytotoxic agent. In certain embodiments, the agent is conjugated covalently or non-covalently. In certain embodiments, the imaging agent is a detectable label, such as, a chromogenic, enzymatic, radioisotopic, isotopic, fluorescent, toxic, chemiluminescent, nuclear magnetic resonance contrast agent or other label.

Non-limiting examples of suitable chromogenic labels include diaminobenzidine and 4-hydroxyazo-benzene-2-carboxylic acid.

Non-limiting examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Non-limiting examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{223}$Ra, $^{224}$Ra, $^{89}$Zr, $^{177}$Lu, and $^{109}$Pd. In certain embodiments, $^{111}$In is used for in vivo imaging as it avoids the problem of dehalogenation of $^{125}$I or $^{131}$I-labeled anti-LGALS3 antibodies or antigen-binding fragments thereof in the liver. In addition, 111 In has a more favorable gamma emission energy for imaging (Perkins et al. (1985) *Eur. J Nucl. Med.* 70:296-301; Carasquillo et ah, (1987) *J. Nucl. Med.* 25:281-287). For example, 111 In coupled to monoclonal antibodies with 1-(P-isothiocyanatobenzyl)-DPTA has shown little uptake in non-tumorous tissues, particularly the liver, and therefore enhances specificity of tumor localization (Esteban et al., (1987) *J. Nucl. Med.* 28:861-870).

Non-limiting examples of suitable non-radioactive isotopic labels include $^{157}$Gd, $^{55}$Mn, $^{162}$Dy, $^{52}$Tr, and $^{56}$Fe.

Non-limiting examples of suitable fluorescent labels include a $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label.

Non-limiting examples of chemiluminescent labels include a luminol label, an isoluminol label, an aromatic acridinium ester label, an imidazole label, an acridinium salt label, an oxalate ester label, a luciferin label, a luciferase label, and an aequorin label.

Non-limiting examples of nuclear magnetic resonance contrasting agents include heavy metal nuclei such as Gd, Mn, and iron.

Techniques known to one of ordinary skill in the art for conjugating the above-described labels to said anti-LGALS3 antibodies or antigen-binding fragments thereof, bispecific antibodies, antibody heavy chains, antibody light chains, and fusion proteins are described in, for example, Kennedy et al. (1976) *Clin. Chm. Acta* 70: 1-31, and Schurs et al. (1977) *Clin. Chm. Acta* 81: 1-40. Coupling techniques mentioned in the latter are the glutaraldehyde method, the periodate method, the dimaleimide method, the m-maleimidobenzyl-N-hydroxy-succinimide ester method, all of which methods are incorporated by reference herein.

Non-limiting examples of cytotoxic agents include a cytostatic or cytocidal agent, a radioactive metal ion, e.g., alpha-emitters, and toxins, e.g., *pseudomonas* exotoxin, abrin, cholera toxin, ricin A, and diphtheria toxin.

In certain embodiments, the agent is a diagnostic agent. A diagnostic agent is an agent useful in diagnosing or detecting a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MM). U.S. Pat. No. 6,331,175 describes MM technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an anti-LGALS3 antibody or antigen-binding fragment thereof with radioactive metals or paramagnetic ions, it can be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, for example, ethylenediaminetetraacetic acid (EDTA), diethylenetriaminepentaacetic acid (DTP A), porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr.

25, 1989, the disclosure of which is incorporated herein in its entirety by reference. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with an anti-LGALS3 antibody or antigen-binding fragment thereof provided herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as 223Ra for RAIT are encompassed herein.

In certain embodiments, the agent is an organic agent. Such organic agents can produce a conjugate with improved pharmacokinetic properties (e.g., increased in vivo serum half-life). The organic moiety can be a hydrophilic polymeric group, fatty acid group, or fatty acid ester group. As used herein, the term "fatty acid" encompasses monocarboxylic acids and di-carboxylic acids. As used herein, a "hydrophilic polymeric group" refers to an organic polymer that is more soluble in water than in octane, e.g., polylysine. Hydrophilic polymers suitable for modifying an anti-LGALS3 antibody or antigen-binding fragment thereof provided herein can be linear or branched and include, for example, polyalkane glycols (e.g., polyethylene glycol, (PEG), monomethoxy-polyethylene glycol, and polypropylene glycol), carbohydrates (e.g., dextran, cellulose, oligosaccharides, and polysaccharides), polymers of hydrophilic amino acids (e.g., polylysine, polyarginine, and polyaspartate), polyalkane oxides (e.g., polyethylene oxide and polypropylene oxide) and polyvinyl pyrolidone. In certain embodiments, the hydrophilic polymer that modifies an anti-LGALS3 antibody or antigen-binding fragment thereof, a bispecific antibody, an antibody heavy chain, an antibody light chain, or a fusion protein provided herein has a molecular weight of about 800 to about 150,000 Daltons as a separate molecular entity. For example, PEG$_{5000}$ and PEG$_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying an anti-LGALS3 antibody or antigen-binding fragment thereof, a bispecific antibody, an antibody heavy chain, an antibody light chain, or a fusion protein provided herein can be saturated or can contain one or more units of unsaturation. Fatty acids that are suitable for modifying an anti-LGALS3 antibody or antigen-binding fragment thereof, a bispecific antibody, an antibody heavy chain, an antibody light chain, or a fusion protein provided herein include, for example, n-dodecanoate, n-tetradecanoate, n-octadecanoate, n-eicosanoate, n-docosanoate, n-triacontanoate, n-tetracontanoate, cis-delta-9-octadecanoate, all cis-delta-5, 8, 11, 14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The conjugates provided herein can be prepared using suitable methods, such as by reaction with one or more modifying agents. As used herein, an "activating group" is a chemical moiety or functional group that can, under appropriate conditions, react with a second chemical group thereby forming a covalent bond between the modifying agent and the second chemical group. For example, amine-reactive activating groups include electrophilic groups such as, for example, tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see, for example, Hernanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group, wherein one or more carbon atoms can be replaced by a heteroatom such as oxygen, nitrogen or sulfur. Suitable linker moieties include, for example, tetraethylene glycol, $(CH_2)_3$, and NH. Modifying agents that comprise a linker moiety can be produced, for example, by reacting a mono-Boc-alkyldiamine (e.g., mono-Boc-ethylenediamine or mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

A "modifying agent" can refer to a suitable organic group (e.g., hydrophilic polymer, a fatty acid, and a fatty acid ester) that comprises an activating group. For example, the organic moieties can be bonded to the anti-LGALS3 antibody or antigen-binding fragment thereof in a non-site specific manner by employing an amine-reactive modifying agent, for example, an N-hydroxysuccinimide ester of PEG. A modified the anti-LGALS3 antibody or antigen-binding fragment thereof can also be prepared by reducing disulfide bonds (e.g., intra-chain disulfide bonds) of the anti-LGALS3 antibody or antigen-binding fragment thereof, bispecific antibody, antibody heavy chain, antibody light chain, or fusion protein. The reduced anti-LGALS3 antibody or antigen-binding fragment thereof, bispecific antibody, antibody heavy chain, antibody light chain, or fusion protein can then be reacted with a thiol-reactive modifying agent to produce the conjugates provided herein. Conjugates comprising an organic moiety that is bonded to specific sites of an anti-LGALS3 antibody or antigen-binding fragment thereof provided herein can be prepared using suitable methods, such as reverse proteolysis (Fisch et al. (1992) *Bioconjugate Chem.,* 3: 147-153; Werlen et al. (1994) *Bioconjugate Chem.,* 5:41 1-417; Kumaran et al. (1997) *Protein Sci.* 6(10):2233-2241; Itoh et al. (1996) *Bioorg. Chem.,* 24(1): 59-68; Capellas et al. (1997) *Biotechnol. Bioeng.* 56(4):456-463), and the methods described in Hermanson, G. T., Bioconjugate Techniques, Academic Press: San Diego, Calif. (1996).

Antibody Production

Producing and Screening Antibodies

In another aspect, provided herein are methods of producing anti-LGALS3 antibodies or antigen-binding fragments. The antibodies or antigen-binding fragments thereof described herein can be produced by any method known in the art for the synthesis of antibodies, e.g., by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, e.g., in the references cited herein and are fully explained in the literature. See, e.g., Maniatis T et al. (1982) Molecular Cloning: A Laboratory Manual, Cold Spring Harbor Laboratory Press; Sambrook J et al. (1989), Molecular Cloning: A Laboratory Manual, Second Edition, Cold Spring Harbor Laboratory Press; Sambrook J et al. (2001) Molecular Cloning: A Laboratory Manual, Cold Spring Harbor Laboratory Press, Cold Spring Harbor, NY; Ausubel F M et al. Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al. (eds.) (1999) Genome Analysis: A Laboratory Manual, Cold Spring Harbor Laboratory Press.

In a specific embodiment, an anti-LGALS3 antibody or antigen binding fragment thereof described herein is an antibody (e.g., recombinant antibody) prepared, expressed, created or isolated by any means that involves creation, e.g., via synthesis, genetic engineering of DNA sequences. In certain embodiments, such antibody comprises sequences that are encoded by DNA sequences that do not naturally exist within the antibody germline repertoire of an animal or mammal (e.g., human) in vivo. In a specific embodiment, an anti-LGALS3 antibody or antigen binding fragment thereof described herein is made by a method comprising using the carbohydrate binding domain of LGALS3 or a portion thereof. See, e.g., Examples 1-2 for a detailed description of an exemplary method for how to produce antibodies described herein.

In a certain aspect, an anti-LGALS3 antibody provided herein is generated using an immunogenic peptide comprising (SEQ ID NO: 53)
ADNFSLHDALSGSGNPNPQGWPGAWGNQPAGAGGYPGASYPGAYPGQAPP

GAYPGQAPPGAYPGAPGAYPGAPAPGVYPGPPSGPGAYPSSGQPSATGAY

PATGPYGAPAGPLIVPYNLPLPGGVVPRMLITILGTVKPNANRIALDFQR

GNDVAFHFNPRFNENNRRVIVCNTKLDNNWGREERQSVFPFESGKPFKIQ

VLVEPDHFKVAVNDAHLLQYNHRVKKLNEISKLGISGDIDLTSASYTMI.

In a certain aspect, an anti-LGALS3 antibody provided herein is generated using an immunogenic peptide comprising a Fc-fusion protein comprising amino acids 117-224 of LGALS3 linked to the Fc region (CH2 and CH3 domains)

of the human IgG1 heavy chain and the hinge region. Amino acids 117-224 of LGALS3 is represented by the following amino acid sequence:

```
                                          (SEQ ID NO: 54)
PYNLPLPGGVVPRMLITILGTVKPNANRIALDFQRGNDVAFHFNPRFNEN

NRRVIVCNTKLDNNWGREERQSVFPFESGKPFKIQVLVEPDHFKVAVNDA

HLLQYNHRVKKLNEISKLGISGDIDLTS.
```

In some embodiment amino acids 117-224 of LGALS3 can be encoded by the following exemplary nucleotide sequence:

```
                                          (SEQ ID NO: 55)
CCTTATAACCTGCCTTTGCCTGGGGGAGTGGTGCCTCGCATGCTGATAAC

AATTCTGGGCACGGTGAAGCCCAATGCAAACAGAATTGCTTTAGATTTCC

AAAGAGGGAATGATGTTGCCTTCCACTTTAACCCACGCTTCAATGAGAAC

AACAGGAGAGTCATTGTTTGCAATACAAAGCTGGATAATAACTGGGGAAG

GGAAGAAAGACAGTCGGTTTTCCCATTTGAAAGTGGGAAACCATTCAAAA

TACAAGTACTGGTTGAACCTGACCACTTCAAGGTTGCAGTGAATGATGCT

CACTTGTTGCAGTACAATCATCGGGTTAAAAAACTCAATGAAATCAGCAA

ACTGGGAATTTCTGGTGACATAGACCTCACCAGT.
```

In certain embodiments, the immunogenic peptide is conjugated to an immunogenic carrier protein. In most cases, small antigens (e.g., short peptides or small haptens) are not sufficiently complex to elicit the production of antibodies. The immunogenic carrier proteins, because of their large size and complex structure, may confer immunogenicity to conjugated small antigens, resulting in antibodies being produced against epitopes on the small antigens and the immunogenic carrier proteins. Therefore, small antigens are always chemically conjugated with immunogenic carrier proteins to intensify the immune response for successful production of antibodies. Commonly used immunogenic carrier proteins include, but are not limited to, keyhole limpet hemocyanin (KLH), *Concholepas concholepas* hemocyanin (CCH), bovine serum albumin (BSA), and ovalbumin (OVA). In a specific embodiment, the immunogenic peptide is conjugated to KLH. KLH is a copper-containing polypeptide that belongs to a group of non-heme proteins called hemocyanins, which are found in arthropods and mollusks. KLH is isolated from keyhole limpets (*Megathura crenulata*). Because of its evolutionary distance from mammals, high molecular weight, complex structure, and a large surface containing several hundred lysine groups that provide primary amines as targets for conjugation, KLH is an extremely immunogenic and effective carrier protein in mammals.

In certain embodiments, the immunogenic peptide is 10 to 60 amino acid residues in length. In some embodiments, the immunogenic peptide is 10 to 30 amino acid residues in length. In some embodiments, the immunogenic peptide is 15 to 25 amino acid residues in length. In some embodiments, the immunogenic peptide is 15 to 20 amino acid residues in length. In specific embodiments, the immunogenic peptide is 15 to 18 amino acid residues in length.

In certain embodiments, the immunogenic peptide comprises an at least 10 amino acid portion of the LGALS3 CBD domain. In certain embodiments, the immunogenic peptide comprises an at least 10 amino acid portion of the amino acid sequence of SEQ ID NO: 53. In certain other embodiments, the immunogenic peptide comprises an at least 15, 20, 25, or 30 amino acid portion of the amino acid sequence of SEQ ID NO: 53. In specific embodiments, the immunogenic peptide consists of 15 to 30 consecutive amino acid residues of SEQ ID NO: 53.

In another aspect, provided herein is a method of generating an antibody or an antigen-binding fragment thereof that specifically binds to a LGALS3, comprising immunizing a subject with an immunogenic peptide as described above. The subject immunized in accordance with the methods described herein can be, but is not limited to, a goat, a sheep, a donkey, a chicken, a guinea pig, a rat, a rabbit, or a mouse. In some embodiments, the subject immunized in accordance with the methods described herein is a rat, a rabbit, or a mouse. In some embodiments, the subject immunized in accordance with the methods described herein is an AlivaMab® Mouse platform (Ablexis). In a specific embodiment, the subject immunized in accordance with the methods described herein is a mouse. In some embodiments, the subject immunized in accordance with the methods described herein is a transgenic mouse that expresses chimeric forms of various immunoglobulin chains. In some embodiments, the transgenic mouse expresses human variable region linked to a mouse constant region. (See e.g. U.S. Pat. Nos. 8,502,018, 9,580,491, US Patent Publication Nos. 20170218090, 20160222093, and 20130167256, each of which is incorporated by reference in its entirety; see also AlivaMab® Mouse platform (Ablexis)).

Immunization of the subject can be performed by any method known in the art, for example, by administering the immunogenic peptide and an adjuvant to the subject.

In another aspect, also provided herein is a method of preparing an immunogenic peptide described herein. In certain embodiments, the method of preparing the immunogenic peptide comprises synthesizing the peptide moiety. The peptide moiety of the immunogenic peptide can be synthesized by any method known in the art, for example, by Fmoc solid-phase peptide synthesis.

Methods to produce anti-LGALS3 antibodies or antigen-binding fragments thereof described herein are known to one of ordinary skill in the art, for example, by chemical synthesis, by purification from biological sources, or by recombinant expression techniques, including, for example, from mammalian cell or transgenic preparations. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, for example, Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, NY; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press.

A variety of methods exist in the art for the production of anti-LGALS3 antibodies or antigen-binding fragments thereof described herein. For example, the anti-LGALS3 antibody or antigen-binding fragment thereof can be made by recombinant DNA methods, such as those described in U.S. Pat. No. 4,816,567. The one or more DNAs encoding an anti-LGALS3 antibody or antigen-binding fragment thereof provided herein can be readily isolated and sequenced using conventional procedures (e.g., by using oligonucleotide probes that are capable of binding specifically to genes encoding the heavy and light chains of murine antibodies, or such chains from human, humanized, or other sources). Once isolated, the DNA can be placed into expression vectors, which are then transformed into host cells such as NSO cells, Simian COS cells, Chinese hamster ovary (CHO) cells, yeast cells, algae cells, eggs, or myeloma cells that do not otherwise produce immunoglobulin protein, to obtain the synthesis of the anti-LGALS3 antibody or antigen-binding fragment thereof in the recombinant host cells. The DNA also can be modified, for example, by substituting the coding sequence for human heavy and light chain constant domains of a desired species in place of the homologous human sequences (U.S. Pat. No. 4,816,567; Morrison et al. supra) or by covalently joining to the immunoglobulin coding sequence all or part of the coding sequence for a non-immunoglobulin polypeptide. Such a non-immunoglobulin polypeptide can be substituted for the constant domains of an anti-LGALS3 antibody or antigen-binding fragment thereof provided herein. In certain embodiments, the DNA encoding anti-LGALS3 antibodies or antigen-binding fragments thereof provided herein can also be prepared using at least one anti-LGALS3 antibody- or antigen-binding fragment thereof-encoding polynucleotide to provide transgenic animals or mammals, such as goats, cows, horses, sheep, and the like, that produce such antibodies in their milk. Such animals can be provided using known methods. See, for example, but not limited to, U.S. Pat. Nos. 5,827,690; 5,849,992; 4,873,316; 5,849,992; 5,994,616, 5,565,362; 5,304,489, and the like, each of which is entirely incorporated herein by reference.

In certain embodiments, anti-LGALS3 antibodies or antigen-binding fragments thereof provided herein can additionally be prepared using at least one anti-LGALS3 antibody- or antigen-binding fragment thereof-encoding polynucleotide provided herein to provide transgenic plants and cultured plant cells (for example, but not limited to tobacco and maize) that produce such antibodies, specified portions or variants in the plant parts or in cells cultured there from. As a non-limiting example, transgenic tobacco leaves expressing recombinant proteins have been successfully used to provide large amounts of recombinant proteins, for example, using an inducible promoter. See, for example, Cramer et al. (1999) *Curr. Top. Microbol. Immunol.* 240: 95-118 (1999) and references cited therein. Also, transgenic maize has been used to express mammalian proteins at commercial production levels, with biological activities equivalent to those produced in other recombinant systems or purified from natural sources. See, for example, Hood et al. (1999) *Adv. Exp. Med. Biol.* 464: 127-147 and references cited therein. Antibodies have also been produced in large amounts from transgenic plant seeds including antibody fragments, such as scFvs, including tobacco seeds and potato tubers. See, for example, Conrad et al. (1998) *Plant Mol. Biol.* 38: 101-109 and references cited therein. Thus, anti-LGALS3 antibodies or antigen-binding fragments thereof can also be produced using transgenic plants, according to known methods. See also, for example, Fischer et al.

(1999) *Biotechnol. Appl. Biochem.* 30:99-108, Ma et al. (1995) *Trends Biotechnol.* 13:522-7; Ma et al, (1995) *Plant Physiol.* 109:341-6; Whitelam et al. (1994) *Biochem Soc. Trans.* 22:940-944; and references cited therein. Each of the above references is entirely incorporated herein by reference.

In certain embodiments, anti-LGALS3 antibodies or antigen-binding fragments thereof provided herein can be prepared using at least one anti-LGALS3 antibody- or antigen-binding fragment thereof-encoding polynucleotide provided herein to provide bacteria that produce such anti-LGALS3 antibodies or antigen-binding fragments. As a non-limiting example, *E. coli* expressing recombinant proteins has been successfully used to provide large amounts of recombinant proteins. See, for example, Verma et al. (1998) 216(1-2): 165-181 and references cited therein.

Methods for making multispecific (e.g., bispecific antibodies) have been described, see, e.g., U.S. Pat. Nos. 7,951, 917; 7, 183,076; 8,227,577; 5,837,242; 5,989,830; 5,869, 620; 6,132,992 and 8,586,713.

In certain embodiments, anti-LGALS3 antibodies or antigen-binding fragments thereof provided herein are utilized in the generation of bispecific antibodies. Bispecific antibodies can be made by fusing two hybridomas to create hybrid immunoglobulin molecules with two binding sites. Bispecific antibodies not only handcuff tumors to T-cells; they cross-link CD3 on T-cells and initiate the activation cascade. This way, T cell receptor-based cytotoxicity is redirected to desired tumor targets bypassing MHC restrictions. Arming of polyclonally activated T cells (ATC) with an anti-CD3-anti-LGALS3 bispecific binding molecule combines the targeting specificity of the anti-LGALS3 antibody with the non-MHC-restricted perforin/granzyme mediated cytotoxicity of T cells. Bispecific binding molecules BsAb or BiTE can arm ex vivo expanded activated T cells before infusion into a patient. This strategy converts every ATC into a specific CTL (Thakur and Lum (2010) *Curr Opin Mol Ther* 12, 340-349; Grabert et al. (2006) *Clin Cancer Res* 12, 569-576).

Bispecific binding molecules can be comprised of an anti-LGALS3 antibody, wherein the anti-LGALS3 antibody is an immunoglobulin, wherein each light chain of the immunoglobulin is a fusion protein, wherein the fusion protein is the immunoglobulin light chain linked via a peptide linker to a scFv targeting CD3. A N297A mutation in the CH2 domain results in a glycosylation leading to no FcR or Clq binding.

An anti-LGALS3 antibody or antigen-binding fragment thereof provided herein can be utilized to generate a CAR. CARs are most commonly composed of a single chain variable fragment length antibody (scFv), such as one derived from a monoclonal antibody targeting a given tumor associated antigen and/or variant thereof, a transmembrane domain (for example, a transmembrane domain derived from a T Cell surface molecule such as a costimulatory molecule such as CD8, CD28, OX-40, and 4-1BB), a signaling portion of a TCR complex, such as an intracellular domain and/or additional portion(s) of a TCR zeta (0 chain, such as a cytoplasmic signaling domain thereof.

In a specific embodiment, the heavy and light chain variable regions of a monoclonal anti-LGALS3 antibody described herein are isolated from a hybridoma cell line which generates a monoclonal anti-LGALS3 antibody. For example, RNA is extracted from the hybridoma cell line and cDNA is generated from the RNA by reverse transcription PCR. The $V_H$ and $V_L$ chain variable regions are cloned by standard PCR utilizing primers specific for such variable regions. The resulting $V_H$ and $V_L$ fragments are subcloned into a shuttle vector, such as, for example TopoTA PCR 2.1 cloning vector (Invitrogen), and sequenced. The $V_H$ and $V_L$ fragments are subsequently ligated to a (Gly4Ser)3 spacer domain (SEQ ID NO: 56), generating an anti-LGALS3 antibody scFv and fused to the human CD8 leader peptide (CD8L) (CD8L-anti-LGALS3 antibody scFv) by overlapping PCR (see, e.g., Maher et al. (2002) Nat Biotechnol 20(1):70-5 and Gong et al. (1999) Neoplasia 1(2): 123-7). The coding region of the CD8L-anti-LGALS3 antibody scFv is fused to the human CD8 hinge and transmembrane domains, or alternatively to the CD28 transmembrane and cytoplasmic signaling domains, fused to the T cell receptor 0)3-ζ signaling domain (see, e.g., Maher et al. (2002) Nat Biotechnol 20(1):70-5; Brentjens et al. (2003) Nat Med 9(3):279-86; and Brentjens et al. (2007) Clin Cancer Res 13(18 Pt1):5426-35).

Also provided herein is a T cell expressing a CAR described herein. Methods for the generation of a T cell expressing a CAR are known in the art. For example, a CAR construct can be sub-cloned into a modified MMLV retroviral vector SFG (see, e.g., Riviere et al. (1995) Proc Natl Acad Sci USA 92(15):6733-7) or other suitable retroviral vectors. In some embodiments, the retroviral vector is a lentiviral vector, for example, an HIV-based vector. VSV-G pseudotyped retroviral supernatants derived from transduced gpg29 fibroblasts can be used to construct stable PG13 gibbon ape leukemia virus (GaLV) envelope-pseudotyped retroviral producing cell lines (see, e.g., Gong et al. (1999) Neoplasia 1(2): 123-7). Isolated healthy donor peripheral blood mononuclear cells (PBMCs) can be activated with phytohemagglutinin (PHA) at 2 µg/ml (Sigma, St. Louis, MO) and retrovirally transduced on retronectin coated non-tissue culture plates (Quintas-Cardama A, et al. (2007) Hum Gene Ther 18(12): 1253-60) to generate the T cell recombinantly expressing the CAR. Gene transfer of the CAR into the T cell can be assessed by FACS.

Single domain antibodies, e.g., antibodies lacking the light chains, can be produced by methods well known in the art. See, e.g., Riechmann and Muyldermans (1999) J Immunol 231: 25-38; Nuttall S D et al. (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301, each of which are incorporated by reference in their entirety.

In particular embodiments, an anti-LGALS3 antibody or antigen binding fragment thereof described herein, which binds to the same or an overlapping epitope as an anti-LGALS3 antibody described herein, is a human anti-LGALS3 antibody or antigen-binding fragment thereof. In particular embodiments, an anti-LGALS3 antibody or antigen binding fragment thereof described herein, which competitively blocks (e.g., in a dose-dependent manner) any one of the antibodies described herein, from binding to LGALS3, is a human anti-LGALS3 antibody or antigen-binding fragment thereof.

Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg and Huszar (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies which specifically bind to LGALS3 can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen. Such methods are known and are described in the art, see, e.g., Shinmoto H et al. (2004) Cytotechnology 46: 19-23; Naganawa Y et al. (2005) Human Antibodies 14: 27-31.

Exemplary methods of producing antibodies or antigen-binding fragments thereof that specifically bind to LGALS3 and methods of screening and selecting antibodies or antigen-binding fragments thereof that specifically bind to LGALS3 are described in Example 2. In exemplary embodiments, the monoclonal antibodies secreted by the hybridomas are screened for binding to the LGALS3 carbohydrate binding domain peptide (CBD), full-length LSGAL3 protein. In some embodiments, the LGALS3 N-terminus, which contains the polymerization domain, is employed as a control. In some embodiments, the monoclonal antibodies are further screened against human Gal3 (or other members of the galectin family, such as, for example, LGAL1, LGAL7, LGAL8, and LGAL9. In some embodiments, the monoclonal antibodies are further screened by using a functional assay for inhibition of binding of human Gal-3 to suitable cancer cells.

Once an anti-LGALS3 antibody or an antigen-binding fragment thereof described herein has been produced, it can be purified by any method known in the art for purification of an immunoglobulin molecule, e.g., by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an anti-LGALS3 antibody or an antigen-binding fragment thereof described herein is isolated or purified. Generally, an isolated antibody is one that is substantially free of other antibodies with different antigenic specificities than the isolated antibody. For example, in a particular embodiment, a preparation of an anti-LGALS3 antibody or antigen binding fragment thereof described herein is substantially free of cellular material and/or chemical precursors. The language "substantially free of cellular material" includes preparations of an anti-LGALS3 antibody or antigen binding fragment thereof in which the antibody is separated from cellular components of the cells from which it is isolated or recombinantly produced. Thus, an anti-LGALS3 antibody or antigen binding fragment thereof that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an anti-LGALS3 antibody or antigen binding fragment thereof, e.g., different post-translational modified forms of an anti-LGALS3 antibody or antigen binding fragment thereof or other different versions of an anti-LGALS3 antibody or antigen binding fragment thereof (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Polynucleotides

In certain embodiments, provided herein are polynucleotides comprising a nucleotide sequence encoding an anti-LGALS3 antibody or antigen-binding fragment thereof. Also provided herein are vectors comprising such polynucleotides. Also provided herein are polynucleotides encoding antigens of the anti-LGALS3 antibody or antigen-binding fragment thereof described herein. Also provided herein are polynucleotides that hybridize under stringent or lower stringency hybridization conditions to polynucleotides that encode an anti-LGALS3 antibody or antigen-binding fragment thereof described herein.

The language "purified" includes preparations of polynucleotide or nucleic acid molecule having less than about 15%, 10%, 5%, 2%, 1%, 0.5%, or 0.1% (in particular less than about 10%)) of other material, e.g., cellular material, culture medium, other nucleic acid molecules, chemical precursors and/or other chemicals. In a specific embodiment, a nucleic acid molecule(s) encoding an anti-LGALS3 antibody or antigen-binding fragment thereof described herein is isolated or purified.

Nucleic acid molecules provided herein can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

In certain embodiments, provided herein is a polynucleotide comprising nucleotide sequences encoding anti-LGALS3 antibody or antigen-binding fragment thereof described herein. In particular aspects, also provided herein are polynucleotides comprising nucleotide sequences encoding anti-LGALS3 antibodies or antigen-binding fragments thereof, which specifically bind to LGALS3, and comprise an amino acid sequence as described herein, as well as antibodies which compete with such anti-LGALS3 antibody or antigen-binding fragment thereof for binding to LGALS3, or which binds to the same epitope as that of such antibodies.

The polynucleotides provided herein can be obtained by any method known in the art. For example, if the nucleotide sequence encoding an anti-LGALS3 antibody or antigen-binding fragment thereof described herein is known, a polynucleotide encoding the anti-LGALS3 antibody or antigen-binding fragment thereof can be can be assembled from chemically synthesized oligonucleotides (e.g., as described in Kutmeier et al. (1994) *BioTechniques* 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-LGALS3 antibody or antigen-binding fragment thereof can be generated from nucleic acid from a suitable source. If a clone containing a nucleic acid encoding a particular anti-LGALS3 antibody or antigen-binding fragment thereof is not available, but the sequence of the anti-LGALS3 antibody or antigen-binding fragment thereof is known, a nucleic acid encoding the anti-LGALS3 antibody or antigen-binding fragment thereof can be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an anti-LGALS3 antibody or antigen binding fragment thereof provided herein) by PCR amplification using synthetic primers that hybridize to the 3' and 5' ends of the sequence or by cloning using an oligonucleotide probe specific for the particular gene sequence to identify, for example, a cDNA clone from a cDNA library that encodes the antibody. Amplified nucleic acids generated by PCR may then be cloned into replicable cloning vectors using any method well known in the art. In such embodiments, a polynucleotide encoding such an anti-LGALS3 antibody or antigen-binding fragment thereof can be manipulated using methods well known in the art for the manipulation of nucleotide sequences, e.g., recombinant DNA techniques, site directed mutagenesis, PCR, etc. (see, for example, the techniques described in Sambrook et al. (19900 Molecular Cloning, A Laboratory Manual, 2d Ed., Cold Spring Harbor Laboratory, Cold Spring Harbor, N.Y. and Ausubel et al., eds. (1998) Current Protocols in Molecular Biology, John Wiley & Sons, N. Y., which are both incorporated by reference herein in their entireties), to generate anti-LGALS3 antibodies or antigen-binding fragments thereof having a different amino acid sequence, for example, to create amino acid substitutions, deletions, and/or insertions. For example, such manipulations can be performed to render the encoded amino acid aglycosylated, or to destroy the antibody's ability to bind to Clq, Fc receptor, or to activate the complement system.

Isolated nucleic acid molecules provided herein can include nucleic acid molecules comprising an open reading frame (ORF), optionally with one or more introns, for example, but not limited to, at least one specified portion of at least one complementarity determining region (CDR), as CDR1, CDR2 and/or CDR3 of at least one heavy chain or light chain; nucleic acid molecules comprising the coding sequence for an anti-LGALS3 antibody or variable region; and nucleic acid molecules which comprise a nucleotide sequence substantially different from those described above but which, due to the degeneracy of the genetic code, still encode at least one anti-LGALS3 antibody or antigen-binding fragment thereof as described herein.

Also provided herein are isolated nucleic acids that hybridize under selective hybridization conditions to a poly-nucleotide disclosed herein. Thus, the polynucleotides of this embodiment can be used for isolating, detecting, and/or quantifying nucleic acids comprising such polynucleotides. For example, polynucleotides provided herein can be used to identify, isolate, or amplify partial or full-length clones in a deposited library. In some embodiments, the polynucle-otides are genomic or cDNA sequences isolated, or other-wise complementary to, a cDNA from a human or mamma-lian nucleic acid library.

The nucleic acids can conveniently comprise sequences in addition to a polynucleotide provided herein. For example, a multi-cloning site comprising one or more endonuclease restriction sites can be inserted into the nucleic acid to aid in isolation of the polynucleotide. In addition, translatable sequences can be inserted to aid in the isolation of the translated polynucleotide provided herein. For example, a hexa-histidine marker sequence (SEQ ID NO: 57) provides a convenient means to purify the polypeptides provided herein. The nucleic acid provided herein—excluding the coding sequence—is optionally a vector, adapter, or linker for cloning and/or expression of a polynucleotide provided herein.

Additional sequences can also be added to such cloning and/or expression sequences to optimize their function in cloning and/or expression, to aid in isolation of the poly-nucleotide, or to improve the introduction of the polynucle-otide into a cell. Use of cloning vectors, expression vectors, adapters, and linkers is well known in the art. (See, e.g., Ausubel, supra; or Sambrook, supra).

In a specific embodiment, using routine recombinant DNA techniques, one or more of the CDRs of an anti-LGALS3 antibody or antigen binding fragment thereof described herein can be inserted within known framework regions. The framework regions can be naturally occurring or consensus framework regions, and preferably human framework regions (see, e.g., Chothia et al., (1998) *J. Mol. Biol.* 278: 457-479 for a listing of human framework regions). In some embodiments, the polynucleotide gener-ated by the combination of the framework regions and CDRs encodes an anti-LGALS3 antibody or antigen binding fragment thereof that specifically binds LGALS3. One or more amino acid substitutions can be made within the framework regions, and, preferably, the amino acid substitutions improve binding of the antibody to its antigen. Additionally, such methods can be used to make amino acid substitutions or deletions of one or more variable region cysteine residues participating in an intrachain disulfide bond to generate antibody molecules lacking one or more intrachain disulfide bonds. Other alterations to the polynucleotide are provided herein and within the skill of the art.

In certain embodiments, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinant cloning techniques (see, for example, Gate-way™ (Invitrogen)). See, also, U.S. Pat. No. 5,314,995.

In certain embodiments, a polynucleotide provided herein is in the form of a vector (e.g., expression vector). In certain aspects, provided herein are polynucleotides comprising a nucleotide sequence encoding an anti-LGALS3 antibody or antigen binding fragment thereof described herein or an antigen-binding fragment thereof (e.g., a variable light chain region and/or variable heavy chain region) that specifically binds to LGALS3, and vectors, e.g., vectors comprising such polynucleotides for their efficient expression in host cells (e.g., *E. coli* and mammalian cells). In some embodi-ments, a polynucleotide is isolated or purified.

In particular aspects, provided herein are polynucleotides comprising nucleotide sequences encoding anti-LGALS3 antibodies or antigen binding fragments thereof and com-prise an amino acid sequence as described herein, as well as antibodies which compete with such antibodies for binding to LGALS3 (e.g., in a dose-dependent manner), or which binds to the same or an overlapping epitope as that of such antibodies.

In certain aspects, provided herein are polynucleotides comprising a nucleic acid sequence encoding the light chain or heavy chain of an anti-LGALS3 antibody or antigen binding fragment thereof described herein. The polynucle-otides can comprise nucleotide sequences encoding a heavy chain comprising the $V_H$ CDRs described herein (see, e.g., Table 6). The polynucleotides can comprise nucleotide sequences encoding a light chain comprising the $V_L$ CDRs described herein (see, e.g., Table 6).

In particular embodiments, provided herein are poly-nucleotides comprising a nucleotide sequence encoding an anti-LGALS3 antibody comprising three $V_H$ CDRs, e.g., containing $V_H$ CDR1, $V_H$ CDR2, and $V_H$ CDR3 as described in Table 6, wherein the antibody specifically binds to LGALS3. In specific embodiments, a polynucleotide described herein encodes a $V_H$ CDR1, a $V_H$ CDR2, and a $V_H$ CDR3 of the 46H02 antibody (i.e., SEQ ID NO: 7, SEQ ID NO: 8, and SEQ ID NO: 9, respectively), the 12H07 antibody (i.e., SEQ ID NO: 19, SEQ ID NO: 20, and SEQ ID NO: 21, respectively), the 20F08 antibody (i.e., SEQ ID NO: 29, SEQ ID NO: 30, and SEQ ID NO: 31, respectively), the 38E05 antibody (i.e., SEQ ID NO: 39, SEQ ID NO: 40, and SEQ ID NO: 41, respectively); or the 39F02 antibody (i.e., SEQ ID NO: 49, SEQ ID NO: 50, and SEQ ID NO: 51, respectively), wherein the antibody specifically binds to LGALS3. In certain embodiments, a polynucleotide described herein comprises a nucleotide sequence encoding an anti-LGALS3 antibody described herein comprising a heavy chain variable region that comprises an amino acid sequence described herein (e.g., SEQ ID NO: 6, SEQ ID NO: 18, SEQ ID NO: 28, SEQ ID NO: 38, or SEQ ID NO: 48), wherein the antibody specifically binds to LGALS3.

In particular embodiments, provided herein are polynucleotides comprising a nucleotide sequence encoding an anti-LGALS3 antibody comprising three $V_L$ CDRs, e.g., containing $V_L$ CDR1, $V_L$ CDR2, and $V_L$ CDR3 as described in Table 6, wherein the antibody specifically binds to LGALS3. In specific embodiments, a polynucleotide described herein encodes a $V_L$ CDR1, a $V_L$ CDR2, and a $V_L$ CDR3 of the 46H02 antibody (i.e., SEQ ID NO: 2, SEQ ID NO: 3, and SEQ ID NO: 4, respectively), the 12H07 antibody (i.e., SEQ ID NO: 14, SEQ ID NO: 15, and SEQ ID NO: 16, respectively), the 20F08 antibody (i.e., SEQ ID NO: 24, SEQ ID NO: 25, and SEQ ID NO: 26, respectively), the 38E05 antibody (i.e., SEQ ID NO: 34, SEQ ID NO: 35, and SEQ ID NO: 36, respectively); or the 39F02 antibody (i.e., SEQ ID NO: 44, SEQ ID NO: 45, and SEQ ID NO: 46, respectively), wherein the antibody specifically binds to LGALS3. In certain embodiments, a polynucleotide described herein comprises a nucleotide sequence encoding an anti-LGALS3 antibody described herein comprising a light chain variable region that comprises an amino acid sequence described herein (e.g., SEQ ID NO: 1, SEQ ID NO: 13, SEQ ID NO: 23, SEQ ID NO: 33, or SEQ ID NO: 43), wherein the antibody specifically binds to LGALS3.

In certain embodiments, a polynucleotide described herein comprises a nucleotide sequence encoding an anti-LGALS3 antibody described herein comprising a heavy chain variable region that comprises an amino acid sequence described herein (e.g., SEQ ID NO: 6, SEQ ID NO: 18, SEQ ID NO: 28, SEQ ID NO: 38, or SEQ ID NO: 48) and a light chain variable region that comprises an amino acid sequence described herein (e.g., SEQ ID NO: 1, SEQ ID NO: 13, SEQ ID NO: 23, SEQ ID NO: 33, or SEQ ID NO: 43), wherein the antibody specifically binds to LGALS3.

In specific aspects, provided herein is a polynucleotide comprising a nucleotide sequence encoding an anti-LGALS3 antibody or antigen binding fragment thereof comprising a light chain and a heavy chain, e.g., a separate light chain and heavy chain. With respect to the heavy chain, in a specific embodiment, a polynucleotide provided herein comprises a nucleotide sequence encoding an alpha (α), delta (δ), epsilon (ε), gamma (γ) or mu (μ) heavy chain. With respect to the light chain, in a specific embodiment, a polynucleotide provided herein comprises a nucleotide sequence encoding a kappa (κ) or a lambda (λ) light chain.

Cells and Vectors

In certain embodiments, provided herein are cells (e.g., isolated or ex vivo cells) expressing (e.g., recombinantly) one or more anti-LGALS3 antibodies or antigen-binding fragments thereof. Also provided herein are vectors (e.g., expression vectors) comprising nucleotide sequences encoding an anti-LGALS3 antibody or antigen-binding fragment thereof described herein for recombinant expression in host cells, preferably in mammalian cells. Also provided herein are cells (e.g., isolated or ex vivo cells) comprising such vectors or nucleotide sequences for recombinantly expressing an anti-LGALS3 antibody or antigen-binding fragment thereof described here. Also provided herein are methods for producing an anti-LGALS3 antibody or antigen-binding fragment thereof described herein, comprising expressing such anti-LGALS3 antibody or antigen-binding fragment thereof from a cell (e.g., isolated or ex vivo cells).

A vector (e.g., expression vector) is a DNA molecule comprising a gene that is expressed in a cell (e.g., ex vivo cell). Typically, gene expression is placed under the control of certain regulatory elements, including constitutive or inducible promoters, tissue-specific regulatory elements and enhancers. Such a gene is said to be "operably linked to" the regulatory elements, e.g., a promoter. A recombinant host can be any prokaryotic or eukaryotic cell that contains either a cloning vector or expression vector. This term also includes those prokaryotic or eukaryotic cells, as well as a transgenic animal, that have been genetically engineered to contain the cloned gene(s) in the chromosome or genome of the host cell or cells of the host cells (e.g., ex vivo cells). In one embodiment, the promoter is the CMV promoter.

In certain embodiments, provided herein is a vector comprising one or more polynucleotide as described herein. In certain embodiments, a polynucleotide as described herein can be cloned into a suitable vector and can be used to transform or transfect any suitable host. Vectors and methods to construct such vectors are known to one of ordinary skill in the art and are described in general technical references (see, in general, "Recombinant DNA Part D," Methods in Enzymology, Vol. 153, Wu and Grossman, eds., Academic Press (1987)). In certain embodiments, the vector comprises regulatory sequences, such as transcription and translation initiation and termination codons, which are specific to the type of host (e.g., bacterium, fungus, plant, insect, or mammal) into which the vector is to be introduced, as appropriate and taking into consideration whether the vector is DNA or RNA. In certain embodiments, the vector comprises regulatory sequences that are specific to the genus of the host. In certain embodiments, the vector comprises regulatory sequences that are specific to the species of the host. In certain embodiments, the vector comprises one or more marker genes, which allow for selection of transformed or transfected hosts. Non-limiting examples of marker genes include biocide resistance, e.g., resistance to antibiotics, heavy metals, etc., complementation in an auxotrophic host to provide prototrophy, and the like. In a particular embodiment, the vector comprises ampicillin and hygromycin selectable markers.

In certain embodiments, an expression vector can comprise a native or normative promoter operably linked to a polynucleotide as described herein. The selection of promoters, for example, strong, weak, inducible, tissue-specific and developmental-specific, is within the skill in the art. Similarly, the combining of a nucleic acid molecule, or fragment thereof, as described above with a promoter is also within the skill in the art.

Non-limiting examples of suitable vectors include those designed for propagation and expansion or for expression or both. For example, a cloning vector can be selected from the group consisting of the pUC series, the pBluescript series (Stratagene, LaJolla, Calif), the pET series (Novagen, Madison, Wis.), the pGEX series (Pharmacia Biotech, Uppsala, Sweden), and the pEX series (Clontech, Palo Alto, Calif). Bacteriophage vectors, such as lamda-GTIO, lamda-GT1 1, lamda-ZapII (Stratagene), lamda-EMBL4, and lamda-NMl 149, can also be used. Non-limiting examples of plant expression vectors include pBIl 10, pBI101.2, pBI101.3, pBI121 and pBIN19 (Clontech). Non-limiting examples of animal expression vectors include pEUK-Cl, pMAM and pMAMneo (Clontech). The TOPO cloning system (Invitrogen, Carlsbad, Calif.) can also be used in accordance with the manufacturer's recommendations.

In certain embodiments, the vector is a mammalian vector. In certain embodiments, the mammalian vector contains at least one promoter element, which mediates the initiation of transcription of mRNA, the anti-LGALS3 antibody or antigen-binding fragment thereof coding sequence, and signals required for the termination of transcription and polyadenylation of the transcript. In certain embodiments, the mammalian vector contains additional elements, such as, for example, enhancers, Kozak sequences and intervening sequences flanked by donor and acceptor sites for RNA splicing. In certain embodiments, highly efficient transcription can be achieved with, for example, the early and late promoters from SV40, the long terminal repeats (LTRS) from retroviruses, for example, RSV, HTLVI, HIVI and the early promoter of the cytomegalovirus (CMV). However, cellular elements can also be used (e.g., the human actin promoter). Non-limiting examples of mammalian expression vectors include, vectors such as pIRESlneo, pRetro-Off, pRetro-On, PLXSN, or pLNCX (Clonetech Labs, Palo Alto, Calif), pcDNA3.1 (+/−), pcDNA/Zeo (+/−) or pcDNA3.1/ Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Non-limiting example of mammalian host cells that can be used in combination with such mammalian vectors include human Hela 293, H9 and Jurkat cells, mouse NIH3T3 and C127 cells, Cos 1, Cos 7 and CV 1, quail QCl-3 cells, mouse L cells and Chinese hamster ovary (CHO) cells.

In certain embodiments, the vector is a viral vector, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. In certain embodiments, the viral vector is manipulated to render the virus replication deficient. In certain embodiments, the viral vector is manipulated to eliminate toxicity to the host. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

In certain embodiments, a vector or polynucleotide described herein can be transferred to a cell (e.g., an ex vivo cell) by conventional techniques and the resulting cell can be cultured by conventional techniques to produce an anti-LGALS3 antibody or antigen-binding fragment thereof described herein. Accordingly, provided herein are cells comprising a polynucleotide encoding an anti-LGALS3 antibody or antigen-binding fragment thereof, a heavy or light chain thereof, or a light chain fusion polypeptide thereof, operably linked to a promoter for expression of such sequences in the host cell. In certain embodiments, a vector encoding the heavy chain operably linked to a promoter and a vector encoding the light chain operably linked to a promoter can be co-expressed in the cell for expression of the entire anti-LGALS3 antibody. In certain embodiments, a vector encoding a heavy chain operably linked to a promoter and a vector encoding a light chain fusion polypeptide operably linked to a promoter can be co-expressed in the cell for expression of an entire bispecific binding molecule. In certain embodiments, a cell comprises a vector comprising a polynucleotide encoding both the heavy chain and the light chain polypeptide of an anti-LGALS3 antibody described herein operably linked to a promoter. In certain embodiments, a cell comprises a vector comprising a polynucleotide encoding both the heavy chain and the light chain fusion polypeptide of a bispecific binding molecule described herein operably linked to a promoter. In certain embodiments, a cell comprises two different vectors, a first vector comprising a polynucleotide encoding a heavy chain operably linked to a promoter, and a second vector comprising a polynucleotide encoding a light chain polypeptide operably linked to a promoter. In certain embodiments, a cell comprises two different vectors, a first vector comprising a polynucleotide encoding a heavy chain operably linked to a promoter, and a second vector comprising a polynucleotide encoding a light chain fusion polypeptide operably linked to a promoter. In certain embodiments, a first cell comprises a first vector comprising a polynucleotide encoding a heavy chain of an anti-LGALS3 antibody described herein, and a second cell comprises a second vector comprising a polynucleotide encoding a light chain polypeptide of an anti-LGALS3 antibody described herein. In certain embodiments, provided herein is a mixture of cells comprising such first cell and such second cell. In certain embodiments, a first cell comprises a first vector comprising a polynucleotide encoding a heavy chain of a bispecific binding molecule described herein, and a second cell comprises a second vector comprising a polynucleotide encoding a light chain fusion polypeptide of a bispecific binding molecule described herein. In certain embodiments, provided herein is a mixture of cells comprising such first cell and such second cell. In a particular embodiment, the cell expresses the vector or vectors such that the polynucleotide is both transcribed and translated efficiently by the cell.

In some embodiments, the cell expresses the vector, such that the polynucleotide, or fragment thereof, is both transcribed and translated efficiently by the cell.

In certain embodiments, the cell is present in a host, which can be an animal, such as a mammal. Examples of cells include, but are not limited to, a human cell, a human cell line, E. coli (e.g., E. coli TB-1, TG-2, DH5a, XL-Blue MRF (Stratagene), SA2821 and Y1090), B. subtilis, P. aerugenosa, S. cerevisiae, N. crassa, insect cells (e.g., Sf9, Ea4) and others set forth herein below. In a particular embodiment, the cell is a CHO cell. In another particular embodiment, the cell is a CHO-S cell.

In certain embodiments, a polynucleotide described herein can be expressed in a stable cell line that comprises the polynucleotide integrated into a chromosome by introducing the polynucleotide into the cell. In certain embodiments, the polynucleotide is introduced into the cell by, for example, electroporation. In certain embodiments, the polynucleotide is introduced into the cell by, for example, transfection of a vector comprising the polynucleotide into the cell. In certain embodiments, the vector is co-transfected with a selectable marker such as DHFR, GPT, neomycin, or hygromycin to allow for the identification and isolation of the transfected cells. In certain embodiments, the transfected polynucleotide can also be amplified to express large amounts of the encoded anti-LGALS3 antibody or antigen-binding fragment thereof. For example, the DHFR (dihydrofolate reductase) marker can be utilized to develop cell lines that carry several hundred or even several thousand copies of the polynucleotide of interest. Another example of a selection marker is the enzyme glutamine synthase (GS) (Murphy, et al., Biochem. J. 227:277-279 (1991); Bebbington, et al., Bio/Technology 10: 169-175). Using these markers, the cells are grown in selective medium and the cells with the highest resistance are selected. These cell lines contain the amplified gene(s) integrated into a chromosome. Chinese hamster ovary (CHO) and NSO cells are often used for the production of antibodies.

In some embodiments, the vector comprises (i) a first polynucleotide sequence encoding an immunoglobulin light chain that binds to LGALS3, operably linked to a first promoter and (ii) a second polynucleotide encoding an immunoglobulin heavy chain that binds to LGALS3, operably linked to a second promoter. In certain embodiments, the vector is a viral vector.

In some embodiments, the vector comprises (i) a first polynucleotide sequence encoding a light chain fusion polypeptide comprising an immunoglobulin light chain fused to a scFv, via a peptide linker, wherein the light chain binds to LGALS3 and wherein the scFv binds to CD3, operably linked to a first promoter and (ii) a second polynucleotide encoding an immunoglobulin heavy chain that binds to LGALS3 operably linked to a second promoter. In certain embodiments, the vector is a viral vector.

Pharmaceutical Compositions

In certain embodiments, provided herein are compositions (e.g., pharmaceutical compositions) and kits comprising a pharmaceutically effective amount of one or more anti-LGALS3 antibodies or antigen-binding fragments thereof. In certain embodiments, the pharmaceutical compositions comprise immune cells, for example T cells, recombinantly expressing an antibody, antigen-binding fragment thereof, and/or CAR described herein. Compositions can be used in the preparation of individual, single unit dosage forms. Compositions provided herein can be formulated for parenteral, subcutaneous, intramuscular, intravenous, intrarticular, intrabronchial, intraabdominal, intracapsular, intracartilaginous, intracavitary, intracelial, intracelebellar, intracerebroventricular, intra-Ommaya, intraocular, intravitreous, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, intrathecal, intraventricular in the brain, intraparenchymal in the brain, or transdermal administration.

In certain embodiments, provided herein is a composition comprising one or more polynucleotide comprising nucleotide sequences encoding an anti-LGALS3 antibody or an antigen-binding fragment thereof described herein. In certain embodiments, provided herein is a composition comprising a cell, wherein the cell comprises one or more polynucleotides comprising nucleotide sequences encoding an anti-LGALS3 antibody or an antigen-binding fragment thereof described herein. In certain embodiments, provided herein is a composition comprising a vector, wherein the vector comprises one or more polynucleotide comprising nucleotide sequences encoding an anti-LGALS3 antibody or an antigen-binding fragment thereof described herein. In certain embodiments, provided herein is a composition comprising a cell, wherein the cell comprises a vector, wherein the vector comprises one or more polynucleotide comprising nucleotide sequences encoding an anti-LGALS3 antibody or an antigen-binding fragment thereof described herein.

In certain embodiments, a composition described herein is a stable or preserved formulation. In certain embodiments, the stable formulation comprises a phosphate buffer with saline or a chosen salt. In certain embodiments, a composition described is a multi-use preserved formulation, suitable for pharmaceutical or veterinary use. In certain embodiments, a composition described herein comprises a preservative. Preservatives are known to one of ordinary skill in the art. Non-limiting examples of preservatives include phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, and sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9%, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

It can be desirable to deliver the compositions provided herein to a subject over prolonged periods of time, for example, for periods of one week to one year or more from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, a composition provided herein, preferably, a relatively insoluble salt such as those just described, can be formulated in a gel, for example, an aluminum monostearate gel with, e.g., sesame oil, suitable for injection. Particularly particular salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer, for example, as described in U.S. Pat. No. 3,773,919. The compounds or, preferably, relatively insoluble salts such as those described above can also be formulated in cholesterol matrix silastic pellets, particularly for use in animals. Additional slow release, depot or implant compositions, e.g., gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

The range of at least one anti-LGALS3 antibody or antigen-binding fragment thereof composition provided herein includes amounts yielding upon reconstitution, if in a wet/dry system, concentrations from about 1.0 microgram/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

In certain embodiments, compositions provided herein comprise at least one of any suitable auxiliary, such as, but not limited to, diluent, binder, stabilizer, buffers, salts, lipophilic solvents, preservative, adjuvant or the like. In certain embodiments, pharmaceutically acceptable auxiliaries are particular. Non-limiting examples of, and methods of preparing such sterile solutions are well known in the art, such as, but not limited to, Gennaro, Ed., Remington's Pharmaceutical Sciences, 18th Edition, Mack Publishing Co. (Easton, Pa.) 1990.

Pharmaceutically acceptable carriers can be routinely selected that are suitable for the mode of administration, solubility and/or stability of the anti-LGALS3 antibody or antigen-binding fragment thereof described herein.

In certain embodiments, compositions provided herein contain one or more pharmaceutical excipient and/or additive. Non-limiting examples of pharmaceutical excipients and additives are proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Non-limiting examples of protein excipients include serum albumin such as human serum albumin (HSA), recombinant human albumin (rHA), gelatin, casein, and the like. Non-limiting examples of amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. In certain embodiments, the amino acid is glycine. Non-limiting examples of carbohydrate excipients include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. In certain embodiments, the carbohydrate excipient is mannitol, trehalose, or raffinose.

In certain embodiments, a composition provided herein includes one or more buffer or a pH adjusting agent; typically, the buffer is a salt prepared from an organic acid or base. Non-limiting examples of buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In certain embodiments, the buffer is an organic acid salts such as citrate. Other excipients, e.g., isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The compositions can cover a wide range of pHs, such as from about pH 4 to about pH 10, and particular ranges from about pH 5 to about pH 9, and a most particular range of about 6.0 to about 8.0. In some embodiments, the compositions provided herein have pH between about 6.8 and about 7.8. Preferred buffers include phosphate buffers, most preferably sodium phosphate, particularly phosphate buffered saline (PBS).

In certain embodiments, a composition provided herein includes one or more polymeric excipient/additive such as, for example, polyvinylpyrrolidones, ficolls (a polymeric sugar), dextrates (e.g., cyclodextrins, such as 2-hydroxypropyl-.beta.-cyclodextrin), polyethylene glycols, flavoring agents, antimicrobial agents, sweeteners, antioxidants, antistatic agents, surfactants (e.g., polysorbates such as "TWEEN 20" and 'TWEEN 80"), lipids (e.g., phospholipids, fatty acids), steroids (e.g., cholesterol), and/or chelating agents (e.g., EDTA).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or nonionic surfactants such as polysorbate 20 or 80 or poloxamer 184 or 188, Pluronic® polyols, other block co-polymers, and chelators such as EDTA and EGTA can optionally be added to the compositions to reduce aggregation. These additives are particularly useful if a pump or plastic container is used to administer the composition. The presence of pharmaceutically acceptable surfactant mitigates the propensity for the protein to aggregate.

Additional pharmaceutical excipients and/or additives suitable for use in a composition provided herein are known to one of skill in the art and are referenced in, for example, "Remington: The Science & Practice of Pharmacy", 19.sup.th ed., Williams & Williams, (1995), and in the "Physician's Desk Reference", 52nd ed., Medical Economics, Montvale, N.J. (1998), which are entirely incorporated herein by reference. In certain particular embodiments, the carrier or excipient materials are carbohydrates (e.g., saccharides and alditols) and buffers (e.g., citrate) or polymeric agents.

In some embodiments, the aqueous diluent optionally further comprises a pharmaceutically acceptable preservative. Exemplary preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the composition is a concentration sufficient to yield an anti-microbial effect. Such concentrations are dependent on the preservative selected and are readily determined by the skilled artisan.

The compositions provided herein can be prepared by a process which comprises mixing at least one anti-LGALS3 antibody or antigen-binding fragment thereof described herein and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-LGALS3 antibody or antigen-binding fragment thereof described herein and preservative in an aqueous diluent is carried out using conventional dissolution and mixing procedures. To prepare a suitable composition, for example, a measured amount of at least one anti-LGALS3 antibody or antigen-binding fragment thereof described herein in buffered solution is combined with the desired preservative in a buffered solution in quantities sufficient to provide the anti-LGALS3 antibody or antigen-binding fragment thereof described herein and preservative at the desired concentrations. The compositions provided herein can be prepared by a process that comprises mixing at least one anti-LGALS3 antibody or antigen-binding fragment thereof described herein and a selected buffer, preferably a phosphate buffer containing saline or a chosen salt. Mixing the at least one anti-LGALS3 antibody or antigen-binding fragment thereof described herein and buffer in an aqueous diluent is carried out using conventional dissolution and mixing procedures. To prepare a suitable composition, for example, a measured amount of at least one anti-LGALS3 antibody or antigen-binding fragment thereof described herein in water or buffer is combined with the desired buffering agent in water in quantities sufficient to provide the protein and buffer at the desired concentrations. Variations of these processes would be recognized by one of ordinary skill in the art. For example, the order the components are added, whether additional additives are used, the temperature and pH at which the composition is prepared, are all factors that can be optimized for the concentration and means of administration used.

Parenteral Formulations

In certain embodiments, a composition provided herein is formulated for parenteral injectable administration. As used herein, the term "parenteral" includes intravenous, intravascular, intramuscular, intradermal, subcutaneous, and intraocular. For parenteral administration, the composition can be formulated as a solution, suspension, emulsion or lyophilized powder in association, or separately provided, with a pharmaceutically acceptable parenteral vehicle. Non-limiting examples of such vehicles are water, saline, Ringer's solution, dextrose solution, glycerol, ethanol, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Pulmonary Formulations

In certain embodiments, a composition comprising an anti-LGALS3 antibody or an antigen-binding fragment thereof described herein is formulated for pulmonary administration. For pulmonary administration, the composition is delivered in a particle size effective for reaching the lower airways of the lung or sinuses.

Compositions for pulmonary administration can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of an anti- LGALS3 antibody or an antigen-binding fragment thereof described herein are also known in the art. All such devices use formulations suitable for the administration for the dispensing of an anti-LGALS3 antibody or an antigen-binding fragment thereof described herein in an aerosol. Such aerosols can be comprised of either solution (both aqueous and nonaqueous) or solid particles. Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler®. (Glaxo), Diskus® (Glaxo), devices marketed by Inhale Therapeutics, to name a few, use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference).

Nebulizers like the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. Such examples of commercially available inhalation devices are non-limiting examples are not intended to be limiting in scope.

In certain embodiments, a spray comprising an anti-LGALS3 antibody or an antigen-binding fragment thereof described herein can be produced by forcing a suspension or solution of at least one anti-LGALS3 antibody or antigen-binding fragment thereof described herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of a composition comprising at least one anti-LGALS3 antibody or antigen-binding fragment thereof described herein delivered by a sprayer have a particle size less than about 10 μm, for example in the range of about 1 μm to about 5 μm, for example about 2 μm to about 3 μm.

Formulations of a composition comprising at least one anti-LGALS3 antibody or antigen-binding fragment thereof described herein suitable for use with a sprayer typically include the at least one anti-LGALS3 antibody or antigen-binding fragment thereof described herein in an aqueous solution at a concentration of about 0.1 mg to about 100 mg per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the anti-LGALS3 antibody or antigen-binding fragment thereof composition, such as a buffer, a reducing agent, a bulk protein, or a carbohydrate. Bulk proteins useful in formulating such a composition include albumin, protamine, or the like. Typical carbohydrates useful in formulating antibody composition proteins include sucrose, mannitol, lactose, trehalose, glucose, or the like. The composition can also include a surfactant, which can reduce or prevent surface-induced aggregation of the composition caused by atomization of the solution in forming an aerosol. Various conventional surfactants can be employed, such as polyoxyethylene fatty acid esters and alcohols, and polyoxy ethylene sorbitol fatty acid esters. Amounts will generally range between 0.001 and 14% by weight of the formulation. Preferred surfactants are polyoxyethylene sorbitan monooleate, polysorbate 80, polysorbate 20, or the like.

In certain embodiments, the composition is administered via a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of anti-body composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 um, preferably in the range of about 1 um to about 5 um, and most preferably about 2 um to about 3 um.

In certain embodiments, the composition is administered via a metered dose inhaler (MDI), wherein a propellant, at least one anti-LGALS3 antibody or antigen-binding fragment thereof described herein, and any excipients or other additives are contained in a canister as a mixture including a liquefied compressed gas.

Actuation of the metering valve releases die mixture as an aerosol, preferably containing particles in the size range of less than about 10 um, preferably about 1 um to about 5 um, and most preferably about 2 um to about 3 um. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of an anti-LGALS3 antibody or an antigen-binding fragment thereof described herein for use with a metered-dose inhaler device will generally include a finely divided powder containing at least one Anti-IL-6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1, 1,1,2-tetrafluoroethane, HFA-134a (hydrofluoroalkane-134a), HFA-227 (hydrofluoroalkane-227), or the like. In some embodiments, the propellant is a hydrofluorocarbon. The surfactant can be chosen to stabilize the at least one anti-LGALS3 antibody or antigen-binding fragment thereof described herein as a suspension in the propellant, to protect the active agent against chemical degradation, and the like. Suitable surfactants include sorbitan trioleate, soya lecithin, oleic acid, or the like. In some cases, solution aerosols are particular using solvents such as ethanol.

Additional agents known in the art for formulation of a protein can also be included in the formulation.

Oral Formulations

In certain embodiments, a composition provided herein is formulated for oral administration. In certain embodiments, for oral administration, compositions and methods of administering at least one anti-LGALS3 antibody or antigen-binding fragment thereof described herein rely on the co-administration of adjuvants such as, for example, resorcinols and nonionic surfactants such as polyoxyethylene oleyl ether and n-hexadecylpolyethylene ether, to artificially increase the permeability of the intestinal walls, as well as the co-administration of enzymatic inhibitors such as, for example, pancreatic trypsin inhibitors, diisopropylfluorophosphate (DFF) and trasylol, to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, such as, for example, inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

In certain embodiments, tablets and pills for oral administration can be further processed into enteric-coated preparations. In certain embodiments, liquid preparations for oral administration include, for example, emulsion, syrup, elixir, suspension and solution preparations allowable for medical use. These preparations can contain inactive diluting agents ordinarily used in said field, for example, water. Liposome preparations can be utilized for oral administration preparations, for example, as described for insulin and heparin (U.S. Pat. No. 4,239,754). Additionally, microspheres of artificial polymers of mixed amino acids (proteinoids) can be utilized to in oral administration of pharmaceuticals, for example, as described in U.S. Pat. No. 4,925,673. Furthermore, carrier compounds, such as those described in U.S. Pat. Nos. 5,879,681 and 5,871,753, are used in oral administration of biologically active agents.

Mucosal Formulations

In certain embodiments, a composition provided herein is formulated for absorption through mucosal surfaces. In certain embodiments, for absorption through mucosal surfaces, compositions and methods of administering at least one anti-LGALS3 antibody or antigen-binding fragment thereof described herein include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions provided herein can include, for example, corneal, conjunctival, buccal, sublingual, nasal, vaginal, pulmonary, stomachic, intestinal, and rectal routes of administration. Formulations for vaginal or rectal administration, for example, suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include, for example, sugars, calcium stearate, magnesium stearate, pregelinatined starch, and the like (U.S. Pat. No. 5,849,695).

Transdermal Formulations

In certain embodiments, a composition provided herein is formulated for transdermal administration. In certain embodiments, for transdermal administration, the composition comprises at least one anti-LGALS3 antibody or antigen-binding fragment thereof described herein encapsulated in a delivery device such as, for example, a liposome or polymeric nanoparticles, microparticle, microcapsule, or microspheres (referred to collectively as microparticles unless otherwise stated). A number of suitable devices are known for transdermal administration, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814, 599).

Kits

Also disclosed herein are kits for the detection and/or treatment of a Galectin-3-associated disease or condition (e.g., Galectin-3-associated cancers, cardiovascular disease, fibrosis, rheumatic diseases, and inflammation) comprising at least one immunoglobulin-related composition of the present technology (e.g., any of the antibodies, antigen-binding fragments, antibody conjugates, bispecific antibodies or antibody conjugates, scFvs, scFv conjugates, CARs, T cells, recombinant nucleic acid sequences, vectors, or isolated cells described herein described herein), and instructions for use. In certain embodiments, the immunoglobulin-related composition is coupled to one or more detectable labels. In one embodiment, the one or more detectable labels comprise a radioactive label, a fluorescent label, or a chromogenic label. Additionally or alternatively, in some embodiments, the kit further comprises a secondary antibody that specifically binds to an immunoglobulin-related composition described herein. In some embodiments, the secondary antibody is coupled to at least one detectable label selected from the group consisting of a radioactive label, a fluorescent label, or a chromogenic label.

In a specific embodiment, provided herein is a pharmaceutical pack or kit comprising one or more containers filled with one or more of the ingredients of the pharmaceutical compositions described herein, such as one or more antibodies or an antigen-binding fragment thereof described herein. In some embodiments, the kits contain a pharmaceutical composition described herein and a prophylactic or therapeutic agent.

Optionally associated with such container(s) can be a notice in the form prescribed by a governmental agency regulating the manufacture, use or sale of pharmaceuticals or biological products, a dosage form, and/or instructions for use thereof. In certain embodiments, the instructions included with the kit provide guidance with respect to the dosage amounts and/or dosing regimens for administration of the pharmaceutical composition(s).

Examples of pharmaceutical packaging materials include, but are not limited to, blister packs, bottles, packets, sachets, tubes, inhalers, pumps, bags, vials, containers, syringes and any packaging material suitable for a selected pharmaceutical composition and intended mode of administration and treatment.

Kits provided herein can further include devices that are used to administer the active ingredients. Examples of such devices include, but are not limited to, syringes, needle-less injectors, drip bags, patches and inhalers.

Kits provided herein can further include pharmaceutically acceptable vehicles that can be used to administer the ingredients. For example, if an ingredient is provided in a solid form that must be reconstituted for parenteral administration, the kit can comprise a sealed container of a suitable vehicle in which the ingredient can be dissolved to form a particulate-free sterile solution that is suitable for parenteral administration or can be reconstituted as a suspension for oral administration. Examples of pharmaceutically acceptable vehicles include, but are not limited to: aqueous vehicles including, but not limited to, Water for Injection USP, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol, and polypropylene glycol; and non-aqueous vehicles including, but not limited to, corn oil, cottonseed oil, peanut oil, sesame oil, ethyl oleate, isopropyl myristate, and benzyl benzoate.

Uses and Methods

Therapeutic Uses and Methods

In certain embodiments, provided herein are methods for treating a LGALS3-related disease or condition comprising administering to the subject in need thereof a therapeutically effective amount of an anti-LGALS3 antibody or antigen-binding fragment thereof. Exemplary LGALS3-related disease or conditions include, but are not limited to, cancer, tumor metastasis, tumor angiogenesis, heart failure, pulmonary fibrosis, glomerular disease of the kidney, inflammatory disease, and rheumatic diseases.

In a specific embodiment, the anti-LGALS3 antibody or antigen-binding fragment thereof is administered in combination with one or more additional therapeutic agents. In some embodiments, the one or more additional therapeutic agents inhibit or treat one or more symptoms of the LGALS3-related disease or condition.

In certain embodiments, provided herein are methods for treating cancer in a subject, in particular, a LGALS3-positive cancer in a subject, comprising administering to the subject in need thereof a therapeutically effective amount of an anti-LGALS3 antibody or antigen-binding fragment thereof. In a specific embodiment, the LGALS3-positive cancer is ovarian cancer, lung cancer, pancreatic cancer, breast cancer, fallopian tube cancer, uterine (e.g., endometrial) cancer, primary peritoneum cancer or cancer of any other tissue that expresses LGALS3.

For use of an anti-LGALS3 antibody or fragment thereof in a subject of a particular species, an anti-LGALS3 antibody or fragment thereof is used that binds to LGALS3 of that particular species. For example, to treat a human, an anti-LGALS3 antibody or antigen-binding fragment thereof is used that binds to human LGALS3. In a specific embodiment, the anti-LGALS3 antibody or antigen-binding fragment thereof is an immunoglobulin.

In addition, for use of an anti-LGALS3 antibody or fragment thereof in a subject of a particular species, the anti-LGALS3 antibody, in certain embodiments, the constant region of an anti-LGALS3 antibody or antigen binding fragment thereof, is derived from that particular species. For example, to treat a human, the anti-LGALS3 antibody or fragment thereof can comprise an anti-LGALS3 antibody or antigen binding fragment thereof that is an immunoglobulin, wherein the immunoglobulin comprises a human constant region. In a specific embodiment, the subject is a human.

In specific embodiments, treatment can be to achieve beneficial or desired clinical results including, but not limited to, alleviation of a symptom, diminishment of extent of a disease, stabilizing (i.e., not worsening) of state of a disease, delay or slowing of disease progression, amelioration or palliation of the disease state, and remission (whether partial or total), whether detectable or undetectable. In a specific embodiment, "treatment" can also be to prolong survival as compared to expected survival if not receiving treatment. In specific embodiments, the administration of an anti-LGALS3 antibody or antigen binding fragment thereof described herein, or a pharmaceutical composition described herein to a subject with cancer (e.g., ovarian cancer, lung cancer, pancreatic cancer, breast cancer, fallopian tube cancer, uterine (e.g., endometrial) cancer, or primary peritoneum cancer, or cancer of any other tissue that expresses LGALS3) achieves at least one, two, three, four or more of the following effects: (i) the reduction or amelioration of the severity of one or more symptoms of cancer; (ii) the reduction in the duration of one or more symptoms associated with cancer; (iii) the prevention in the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) the inhibition of the development or onset of one or more symptoms associated with cancer; (ix) the reduction in the number of symptoms associated with cancer; (x) improvement in quality of life as assessed by methods well known in the art; (x) inhibition of the recurrence of a tumor; (xi) the regression of tumors and/or one or more symptoms associated therewith; (xii) the inhibition of the progression of tumors and/or one or more symptoms associated therewith; (xiii) a reduction in the growth of a tumor; (xiv) a decrease in tumor size (e.g., volume or diameter); (xv) a reduction in the formation of a newly formed tumor; (xvi) prevention, eradication, removal, or control of primary, regional and/or metastatic tumors; (xvii) a decrease in the number or size of metastases; (xviii) a reduction in mortality; (xix) an increase in relapse free survival; (xx) the size of the tumor is maintained and does not increase or increases by less than the increase of a tumor after administration of a standard therapy as measured by conventional methods available to one of skill in the art, such as magnetic resonance imaging (MM), dynamic contrast-enhanced MM (DCE-MRI), X-ray, and computed tomography (CT) scan, or a positron emission tomography (PET) scan; and/or (xxi) an increase in the length of remission in patients. Treatment can be to achieve one or more of the foregoing.

Diagnostic Uses

In certain embodiments, anti-LGALS3 antibodies or antigen-binding fragments thereof described herein can be used for diagnostic purposes to detect, diagnose, or monitor a condition described herein (e.g., a condition involving LGALS3-positive cancer cells). In certain embodiments, anti-LGALS3 antibodies or antigen-binding fragments thereof for use in diagnostic purposes are labeled.

In certain embodiments, provided herein are methods for the detection of a condition described herein comprising (a) assaying the expression of LGALS3 or a fragment thereof in cells or a tissue sample of a subject using one or more anti-LGALS3 antibodies or antigen-binding fragments thereof described herein; and (b) comparing the level of LGALS3 or the fragment thereof expression with a control level, for example, levels in normal tissue samples (e.g., from a subject not having a condition described herein, or from the same patient before onset of the condition), whereby an increase or decrease in the assayed level of LGALS3 or the fragment thereof expression compared to the control level of LGALS3 or the fragment thereof expression is indicative of a condition described herein.

Antibodies described herein can be used to assay the levels of LGALS3 or a fragment thereof in a biological sample using classical immunohistological methods as described herein or as known to those of skill in the art (e.g., see Jalkanen et al., 1985, J. Cell. Biol. 101:976-985; and Jalkanen et al. (1987) J Cell. Biol. 105:3087-3096). Other antibody-based methods useful for detecting protein gene expression include immunoassays, such as the enzyme linked immunosorbent assay (ELISA) and the radioimmunoassay (MA). Suitable antibody assay labels are known in the art and include enzyme labels, such as, glucose oxidase; radioisotopes, such as iodine ($^{125}$I, 121I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

In certain embodiments, monitoring of a condition described herein (e.g., a LGALS3-positive cancer), is carried out by repeating the method for diagnosing for a period of time after initial diagnosis.

Presence of the labeled molecule can be detected in the subject using methods known in the art for in vivo scanning. Skilled artisans will be able to determine the appropriate method for detecting a particular label. Methods and devices that can be used in the diagnostic methods of the present disclosure include, but are not limited to, computed tomography (CT), whole body scan such as position emission tomography (PET), magnetic resonance imaging (MRI), and sonography.

Doses and Regimens

An anti-LGALS3 antibody or antigen-binding fragment thereof, or composition, or cells expressing the antibodies, or antigen-binding fragments thereof, described herein can be delivered to a subject by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray. In one embodiment, an anti-LGALS3 antibody or antigen-binding fragment thereof, or a composition described herein is administered parenterally to a subject. In a specific embodiment, said parenteral administration is intravenous, intramuscular, or subcutaneous.

The amount of an anti-LGALS3 antibody or antigen-binding fragment thereof, or composition which will be effective in the treatment and/or prevention of a condition will depend on the nature of the disease, and can be determined by standard clinical techniques.

The precise dose to be employed in a composition will also depend on the route of administration, and the type of cancer, and should be decided according to the judgment of the practitioner and each subject's circumstances. For example, effective doses may also vary depending upon means of administration, target site, physiological state of the patient (including age, body weight and health), whether the patient is human or animal, other medications administered, or whether treatment is prophylactic or therapeutic. Treatment dosages are optimally titrated to optimize safety and efficacy.

In certain embodiments, an in vitro assay is employed to help identify optimal dosage ranges. Effective doses can be extrapolated from dose response curves derived from in vitro or animal model test systems.

For an anti-LGALS3 antibody or antigen binding fragment thereof, the dosage can range from about 0.0001 to 100 mg/kg, and more usually 0.01 to 15 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. Generally, human antibodies have a longer half-life within the human body than antibodies from other species due to the immune response to the foreign polypeptides. Thus, lower dosages of human antibodies and less frequent administration is often possible.

In certain embodiments, such as in the administration of engineered cells expressing the antibodies or antigen-binding fragments thereof, or CARs, a subject is administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges. In some embodiments, the dose of total cells and/or dose of individual sub-populations of cells is within a range of between at or about $10^4$ and at or about $10^9$ cells/kilograms (kg) body weight, such as between $10^5$ and $10^6$ cells/kg body weight, for example, at or about $1{\times}10^5$ cells/kg, $1.5{\times}10^5$ cells/kg, $2{\times}10^5$ cells/kg, or $1{\times}10^6$ cells/kg, $2{\times}10^6$ cells/kg, $5{\times}10^6$ cells/kg, or $10{\times}10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^7$ T cells/kg body weight.

An anti-LGALS3 antibody or antigen-binding fragment thereof can be administered on multiple occasions. Intervals between single dosages can be, for example, 1 week, 2 weeks, 3 weeks, 4 weeks, 1 month, 2 months, 3 months, 6 months, 1 year, or 2 years.

Combination Therapies

In a specific embodiment, the methods provided herein for treating cancer (e.g., ovarian cancer, pancreatic cancer, lung cancer, breast cancer, fallopian tube cancer, uterine (e.g., endometrial) cancer, or primary peritoneum cancer) in a subject, comprising administering to a subject in need thereof a pharmaceutical composition comprising an anti-LGALS3 antibody or an antigen-binding fragment thereof described herein, further comprise administering to the subject one or more additional therapeutic agents. In a specific embodiment, the additional therapeutic agent is for treating the cancer in the subject (e.g., ovarian cancer, pancreatic cancer, lung cancer, breast cancer, fallopian tube cancer, uterine (e.g., endometrial) cancer, and primary peritoneum cancer). In a specific embodiment, the additional therapeutic agent is for treating any side effects of treatment with an anti-LGALS3 antibody or an antigen-binding fragment described herein described herein.

In specific embodiments, the additional agent is an agent used to treat ovarian cancer. In specific embodiments, the additional agent is an agent used to treat pancreatic cancer. In specific embodiments, the additional agent is an agent used to treat lung cancer. In specific embodiments, the additional agent is an agent used to treat breast cancer. In specific embodiments, the additional agent is an agent used to treat fallopian tube cancer. In specific embodiments, the additional agent is an agent used to treat uterine (e.g., endometrial) cancer. In specific embodiments, the additional agent is an agent used to treat primary peritoneum cancer.

An anti-LGALS3 antibody or an antigen-binding fragment thereof described herein described herein can be administered with an additional therapeutic agent concurrently or sequentially (before and/or after). The antibody or antigen binding fragment thereof and the additional therapeutic agent can be administered in the same or different compositions, and by the same or different routes of administration. A first therapy (which is an anti-LGALS3 antibody or an antigen-binding fragment thereof described herein, or the additional therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second therapy (the anti-LGALS3 antibody or antigen-binding fragment thereof described herein described herein, or the additional therapeutic agent) to a subject with cancer (e.g., ovarian cancer, pancreatic cancer, lung cancer, breast cancer, fallopian tube cancer, uterine (e.g., endometrial) cancer, and primary peritoneum cancer). In certain embodiments, an additional therapeutic agent administered to a subject in combination with anti-LGALS3 antibody or antigen-binding fragment thereof described herein is administered in the same composition (pharmaceutical composition). In other embodiments, an additional therapeutic agent administered in combination with anti-LGALS3 antibody or an antigen-binding fragment thereof described herein is administered to a subject in a different composition than the anti-LGALS3 antibody or antigen-binding fragment thereof described herein (e.g., two or more pharmaceutical compositions are used).

Patient Population

A subject treated in accordance with the methods provided herein can be any mammal, such as a rodent, a cat, a canine, a horse, a cow, a pig, a monkey, a primate, or a human, etc. In a particular embodiment, the subject is a human. In another particular embodiment, the subject is a canine. As used herein, the terms "subject" and "patient" are used interchangeably.

In certain embodiments, a subject treated in accordance with the methods provided herein has been diagnosed with a LGALS3-positive cancer, including but not limited to, ovary, lung, pancreas, breast, uterine, fallopian tube, or primary peritoneum cancer, or cancer of any other tissue that expresses the LGALS3.

The following examples are offered by way of illustration and not by way of limitation.

EXAMPLES

Example 1. Generation of Anti-Galectin-3 Hybridoma Using AlivaMab® Mouse

The amino acid sequence of the Gal-3 immunogen used to generate antibodies in the Ablexis AlivaMab® Mouse is:

(SEQ ID NO: 53)

ADNFSLHDALSGSGNPNPQGWPGAWGNQPAGAGGYPGASYPGAYPGQAPP

GAYPGQAPPGAYPGAPGAYPGAPAPGVYPGPPSGPGAYPSSGQPSATGAY

PATGPYGAPAGPLIVPYNLPLPGGVVPRMLITILGTVKPNANRIALDFQR

GNDVAFHFNPRFNENNRRVIVCNTKLDNNWGREERQSVFPFESGKPFKIQ

VLVEPDHFKVAVNDAHLLQYNHRVKKLNEISKLGISGDIDLTSASYTMI

To elicit anti-Gal-3 antibody in AlivaMab® Mouse, multiple tolerance breaking strategies to enhance antigen presentation or stimulate T helper cells were used. Once the titers in the serum of animals reached high levels, splenocytes from several mice were used for fusions to generate hybridomas.

Example 2. Screening of the Hybridomas

As a primary screen, ELISA using human Gal-3 was used. Ten enriched clones specific to Gal-3 were obtained.

Figure 3A:
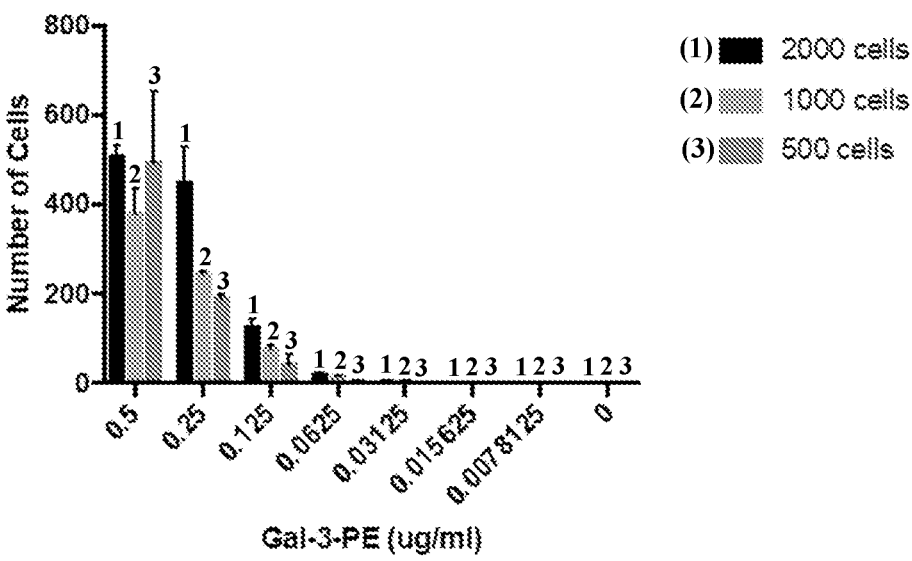
FIGS. 3A-3B illustrate the development and optimization of the assays for Gal-3-PE binding to OVCAR3 cells.
Figure 3B:
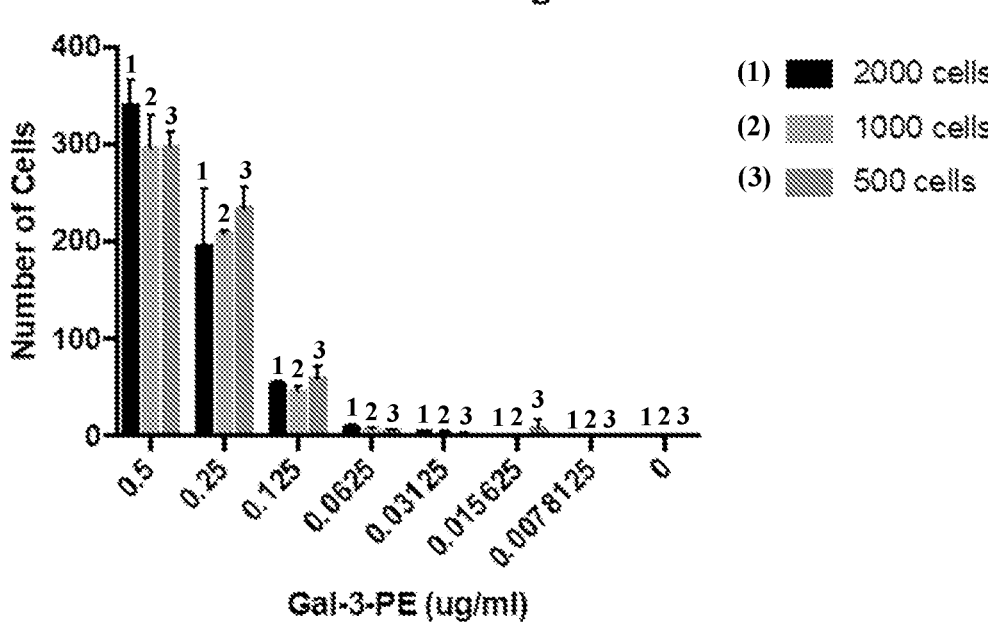

An assay for Gal-3-PE binding to cancer cells was developed as a secondary screen. huGal-3 (Abcam ab89487) was labelled with PE (Innova Biosciences) according to manufacturer's instructions. The assay for Gal-3-PE binding to OVCAR3 cells was performed as follows: cultured SKOV3 cells were trypsinized and washed with culture medium. 500, 1000 or 2000 cells were incubated with various concentrations of Gal-3-PE. The indicated number of OVCAR3 cells were pipetted into a 96-well plate with the indicated amount of Gal-3-PE and incubated on the bench in the dark for 2 hrs prior to being read on a Mirrorball® device (TTP Labtech). Binding of Gal-3-PE to OVCAR3 cells was detected using the Mirrorball® flow cytometer. As shown in FIG. 3A, OVCAR3 cells exhibited a dose-dependent binding to Gal-3-PE. Similarly, MOLT-4 cells also exhibited a dose-dependent binding to Gal-3-PE as shown in FIG. 3B.

The binding assay described above was converted to an assay for inhibition of Gal-3-PE binding to OVCAR3 cells as follows: binding reactions to measure binding of Gal-3-PE to OVCAR3 cells were set up in the presence of PBS (negative control), or the indicated antibody, obtained by enrichment (crude purification) from the clones selected in a primary screen. The extent of binding was measured by flow cytometry was plotted. As shown in FIG. 4, five antibodies (12H7, 20F08, 38E05, 39F02, and 46H02) blocked the binding of Gal-3-PE to OVCAR3 cells. Clone 14D11 (a.k.a., 14D11.2D3) did not block Gal-3-PE binding to OVCAR3 cells in this assay, and thus serves as a negative control.

Example 3. Characterization of the Antibodies

To determine species cross-reactivity of the obtained antibodies, binding to human Gal-3 or mouse Gal-3 was detected using ELISA. As shown in FIGS. 5A-5B, clones 39F02, 38E05 and 46H02, but not clones 20F08 and 12H07, bound mouse Gal-3.

Figure 6A:
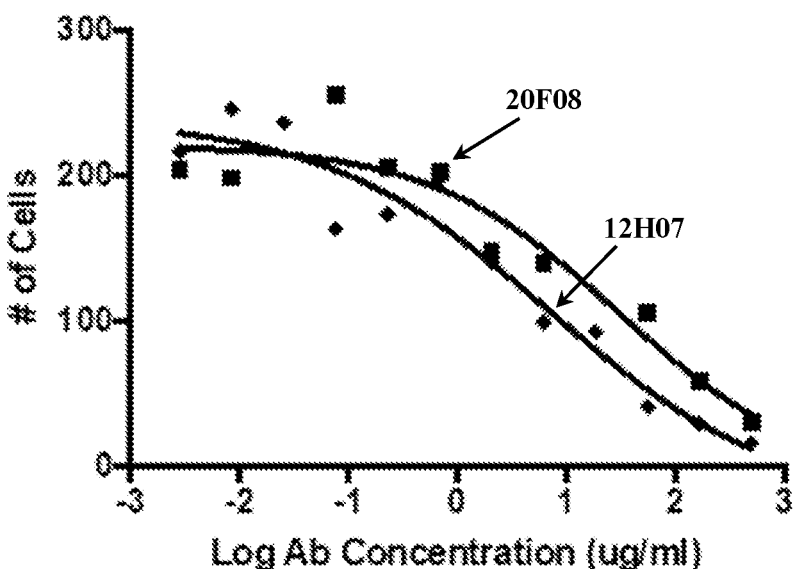
FIGS. 6A-6D shows the dose-response of blockade of Gal-3-PE binding to OVCAR3 cells by purified anti-Gal-3 antibody hits. Reactions to measure binding of Gal-3-PE to OVCAR3 cells were set up in the presence of PBS (negative control), or increasing concentrations of the indicated antibody. Purified antibodies were used in the binding reactions. Shown are the effects of antibody concentration on the extent of inhibition of Gal-3-PE binding to OVCAR3 by antibody clones 20F08 and 12H07 (FIG. 6A), which have the identical sequences, 46H02 (FIG. 6B), clones 38E05 and 39F02 (FIG. 6C), which also have identical sequences, and 14D11.2D3 (FIG. 6D). These data showed that three antibodies (46H02, 20F08, 12H07) exhibit dose-dependent blockade of Gal-3 binding OVCAR3 cells.
Figure 6B:
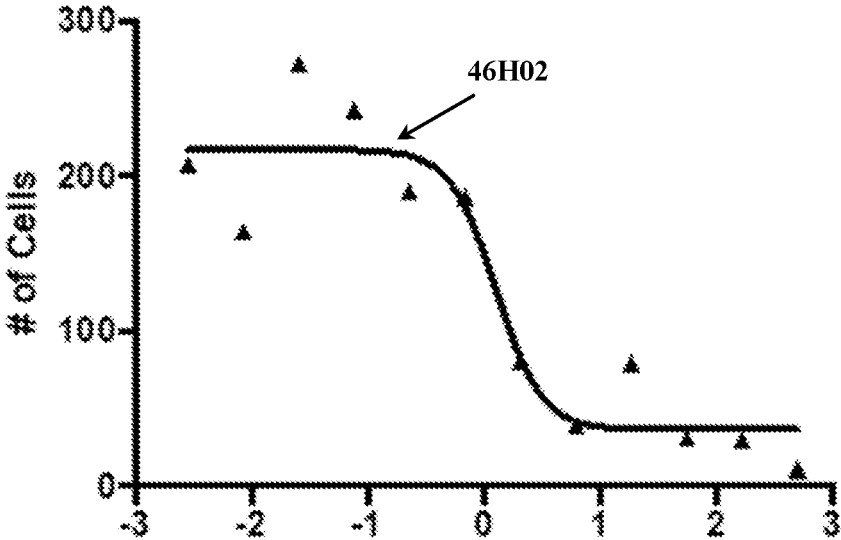
Figure 6C:
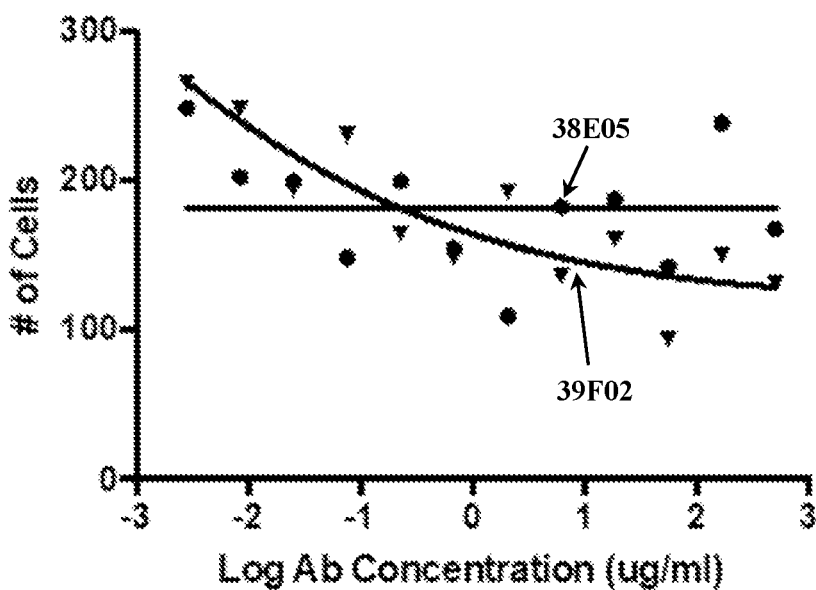
Figure 6D:
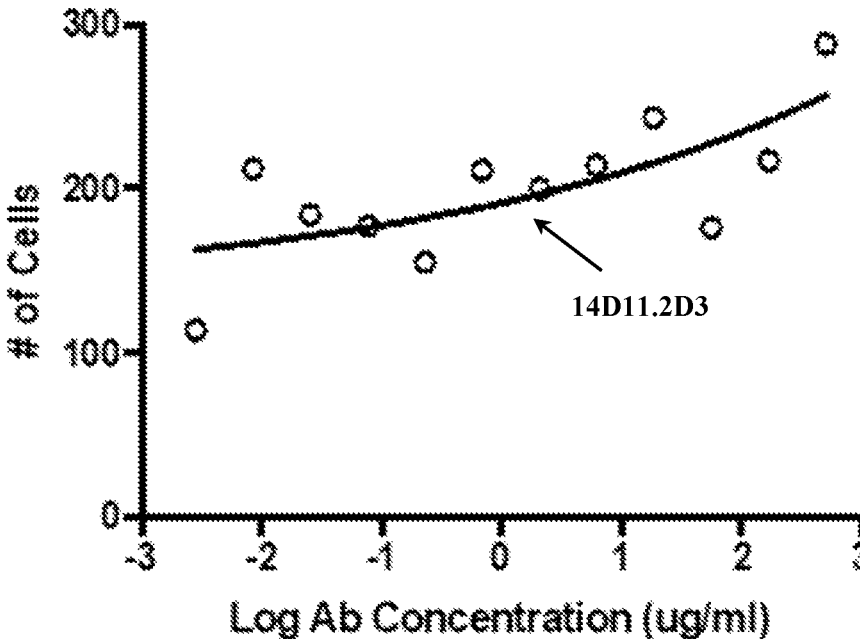

Next, the clones were subjected to determination of dose-response of blockade of Gal-3-PE binding to OVCAR3 cells. The assay for inhibition of Gal-3-PE binding to OVCAR3 cells was performed in the presence of increasing antibody concentrations. Binding reactions to measure binding of Gal-3-PE to OVCAR3 cells were set up in the presence of PBS (negative control), or increasing amounts of the purified antibodies. As shown in FIG. 6A, clones 20F08 and 12H07 showed very similar dose-response of blockade of Gal-3-PE binding to OVCAR3 cells. Interestingly, 20F08 and 12H07 were found to have the identical sequences. As shown in FIG. 6B, clone 46H02 showed a distinctive dose-response of blockade of Gal-3-PE binding to OVCAR3 cells. Clones 38E05 and 39F02, which also have identical sequences, showed very similar dose-response of blockade of Gal-3-PE binding to OVCAR3 cells as shown in FIG. 6C. Clone 14D11 did not block Gal-3-PE binding to OVCAR3 cells in this assay (FIG. 6D).

Figure 7A:
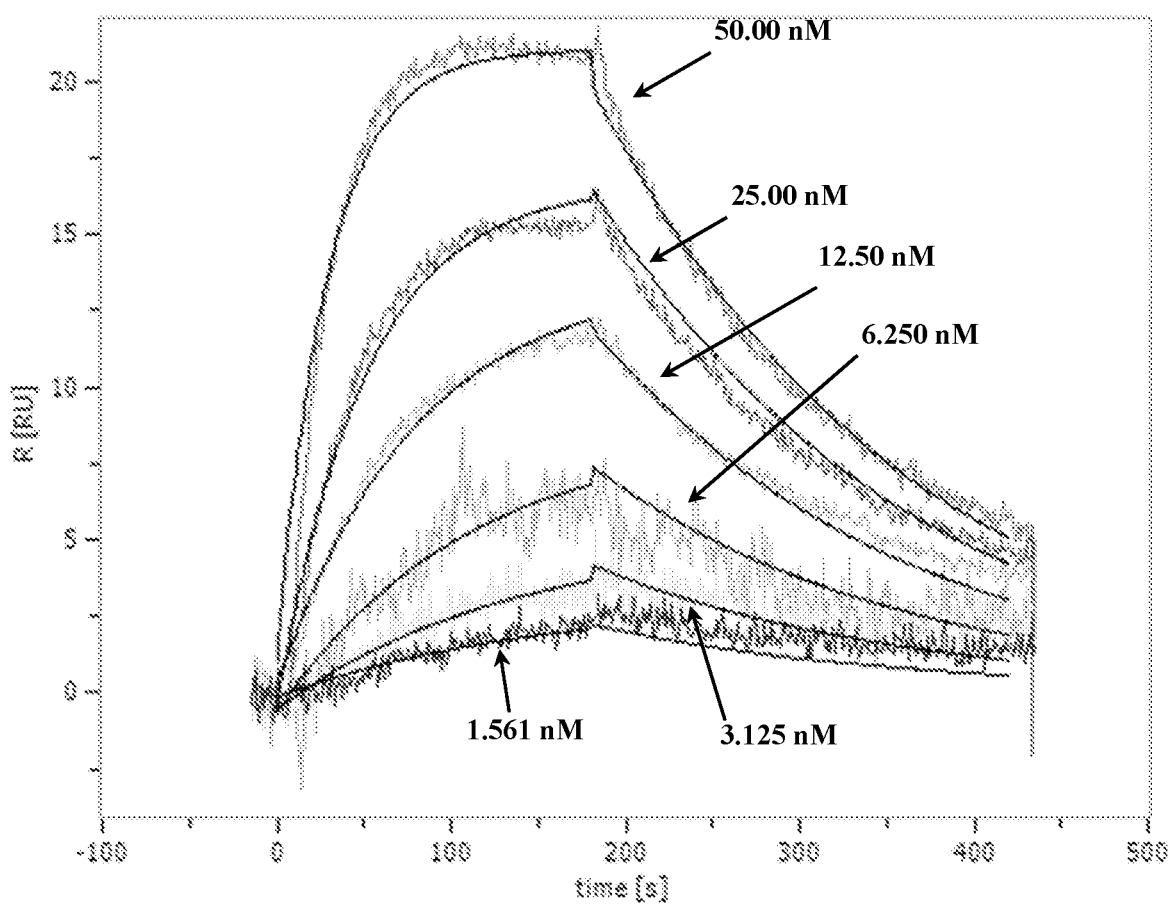
FIGS. 7A-7B show the binding kinetics of monoclonal antibodies (mAbs) 46H02 (FIG. 7A), and 20F08 (FIG. 7B) to human Gal-3 as determined by surface plasmon resonance (SPR). The line graphs depict change in the Resonance Units (RU, which reflects the change in analyte binding capacity of the surface) as a function of time (seconds), upon the addition of the indicated concentrations of the mAbs. These data showed that mAbs 46H02 and 20F08 bind human Gal-3 with a $K_D$ of 10 and 44 nM, respectively.
Figure 7B:
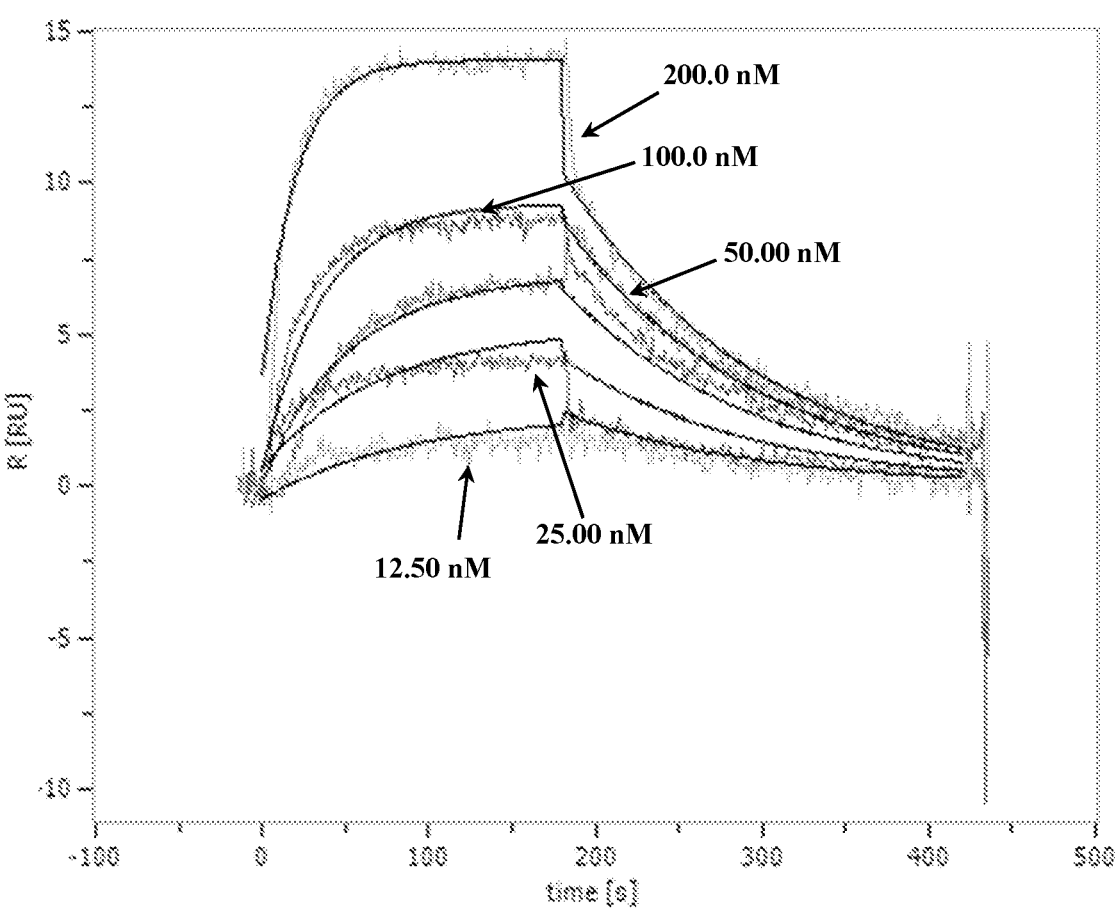

Clones 46H02 and 20F08 were then subjected to determination of binding parameters using surface plasmon resonance (SPR) in the presence of increasing concentrations of these antibodies. As shown in FIGS. 7A-7B, monoclonal antibodies (mAbs) 46H02 (FIG. 7A), and 20F08 (FIG. 7B) showed characteristic binding kinetics to human Gal-3. These data show that mAbs 46H02 and 20F08 bound human Gal-3 with a $K_D$ of 10 and 44 nM, respectively.

Since the first-generation AlivaMab® Mouse (Ablexis) used here produces a mixture of antibodies with human heavy and light chains or hybrid antibodies with human heavy and murine light chains, the clones 12H07, 20F08, 38E05, 39F02, and 46H02 were subjected to light chain species determination by ELISA using anti-mouse kappa, anti-mouse lambda, anti-human kappa, and anti-human lambda antibodies. As shown in FIG. 8, 46H02 has fully human F(ab)$_2$, whereas the other hits have human HC and murine LC.

Figure 9A:
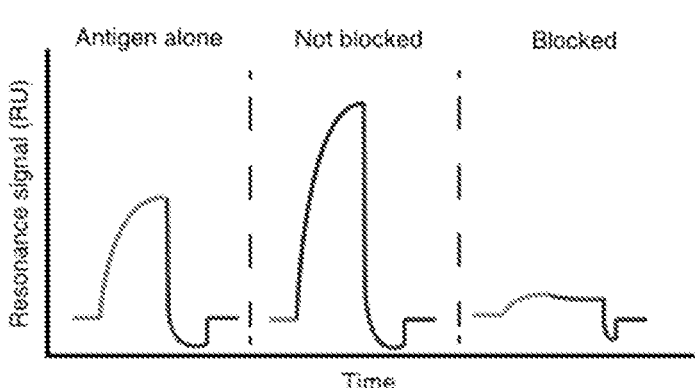
FIGS. 9A-9C show the results of the epitope binning assay for mAbs 46H02 and 14D11.2D2 by surface plasmon resonance (SPR).
Figure 9B:
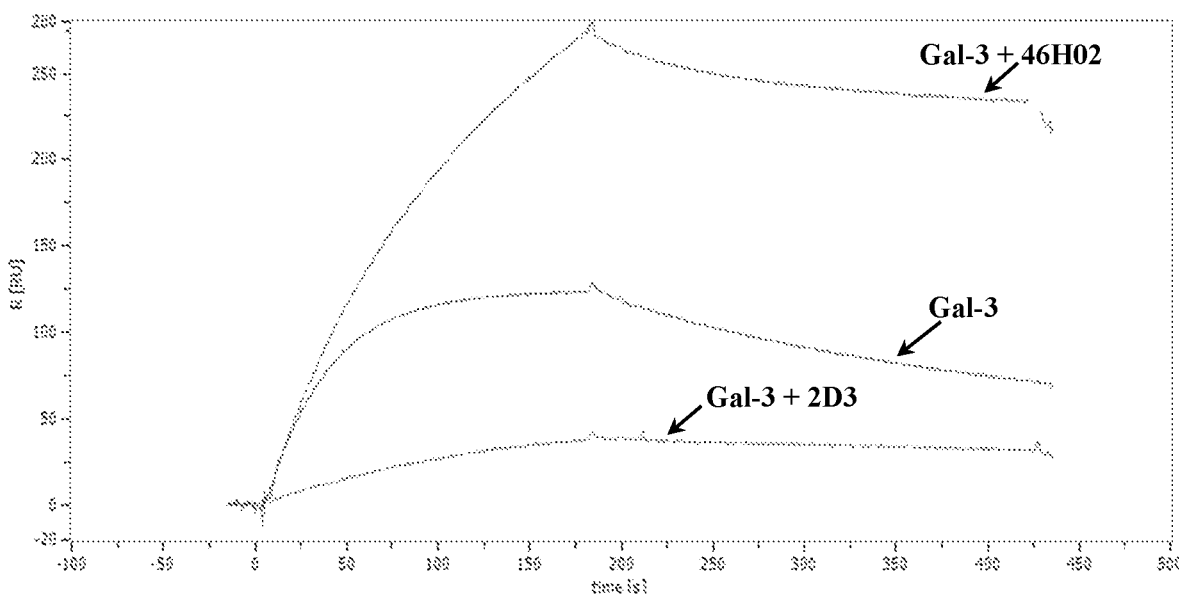
Figure 9C:
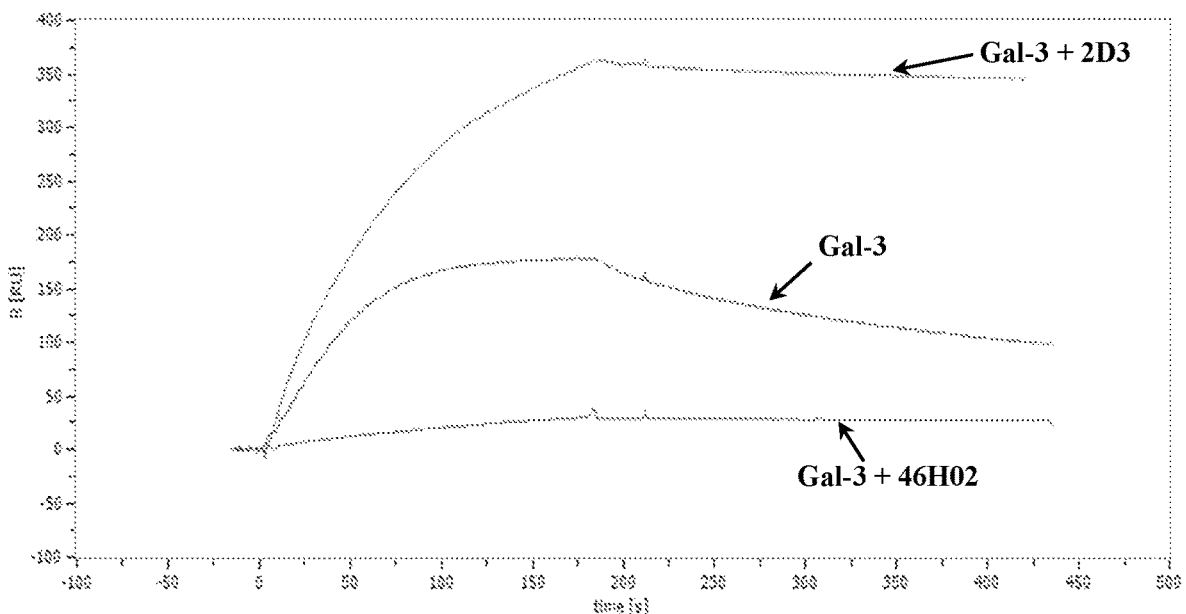

To analyze whether 46H02 and 14D11.2D3 bind overlapping epitopes on Gal-3, an epitope binning assay was carried out using a premix epitope binning assay strategy (FIG. 9A). In this strategy, the test antibody (analyte) is immobilized on a capture surface and a ligand is flowed over the analyte and binding is detected by SPR. The ligand is either the antigen alone or a premixed solution of the antigen complexed with a second antibody. As shown, the antigen alone produces a characteristic SPR profile (left panel) indicating binding of the analyte to the antigen. When the ligand is a premixed solution of the antigen complexed with a second antibody, if the second antibody binds to a distinct epitope on the antigen, a SPR profile indicating binding of the analyte to the antigen is obtained (middle panel). If the second antibody blocks binding of the analyte, the SPR profile shows no binding indicating that the second antibody blocks binding of the analyte (right panel). As a control mimicking the second antibody that blocks binding of the analyte, the test antibody (analyte) itself was used. As shown in FIG. 9B, when mAb 2D3 was used as analyte, Gal-3+14D11.2D3 complex completely inhibited binding. In contrast, Gal-3, or Gal-3+46H02 complex did not inhibit binding (FIG. 9B). Similarly, when mAb 46H02 was used as analyte, Gal-3+ 46H02 complex completely inhibited binding, as shown in FIG. 9C. In contrast, Gal-3, or Gal-3+14D11.2D3 complex did not inhibit binding (FIG. 9C). Therefore, mAbs 46H02 and 14D11 did not compete with each other and therefore bind to separate epitopes.

TABLE 6

| | Table of Sequences | |
|---|---|---|
| SEQ ID NO | Description | Sequence |
| 1 | Amino acid sequence of light chain variable domain (V$_L$) of mAb 46H02 | DVVMTQSPLSLPVTLGQPASISCRSSQSLVYSDGNTYLNWFQQR PGQSPRRLIYKVSNRDSGVPDRFSGSGSGTDFTLKISRVEAEDVG VYYCMQGTHWPLTFGGGTKVEIK |
| 2 | Amino acid sequence of V$_L$ CDR1 of mAb 46H02 | QSLVYSDGNTY |
| 3 | Amino acid sequence of V$_L$ CDR2 of mAb 46H02 | KVS |
| 4 | Amino acid sequence of V$_L$ CDR3 of mAb 46H02 | MQGTHWPLT |
| 5 | Nucleotide Sequence of V$_L$ of mAb 46H02 | GATGTGGTGATGACTCAGAGTCCGCTCAGCCTGCCCGTCACC CTTGGACAGCCGGCCTCCATCTCCTGCAGGTCTAGTCAAAGC CTCGTATACAGTGATGGAAACACCTACTTGAATTGGTTTCAG CAGAGGCCAGGCCAATCTCCAAGGCGCCTAATTTATAAGGTT TCTAACCGGGACTCTGGGGTCCCAGACAGATTCAGCGGCAGT GGGTCAGGCACTGATTTCACACTGAAAATCAGCAGGGTGGA GGCTGAGGATGTTGGGGTTTATTACTGCATGCAAGGTACACA CTGGCCTCTCACTTTCGGCGGAGGGACCAAGGTGGAGATCAA A |
| 6 | Amino acid sequence of heavy chain variable domain (V$_H$) of mAb 46H02 | QVQLVQSGAEVKKPGASVKVSCKASGYTFTGYSMHWVRQAPG QGLEWMGWINPHSGGTNSAQKFQGRVTMTRDTSIGTAYMELN RLRSDDTAVYYCVRDNPITGFDYWGQGTLVTVSS |
| 7 | Amino acid sequence of V$_H$ CDR1 of mAb 46H02 | GYTFTGYS |
| 8 | Amino acid sequence of V$_H$ CDR2 of mAb 46H02 | INPHSGGT |
| 9 | Amino acid sequence of V$_H$ CDR3 of mAb 46H02 | VRDNPITGFDY |
| 10 | Nucleotide sequence of V$_H$ of mAb 46H02 | CAGGTGCAGCTGGTGCAGTCTGGGGCTGAGGTGAAGAAGCC TGGGGCCTCAGTGAAGGTCTCCTGCAAGGCTTCTGGATACAC CTTCACCGGCTATTCTATGCACTGGGTGCGACAGGCCCCTGG ACAAGGGCTTGAGTGGATGGGATGGATCAACCCTCACAGTG GTGGCACAAATTCTGCACAGAAGTTTCAGGGCAGGGTCACCA TGACCAGGGACACGTCCATCGGCACAGCCTACATGGAGCTG AACAGGCTGAGATCTGACGACACGGCCGTGTATTACTGTGTG AGAGATAACCCTATAACTGGGTTTGACTACTGGGGCCAGGGA ACCCTGGTCACCGTCTCCTCAG |
| 11 | GenBank™ accession number NM_002306.4 *Homo sapiens* galectin 3 (LGALS3) | GCCCGCAGCACCTCCTCGCCAGCAGCCGTCCGGAGCCAGCCA ACGAGCGGAAAATGGCAGACAATTTTTCGCTCCATGATGCGT TATCTGGGTCTGGAAACCCAAACCCTCAAGGATGGCCTGGCG CATGGGGGGAACCAGCCTGCTGGGGCAGGGGGCTACCCAGGG GCTTCCTATCCTGGGGCCTACCCCGGGCAGGCACCCCCAGGG GCTTATCCTGGACAGGCACCTCCAGGCGCCTACCCTGGAGCA CCTGGAGCTTATCCCGGAGCACCTGCACCTGGAGTCTACCCA GGGCCACCCAGCGGCCCTGGGGCCTACCCATCTTCTGGACAG CCAAGTGCCACCGGAGCCTACCCTGCCACTGGCCCCTATGGC GCCCCTGCTGGGCCACTGATTGTGCCTTATAACCTGCCTTTGC CTGGGGGAGTGGTGCCTCGCATGCTGATAACAATTCTGGGCA |

TABLE 6-continued

Table of Sequences

| SEQ ID NO | Description | Sequence |
|---|---|---|
| | | CGGTGAAGCCCAATGCAAACAGAATTGCTTTAGATTTCCAAA GAGGGAATGATGTTGCCTTCCACTTTAACCCACGCTTCAATG AGAACAACAGGAGAGTCATTGTTTGCAATACAAAGCTGGAT AATAACTGGGGAAGGGAAGAAAGACAGTCGGTTTTCCCATTT GAAAGTGGGAAACCATTCAAAATACAAGTACTGGTTGAACC TGACCACTTCAAGGTTGCAGTGAATGATGCTCACTTGTTGCA GTACAATCATCGGGTTAAAAAACTCAATGAAATCAGCAAACT GGGAATTTCTGGTGACATAGACCTCACCAGTGCTTCATATAC CATGATATAATCTGAAAGGGGCAGATTAAAAAAAAAAAAAAG AATCTAAACCTTACATGTGTAAAGGTTTCATGTTCACTGTGA GTGAAAATTTTTACATTCATCAATATCCCTCTTGTAAGTCATC TACTTAATAAATATTACAGTGAATTACCTGTCTCAA |
| 12 | GenBank™ accession number NP_002297.2 galectin-3 isoform 1 [*Homo sapiens*] | MADNFSLHDALSGSGNPNPQGWPGAWGNQPAGAGGYPGASYP GAYPGQAPPGAYPGQAPPGAYPGAPGAYPGAPAPGVYPGPPSG PGAYPSSGQPSATGAYPATGPYGAPAGPLIVPYNLPLPGGVVPR MLITILGTVKPNANRIALDFQRGNDVAFHFNPRFNENNRRVIVC NTKLDNNWGREERQSVFPFESGKPFKIQVLVEPDHFKVAVNDA HLLQYNHRVKKLNEISKLGISGDIDLTSASYTMI |
| 13 | Amino acid sequence of light chain variable domain (V$_L$) of mAb 12H07 | ETTVTQSPASLSMAIGEKVTIRCITSTDIDDDMNWYQQKPGEPP KLLISEGNILRPGVPSRFSSSGYGTDFVFAIENMLSEDVADYYCL QSDNLPYTFGGGTKLELK |
| 14 | Amino acid sequence of V$_L$ CDR1 of mAb 12H07 | TDIDDD |
| 15 | Amino acid sequence of V$_L$ CDR2 of mAb 12H07 | EGN |
| 16 | Amino acid sequence of V$_L$ CDR3 of mAb 12H07 | LQSDNLPYT |
| 17 | Nucleotide Sequence of V$_L$ of mAb 12H07 | GAAACAACTGTGACCCAGTCTCCAGCATCCCTGTCCATGGCT ATAGGAGAAAAAGTCACCATCAGATGCATAACCAGCACTGA TATTGATGATGATATGAACTGGTACCAGCAGAAGCCAGGGG AACCTCCTAAGCTCCTTATTTCAGAAGGCAATATTCTTCGTCC TGGAGTCCCATCCCGATTCTCCAGCAGTGGCTACGGTACAGA TTTTGTTTTTGCAATTGAAAACATGCTCTCAGAAGATGTTGCA GATTACTACTGTTTGCAAAGTGATAACTTGCCGTACACGTTC GGAGGGGGGACCAAGCTGGAACTAAAA |
| 18 | Amino acid sequence of heavy chain variable domain (V$_H$) of mAb 12H07 | EVOLVESGGGLVKPGGSLRLSCAASGFIFSNYNINWVRQAPGKG LEWVSCVSRSNYTYYTDSVKGRFTISRDNAKKSLYLQMNSLRA EDTAVYYCARDCGTYGVFDYWGQGTLVTVSS |
| 19 | Amino acid sequence of V$_H$ CDR1 of mAb 12H07 | GFIFSNYN |
| 20 | Amino acid sequence of V$_H$ CDR2 of mAb 12H07 | CVSRSNYT |
| 21 | Amino acid sequence of V$_H$ CDR3 of mAb 12H07 | ARDCGTYGVFDY |

TABLE 6-continued

Table of Sequences

| SEQ ID NO | Description | Sequence |
|---|---|---|
| 22 | Nucleotide Sequence of $V_H$ of mAb 12H07 | GAGGTGCAGCTGGTGGAGTCTGGGGGAGGCCTGGTCAAGCC GGGGGGGTCCCTGAGACTCTCCTGTGCAGCCTCTGGATTTAT ATTCAGTAATTATAATATAAACTGGGTCCGCCAGGCTCCAGG GAAGGGGCTGGAGTGGGTCTCATGTGTTAGTAGGAGTAATTA CACATACTACACAGACTCAGTGAAGGGCCGATTCACCATCTC CAGAGACAACGCCAAGAAGTCACTGTATCTGCAAATGAACA GCCTGAGAGCCGAGGACACGGCTGTGTATTACTGTGCGAGA GACTGTGGGACCTATGGGGTCTTTGACTATTGGGGCCAGGGA ACCCTGGTCACCGTCTCCTCAG |
| 23 | Amino acid sequence of light chain variable domain ($V_L$) of mAb 20F08 | ETTVTQSPASLSMAIGEKVTIRCITSTDIDDDMNWYQQKPGEPP KLLISEGNILRPGVPSRFSSSGYGTDFVFAIENMLSEDVADYYCL QSDNLPYTFGGGTKLELK |
| 24 | Amino acid sequence of $V_L$ CDR1 of mAb 20F08 | TDIDDD |
| 25 | Amino acid sequence of $V_L$ CDR2 of mAb 20F08 | EGN |
| 26 | Amino acid sequence of $V_L$ CDR3 of mAb 20F08 | LQSDNLPYT |
| 27 | Nucleotide Sequence of $V_L$ of mAb 20F08 | GAAACAACTGTGACCCAGTCTCCAGCATCCCTGTCCATGGCT ATAGGAGAAAAAGTCACCATCAGATGCATAACCAGCACTGA TATTGATGATGATATGAACTGGTACCAGCAGAAGCCAGGGG AACCTCCTAAGCTCCTTATTTCAGAAGGCAATATTCTTCGTCC TGGAGTCCCATCCCGATTCTCCAGCAGTGGCTACGGTACAGA TTTTGTTTTTGCAATTGAAAACATGCTCTCAGAAGATGTTGCA GATTACTACTGTTTGCAAAGTGATAACTTGCCGTACACGTTC GGAGGGGGGACCAAGCTGGAACTAAAA |
| 28 | Amino acid sequence of heavy chain variable domain ($V_H$) of mAb 20F08 | EVQLVESGGGLVKPGGSLRLSCAASGFIFSNYNINWVRQAPGKG LEWVSCVSRSNYTYYTDSVKGRFTISRDNAKKSLYLQMNSLRA EDTAVYYCARDCGTYGVFDYWGQGTLVTVSS |
| 29 | Amino acid sequence of $V_H$ CDR1 of mAb 20F08 | GFIFSNYN |
| 30 | Amino acid sequence of $V_H$ CDR2 of mAb 20F08 | CVSRSNYT |
| 31 | Amino acid sequence of $V_H$ CDR3 of mAb 20F08 | ARDCGTYGVFDY |
| 32 | Nucleotide Sequence of $V_H$ of mAb 20F08 | GAGGTGCAGCTGGTGGAGTCTGGGGGAGGCCTGGTCAAGCC GGGGGGGTCCCTGAGACTCTCCTGTGCAGCCTCTGGATTTAT ATTCAGTAATTATAATATAAACTGGGTCCGCCAGGCTCCAGG GAAGGGGCTGGAGTGGGTCTCATGTGTTAGTAGGAGTAATTA CACATACTACACAGACTCAGTGAAGGGCCGATTCACCATCTC CAGAGACAACGCCAAGAAGTCACTGTATCTGCAAATGAACA GCCTGAGAGCCGAGGACACGGCTGTGTATTACTGTGCGAGA GACTGTGGGACCTATGGGGTCTTTGACTATTGGGGCCAGGGA ACCCTGGTCACCGTCTCCTCAG |

TABLE 6-continued

| Table of Sequences | | |
|---|---|---|
| SEQ ID NO | Description | Sequence |
| 33 | Amino acid sequence of light chain variable domain (V_L) of mAb 38E05 | DIVMSQSPSSLAVSVGEKVTLSCKSSQSLLYGDDQKNYLAWYQ QKPGQSPKLLLYWASTWESGVPDRFTGSGSGTDFTLTISSVKAA DLAVYYCQQYYSYPWTFGGGTKLEIK |
| 34 | Amino acid sequence of V_L CDR1 of mAb 38E05 | QSLLYGDDQKNY |
| 35 | Amino acid sequence of V_L CDR2 of mAb 38E05 | WAS |
| 36 | Amino acid sequence of V_L CDR3 of mAb 38E05 | QQYYSYPWT |
| 37 | Nucleotide Sequence of V_L of mAb 38E05 | GACATTGTGATGTCACAGTCTCCATCCTCCCTAGCTGTGTCAG TTGGAGAGAAGGTTACTCTGAGCTGCAAGTCCAGTCAGAGCC TTTTATATGGTGACGATCAAAAGAACTACTTGGCCTGGTACC AACAGAAACCAGGACAGTCTCCTAAACTGCTTCTTTACTGGG CATCCACTTGGGAATCTGGGGTCCCTGATCGCTTCACAGGCA GTGGATCTGGGACAGATTTCACTCTCACCATCAGCAGTGTGA AGGCTGCAGACCTGGCAGTTTATTACTGTCAGCAATATTATA GCTATCCGTGGACGTTCGGTGGAGGCACCAAGCTGGAAATCA AA |
| 38 | Amino acid sequence of heavy chain variable domain (V_H) of mAb 38E05 | EVQLLESGGGLVQPGGSLRLSCAASGFTLSNYAMSWVRQAPGK GLEWVSAISGSGGGTYNADSVKGRFTISRDNSKNTLYLQMNSL RAEDTAVYYCAKEAWISYFDYWGQGTLVTVSS |
| 39 | Amino acid sequence of V_H CDR1 of mAb 38E05 | GFTLSNYA |
| 40 | Amino acid sequence of V_H CDR2 of mAb 38E05 | ISGSGGGT |
| 41 | Amino acid sequence of V_H CDR3 of mAb 38E05 | AKEAWISYFDY |
| 42 | Nucleotide Sequence of V_H of mAb 38E05 | GAAGTACAGCTGTTGGAGTCTGGGGGAGGCTTGGTACAGCCT GGGGGGTCCCTGAGACTCTCCTGTGCAGCCTCTGGATTCACC CTTAGTAACTATGCCATGAGCTGGGTCCGCCAGGCGCCAGGG AAGGGGCTGGAGTGGGTCTCAGCTATCAGTGGTAGTGGTGGT GGCACATACAACGCAGACTCCGTGAAGGGCCGGTTCACCATC TCCAGAGACAATTCCAAGAACACGCTGTATCTGCAAATGAAC AGCCTGAGAGCCGAGGACACGGCCGTGTATTACTGTGCGAA AGAGGCGTGGATCTCGTACTTTGACTACTGGGGCCAGGGGAC CCTGGTCACCGTCTCCTCAG |
| 43 | Amino acid sequence of light chain variable domain (V_L) of mAb 39F02 | DIVMSQSPSSLAVSVGEKVTLSCKSSQSLLYGDDQKNYLAWYQ QKPGQSPKLLLYWASTWESGVPDRFTGSGSGTDFTLTISSVKAA DLAVYYCQQYYSYPWTFGGGTKLEIK |
| 44 | Amino acid sequence of V_L CDR1 of mAb 39F02 | QSLLYGDDQKNY |

TABLE 6-continued

| Table of Sequences | | |
|---|---|---|

| SEQ ID NO | Description | Sequence |
|---|---|---|
| 45 | Amino acid sequence of V$_L$ CDR2 of mAb 39F02 | WAS |
| 46 | Amino acid sequence of V$_L$ CDR3 of mAb 39F02 | QQYYSYPWT |
| 47 | Nucleotide Sequence of V$_L$ of mAb 39F02 | GACATTGTGATGTCACAGTCTCCATCCTCCCTAGCTGTGTCAG TTGGAGAGAAGGTTACTCTGAGCTGCAAGTCCAGTCAGAGCC TTTTATATGGTGACGATCAAAAGAACTACTTGGCCTGGTACC AACAGAAACCAGGACAGTCTCCTAAACTGCTTCTTTACTGGG CATCCACTTGGGAATCTGGGGTCCCTGATCGCTTCACAGGCA GTGGATCTGGGACAGATTTCACTCTCACCATCAGCAGTGTGA AGGCTGCAGACCTGGCAGTTTATTACTGTCAGCAATATTATA GCTATCCGTGGACGTTCGGTGGAGGCACCAAGCTGGAAATCA AA |
| 48 | Amino acid sequence of heavy chain variable domain (V$_H$) of mAb 39F02 | EVQLLESGGGLVQPGGSLRLSCAASGFTLSNYAMSWVRQAPGK GLEWVSAISGSGGGTYNADSVKGRFTISRDNSKNTLYLQMNSL RAEDTAVYYCAKEAWISYFDYWGQGTLVTVSS |
| 49 | Amino acid sequence of V$_H$ CDR1 of mAb 39F02 | GFTLSNYA |
| 50 | Amino acid sequence of V$_H$ CDR2 of mAb 39F02 | ISGSGGGT |
| 51 | Amino acid sequence of V$_H$ CDR3 of mAb 39F02 | AKEAWISYFDY |
| 52 | Nucleotide Sequence of V$_H$ of mAb 39F02 | GAAGTACAGCTGTTGGAGTCTGGGGGAGGCTTGGTACAGCCT GGGGGGTCCCTGAGACTCTCCTGTGCAGCCTCTGGATTCACC CTTAGTAACTATGCCATGAGCTGGGTCCGCCAGGCGCCAGGG AAGGGGCTGGAGTGGGTCTCAGCTATCAGTGGTAGTGGTGGT GGCACATACAACGCAGACTCCGTGAAGGGCCGGTTCACCATC TCCAGAGACAATTCCAAGAACACGCTGTATCTGCAAATGAAC AGCCTGAGAGCCGAGGACACGGCCGTGTATTACTGTGCGAA AGAGGCGTGGATCTCGTACTTTGACTACTGGGGCCAGGGGAC CCTGGTCACCGTCTCCTCAG |
| 53 | GAL-3 immunogen | ADNFSLHDALSGSGNPNPQGWPGAWGNQPAGAGGYPGASYPG AYPGQAPPGAYPGQAPPGAYPGAPGAYPGAPAPGVYPGPPSGP GAYPSSGQPSATGAYPATGPYGAPAGPLIVPYNLPLPGGVVPRM LITILGTVKPNANRIALDFQRGNDVAFHFNPRFNENNRRVIVCNT KLDNNWGREERQSVPPFESGKPFKIQVLVEPDHFKVAVNDAHL LQYNHRVKKLNEISKLGISGDIDLTSASYTMI |

All publications, patents and patent applications cited in this specification are herein incorporated by reference as if each individual publication or patent application were specifically and individually indicated to be incorporated by reference. Although the foregoing present technology has been described in some detail by way of illustration and example for purposes of clarity of understanding, it will be readily apparent to those of ordinary skill in the art in light of the teachings of the present technology that certain changes and modifications can be made thereto

---

What is claimed is:

1. An antibody or an antigen-binding fragment thereof that specifically binds to a Galectin-3 (LGALS3), wherein the antibody or antigen-binding fragment thereof comprises a heavy chain variable region ($V_H$) and a light chain variable region ($V_L$), wherein:

(a) the $V_H$ comprises a $V_H$ complementarity determining region (CDR)1 sequence comprising SEQ ID NO: 7, a $V_H$ CDR2 sequence comprising SEQ ID NO: 8, and a $V_H$ CDR3 sequence comprising SEQ ID NO: 9, and the $V_L$ comprises a $V_L$ CDR1 sequence comprising SEQ ID NO: 2, a $V_L$ CDR2 sequence comprising SEQ ID NO: 3, and a $V_L$ CDR3 sequence comprising SEQ ID NO: 4;

(b) the $V_H$ comprises a $V_H$ complementarity determining region (CDR)1 sequence comprising SEQ ID NO: 19, a $V_H$ CDR2 sequence comprising SEQ ID NO: 20, and a $V_H$ CDR3 sequence comprising SEQ ID NO: 21, and the $V_L$ comprises a $V_L$ CDR1 sequence comprising SEQ ID NO: 14, a $V_L$ CDR2 sequence comprising SEQ ID NO: 15, and a $V_L$ CDR3 sequence comprising SEQ ID NO: 16;

(c) the $V_H$ comprises a $V_H$ complementarity determining region (CDR)1 sequence comprising SEQ ID NO: 29, a $V_H$ CDR2 sequence comprising SEQ ID NO: 30, and a $V_H$ CDR3 sequence comprising SEQ ID NO: 31, and the $V_L$ comprises a $V_L$ CDR1 sequence comprising SEQ ID NO: 24, a $V_L$ CDR2 sequence comprising SEQ ID NO: 25, and a $V_L$ CDR3 sequence comprising SEQ ID NO: 26;

(d) the $V_H$ comprises a $V_H$ complementarity determining region (CDR)1 sequence comprising SEQ ID NO: 39, a $V_H$ CDR2 sequence comprising SEQ ID NO: 40, and a $V_H$ CDR3 sequence comprising SEQ ID NO: 41, and the $V_L$ comprises a $V_L$ CDR1 sequence comprising SEQ ID NO: 34, a $V_L$ CDR2 sequence comprising SEQ ID NO: 35, and a $V_L$ CDR3 sequence comprising SEQ ID NO: 36; or (e) the $V_H$ comprises a $V_H$ complementarity determining region (CDR)1 sequence comprising SEQ ID NO: 49, a $V_H$ CDR2 sequence comprising SEQ ID NO: 50, and a $V_H$ CDR3 sequence comprising SEQ ID NO: 51, and the $V_L$ comprises a $V_L$ CDR1 sequence comprising SEQ ID NO: 44, a $V_L$ CDR2 sequence comprising SEQ ID NO: 45, and a $V_L$ CDR3 sequence comprising SEQ ID NO: 46, optionally wherein the antibody or antigen-binding fragment is generated by immunizing a transgenic mouse; or the antibody is a monoclonal antibody; or the antigen-binding fragment is a Fab, F(ab')$_2$, Fab', Fv or scFv.

2. The antibody or antigen-binding fragment of claim 1, wherein the $V_H$ comprises an amino acid sequence selected from the group consisting of SEQ ID NO: 6, SEQ ID NO: 18, SEQ ID NO: 28, SEQ ID NO: 38, and SEQ ID NO: 48 or wherein the $V_L$ comprises an amino acid sequence selected from the group consisting of SEQ ID NO: 1, SEQ ID NO: 13, SEQ ID NO: 23, SEQ ID NO: 33, and SEQ ID NO: 43.

3. A polynucleotide comprising nucleic acid sequences encoding the antibody or antigen-binding fragment of claim 2.

4. The polynucleotide of claim 3, wherein the polynucleotide comprises the polynucleotide of any one of SEQ ID NO: 5, SEQ ID NO: 17, SEQ ID NO: 27, SEQ ID NO: 37, SEQ ID NO: 47, SEQ ID NO: 10, SEQ ID NO: 22, SEQ ID NO: 32, SEQ ID NO: 42, or SEQ ID NO: 52.

5. A vector comprising the polynucleotide of claim 3, optionally wherein the polynucleotide is operably linked to a promoter.

6. An isolated cell comprising the polynucleotide of claim 3 or a vector comprising the polynucleotide.

7. The antibody or antigen-binding fragment of claim 1, comprising a $V_H$ amino acid sequence and a $V_L$ amino acid sequence selected from the group consisting of SEQ ID NO: 6 and SEQ ID NO: 1, SEQ ID NO: 18 and SEQ ID NO: 13, SEQ ID NO: 28 and SEQ ID NO: 23, SEQ ID NO: 38 and SEQ ID NO: 33, and SEQ ID NO: 48 and SEQ ID NO: 43, respectively.

8. The antibody or antigen-binding fragment of claim 1, wherein the antibody or antigen-binding fragment thereof comprises a human or humanized heavy chain variable domain ($V_H$) and/or a human or humanized a light chain variable domain ($V_L$); or wherein the antibody or antigen-binding fragment is a humanized or fully human antibody or antigen-binding fragment thereof.

9. The antibody or antigen-binding fragment of claim 1, wherein the antibody comprises human-derived heavy and light chain constant regions, optionally wherein the heavy chain constant region has an isotype selected from the group consisting of gamma 1, gamma 2, gamma 3, and gamma 4; or wherein the light chain constant region has an isotype selected from the group consisting of kappa and lambda.

10. The antibody or antigen-binding fragment of claim 1, wherein the antibody is an immunoglobulin comprising two identical heavy chains and two identical light chains, optionally wherein the immunoglobulin is an IgG; or wherein the antibody or antigen-binding fragment inhibits Gal-3-Phycoerythrin (PE) binding to ovarian tumor cells, optionally wherein the ovarian tumor cells are OVCAR3 cells; or wherein the antibody or antigen-binding fragment thereof inhibits binding of LGALS3 to a glycosylated cell surface receptor; or wherein the antibody or antigen-binding fragment inhibits binding of LGALS3 to a glycosylated growth factor receptor; or wherein the antibody or antigen-binding fragment inhibits binding of LGALS3 to one or more of glycosylated mucin-1 (MUC1), mucin-4 (MUC4), mucin-16 (MUC16), a disialoganglioside, GD2, epidermal growth factor receptor (EGFR), platelet-derived growth factor receptor (PDGFR), insulin-like growth factor receptor (IGFR), an integrin or CTLA4, optionally wherein the glycosylated MUC16 is N-glycosylated at Asn1800 or Asn1806; or wherein the antibody or antigen-binding fragment inhibits growth of a tumor that expresses a glycosylated form of MUC16.

11. An antibody conjugate comprising the antibody or antigen-binding fragment of claim 1 conjugated to an agent, optionally wherein the agent is an imaging agent or a cytotoxic agent.

12. The antibody or antigen-binding fragment of claim 1, wherein the antibody or antigen-binding fragment is a bispecific antibody, optionally wherein the bispecific antibody specifically binds CD3 or wherein the bispecific antibody comprises an immunoglobulin that specifically binds LGALS3, wherein the light chain of the immunoglobulin is conjugated via a peptide linker to a single chain variable fragment (scFv) that specifically binds to CD3.

13. A bispecific antibody conjugate comprising the bispecific antibody of claim 12 conjugated to an agent, optionally wherein the agent is an imaging agent or a cytotoxic agent.

14. An scFv conjugate comprising an scFv of the antigen binding fragment of claim 1 conjugated to an agent, optionally wherein the agent is an imaging agent or a cytotoxic agent.

15. A chimeric antigen receptor (CAR) comprising: the antibody or antigen-binding fragment of claim 1, optionally wherein the antigen-binding fragment is a scFv.

16. A T-cell that recombinantly expresses the CAR of claim 15.

17. A pharmaceutical composition comprising: a therapeutically effective amount of the antibody or antigen-binding fragment of claim 1; and a pharmaceutically acceptable carrier.

18. A method of treating cancer in a patient in need thereof, comprising administering to said patient an effective amount of the pharmaceutical composition of claim 17, optionally wherein the pharmaceutical composition inhibits metastasis in the patient.

19. The method of claim 18, wherein said cancer is a cancer of the ovary, lung, pancreas, breast, uterine, fallopian tube, or primary peritoneum or wherein said cancer is a metastatic cancer.

20. The method of claim 18, wherein the method further comprises administering a therapeutically effective amount of an additional therapeutic agent to the patient.

* * * * *